United States Patent
Connor

(10) Patent No.: US 11,944,316 B2
(45) Date of Patent: Apr. 2, 2024

(54) JANJUA ANEURYSM NET AND OTHER INTRASACULAR ANEURYSM OCCLUSION DEVICES

(71) Applicant: Robert A. Connor, St. Paul, MN (US)

(72) Inventor: Robert A. Connor, St. Paul, MN (US)

(73) Assignee: Aneuclose LLC, Ham Lake, MN (US)

( * ) Notice: Subject to any disclaimer, the term of this patent is extended or adjusted under 35 U.S.C. 154(b) by 0 days.

(21) Appl. No.: 18/374,602

(22) Filed: Sep. 28, 2023

(65) Prior Publication Data
US 2024/0023970 A1   Jan. 25, 2024

Related U.S. Application Data

(63) Continuation-in-part of application No. 18/135,153, filed on Apr. 15, 2023, which is a continuation-in-part of application No. 17/970,510, filed on Oct. 20, 2022, application No. 18/374,602 is a continuation-in-part of application No. 17/970,510, filed on Oct. 20, 2022, and a continuation-in-part of application No. 17/965,502, filed on Oct. 13, 2022, said application No. 18/135,153 is a continuation-in-part of application No. 17/965,502, filed on Oct. 13, 2022, said application No. 17/970,510 is a continuation-in-part of application No. 17/965,502, filed on Oct. 13, 2022, which is a continuation-in-part of application No. 17/829,313, filed on May 31, 2022, now abandoned, said application No. 17/970,510 is a continuation-in-part of application No. 17/829,313, filed on May 31, 2022, now abandoned, said application No. 18/135,153 is a continuation-in-part of application No. 17/829,313, filed on May 31, 2022, now abandoned, application No. 18/374,602 is a continuation-in-part of application No. 17/829,313, filed on May 31, 2022, now abandoned, which is a continuation-in-part of application No. 17/485,390, filed on Sep. 25, 2021, now Pat. No. 11,471,164, said (Continued)

(51) Int. Cl.
*A61B 17/12* (2006.01)
*A61B 34/00* (2016.01)
*A61B 17/00* (2006.01)

(52) U.S. Cl.
CPC .. *A61B 17/12172* (2013.01); *A61B 17/12113* (2013.01); *A61B 34/73* (2016.02); *A61B 2017/00323* (2013.01)

(58) Field of Classification Search
CPC ........ A61B 17/12113; A61B 17/12118; A61B 17/12168; A61B 17/12172
See application file for complete search history.

(56) References Cited

U.S. PATENT DOCUMENTS 6,238,403 B1 * 5/2001 Greene, Jr. ........... A61L 31/145
                                                            606/108
7,153,323 B1 * 12/2006 Teoh ................ A61B 17/12113
                                                            623/1.23

(Continued)

*Primary Examiner* — Diane D Yabut
*Assistant Examiner* — Christina C Lauer

(57) ABSTRACT

Disclosed herein are intrasacular aneurysm occlusion devices with nested proximal and distal meshes. A proximal mesh covers the aneurysm neck. A flexible distal mesh expands to fill even an irregularly-shaped aneurysm sac when it is expanded by the insertion of embolic members and/or material.

1 Claim, 9 Drawing Sheets

Related U.S. Application Data application No. 17/970,510 is a continuation-in-part of application No. 17/476,845, filed on Sep. 16, 2021, now Pat. No. 11,583,289, said application No. 17/965,502 is a continuation of application No. 17/476,845, filed on Sep. 16, 2021, now Pat. No. 11,583,289, said application No. 17/829,313 is a continuation-in-part of application No. 17/476,845, filed on Sep. 16, 2021, now Pat. No. 11,583,289, and a continuation-in-part of application No. 17/472,674, filed on Sep. 12, 2021, now abandoned, and a continuation-in-part of application No. 17/467,680, filed on Sep. 7, 2021, now abandoned, and a continuation-in-part of application No. 17/466,497, filed on Sep. 3, 2021, now Pat. No. 11,357,511, and a continuation-in-part of application No. 17/363,652, filed on Jun. 21, 2021, now abandoned, and a continuation-in-part of application No. 17/220,002, filed on Apr. 1, 2021, now Pat. No. 11,464,518, which is a continuation-in-part of application No. 17/214,827, filed on Mar. 27, 2021, now Pat. No. 11,484,322, said application No. 17/829,313 is a continuation-in-part of application No. 17/214,827, filed on Mar. 27, 2021, now Pat. No. 11,484,322, said application No. 17/220,002 is a continuation-in-part of application No. 17/211,446, filed on Mar. 24, 2021, now abandoned, said application No. 17/829,313 is a continuation-in-part of application No. 17/211,446, filed on Mar. 24, 2021, now abandoned, said application No. 17/220,002 is a continuation-in-part of application No. 16/693,267, filed on Nov. 23, 2019, now abandoned, and a continuation-in-part of application No. 16/660,929, filed on Oct. 23, 2019, now Pat. No. 11,471,163, said application No. 16/693,267 is a continuation-in-part of application No. 16/660,929, filed on Oct. 23, 2019, now Pat. No. 11,471,163, and a continuation-in-part of application No. 16/541,241, filed on Aug. 15, 2019, now abandoned, said application No. 16/660,929 is a continuation-in-part of application No. 16/541,241, filed on Aug. 15, 2019, now abandoned, said application No. 16/693,267 is a continuation-in-part of application No. 15/865,822, filed on Jan. 9, 2018, now Pat. No. 10,716,573, said application No. 16/660,929 is a continuation-in-part of application No. 15/865,822, filed on Jan. 9, 2018, now Pat. No. 10,716,573, said application No. 16/541,241 is a continuation-in-part of application No. 15/865,822, filed on Jan. 9, 2018, now Pat. No. 10,716,573, said application No. 16/660,929 is a continuation-in-part of application No. 15/861,482, filed on Jan. 3, 2018, now abandoned, said application No. 16/693,267 is a continuation-in-part of application No. 15/861,482, filed on Jan. 3, 2018, now abandoned, said application No. 15/865,822 is a continuation-in-part of application No. 15/081,909, filed on Mar. 27, 2016, now abandoned, said application No. 15/861,482 is a continuation-in-part of application No. 15/080,915, filed on Mar. 25, 2016, now Pat. No. 10,028,747, which is a continuation-in-part of application No. 14/526,600, filed on Oct. 29, 2014, now abandoned, said application No. 15/865,822 is a continuation-in-part of application No. 14/526,600, filed on Oct. 29, 2014, now abandoned, said application No. 15/081,909 is a continuation-in-part of application No. 14/526,600, filed on Oct. 29, 2014, now abandoned, said application No. 15/861,482 is a continuation-in-part of application No. 14/526,600, filed on Oct. 29, 2014, now abandoned, which is a continuation-in-part of application No. 12/989,048, filed on Oct. 21, 2010, now Pat. No. 8,974,487.

(60) Provisional application No. 63/119,774, filed on Dec. 1, 2020, provisional application No. 62/794,607, filed on Jan. 19, 2019, provisional application No. 62/794,609, filed on Jan. 19, 2019, provisional application No. 62/720,173, filed on Aug. 21, 2019, provisional application No. 62/589,754, filed on Nov. 22, 2017, provisional application No. 62/472,519, filed on Mar. 16, 2017, provisional application No. 62/444,860, filed on Jan. 11, 2017, provisional application No. 61/897,245, filed on Oct. 30, 2013, provisional application No. 61/126,047, filed on May 1, 2008, provisional application No. 61/126,027, filed on May 1, 2008.

(56) References Cited

U.S. PATENT DOCUMENTS

| | | | | |
|---|---|---|---|---|
| 7,695,488 | B2 * | 4/2010 | Berenstein | A61B 17/12177 606/191 |
| 8,690,907 | B1 * | 4/2014 | Janardhan | A61B 17/221 606/200 |
| 2006/0155323 | A1 * | 7/2006 | Porter | A61B 17/12022 606/200 |
| 2009/0287294 | A1 * | 11/2009 | Rosqueta | A61B 17/12118 623/1.15 |
| 2009/0318948 | A1 * | 12/2009 | Linder | A61B 17/12181 606/191 |

* cited by examiner

JANJUA ANEURYSM NET AND OTHER INTRASACULAR ANEURYSM OCCLUSION DEVICES

CROSS-REFERENCE TO RELATED APPLICATIONS

This application is a continuation-in-part of U.S. patent application Ser. No. 18/135,153 filed on 2023 Apr. 10, a continuation-in-part of U.S. patent application Ser. No. 17/970,510 filed on 2022 Oct. 20, a continuation-in-part of U.S. patent application Ser. No. 17/965,502 filed on 2022 Oct. 13, and a continuation-in-part of U.S. patent application Ser. No. 17/829,313 filed on 2022 May 31.

U.S. patent application Ser. No. 18/135,153 was a continuation-in-part of U.S. patent application Ser. No. 17/970,510 filed on 2022 Oct. 20, a continuation-in-part of U.S. patent application Ser. No. 17/965,502 filed on 2022 Oct. 13, and a continuation-in-part of U.S. patent application Ser. No. 17/829,313 filed on 2022 May 31. U.S. patent application Ser. No. 17/970,510 was a continuation-in-part of U.S. patent application Ser. No. 17/965,502 filed on 2022 Oct. 13, a continuation-in-part of U.S. patent application Ser. No. 17/829,313 filed on 2022 May 31, and a continuation-in-part of U.S. patent application Ser. No. 17/476,845 filed on 2021 Sep. 16.

U.S. patent application Ser. No. 17/829,313 was a continuation-in-part of U.S. patent application Ser. No. 17/485,390 filed on 2021 Sep. 25, was a continuation-in-part of U.S. patent application Ser. No. 17/476,845 filed on 2021 Sep. 16, was a continuation-in-part of U.S. patent application Ser. No. 17/472,674 filed on 2021 Sep. 12, was a continuation-in-part of U.S. patent application Ser. No. 17/467,680 filed on 2021 Sep. 7, was a continuation-in-part of U.S. patent application Ser. No. 17/466,497 filed on 2021 Sep. 3, was a continuation-in-part of U.S. patent application Ser. No. 17/353,652 filed on 2021 Jun. 21, was a continuation-in-part of U.S. patent application Ser. No. 17/220,002 filed on 2021 Apr. 1, was a continuation-in-part of U.S. patent application Ser. No. 17/214,827 filed on 2021 Mar. 27, was a continuation-in-part of U.S. patent application Ser. No. 17/211,446 filed on 2021 Mar. 24, was a continuation-in-part of U.S. patent application Ser. No. 16/693,267 filed on 2019 Nov. 23, and was a continuation-in-part of U.S. patent application Ser. No. 16/660,929 filed on 2019 Oct. 23.

U.S. patent application Ser. No. 17/220,002 was a continuation-in-part of U.S. patent application Ser. No. 17/214,827 filed on 2021 Mar. 27. U.S. patent application Ser. No. 17/220,002 was a continuation-in-part of U.S. patent application Ser. No. 17/211,446 filed on 2021 Mar. 24. U.S. patent application Ser. No. 17/220,002 claimed the priority benefit of U.S. provisional patent application 63/119,774 filed on 2020 Dec. 1. U.S. patent application Ser. No. 17/220,002 was a continuation-in-part of U.S. patent application Ser. No. 16/693,267 filed on 2019 Nov. 23. U.S. patent application Ser. No. 17/220,002 was a continuation-in-part of U.S. patent application Ser. No. 16/660,929 filed on 2019 Oct. 23.

U.S. patent application Ser. No. 16/693,267 was a continuation-in-part of U.S. patent application Ser. No. 16/660,929 filed on 2019 Oct. 23. U.S. patent application Ser. No. 16/693,267 claimed the priority benefit of U.S. provisional patent application 62/794,609 filed on 2019 Jan. 19. U.S. patent application Ser. No. 16/693,267 claimed the priority benefit of U.S. provisional patent application 62/794,607 filed on 2019 Jan. 19. U.S. patent application Ser. No. 16/693,267 was a continuation-in-part of U.S. patent application Ser. No. 16/541,241 filed on 2019 Aug. 15. U.S. patent application Ser. No. 16/693,267 was a continuation-in-part of U.S. patent application Ser. No. 15/865,822 filed on 2018 Jan. 9 which issued as U.S. patent Ser. No. 10/716,573 on 2020 Jul. 21. U.S. patent application Ser. No. 16/693,267 was a continuation-in-part of U.S. patent application Ser. No. 15/861,482 filed on 2018 Jan. 3.

U.S. patent application Ser. No. 16/660,929 claimed the priority benefit of U.S. provisional patent application 62/794,609 filed on 2019 Jan. 19. U.S. patent application Ser. No. 16/660,929 claimed the priority benefit of U.S. provisional patent application 62/794,607 filed on 2019 Jan. 19. U.S. patent application Ser. No. 16/660,929 was a continuation-in-part of U.S. patent application Ser. No. 16/541,241 filed on 2019 Aug. 15. U.S. patent application Ser. No. 16/660,929 was a continuation-in-part of U.S. patent application Ser. No. 15/865,822 filed on 2018 Jan. 9 which issued as U.S. patent Ser. No. 10/716,573 on 2020 Jul. 21. U.S. patent application Ser. No. 16/660,929 was a continuation-in-part of U.S. patent application Ser. No. 15/861,482 filed on 2018 Jan. 3.

U.S. patent application Ser. No. 16/541,241 claimed the priority benefit of U.S. provisional patent application 62/794,609 filed on 2019 Jan. 19. U.S. patent application Ser. No. 16/541,241 claimed the priority benefit of U.S. provisional patent application 62/794,607 filed on 2019 Jan. 19. U.S. patent application Ser. No. 16/541,241 claimed the priority benefit of U.S. provisional patent application 62/720,173 filed on 2018 Aug. 21. U.S. patent application Ser. No. 16/541,241 was a continuation-in-part of U.S. patent application Ser. No. 15/865,822 filed on 2018 Jan. 9 which issued as U.S. patent Ser. No. 10/716,573 on 2020 Jul. 21 U.S. patent application Ser. No. 15/865,822 claimed the priority benefit of U.S. provisional patent application 62/589,754 filed on 2017 Nov. 22. U.S. patent application Ser. No. 15/865,822 claimed the priority benefit of U.S. provisional patent application 62/472,519 filed on 2017 Mar. 16. U.S. patent application Ser. No. 15/865,822 was a continuation-in-part of U.S. patent application Ser. No. 15/081,909 filed on 2016 Mar. 27. U.S. patent application Ser. No. 15/865,822 was a continuation-in-part of U.S. patent application Ser. No. 14/526,600 filed on 2014 Oct. 29.

U.S. patent application Ser. No. 15/861,482 claimed the priority benefit of U.S. provisional patent application 62/589,754 filed on 2017 Nov. 22. U.S. patent application Ser. No. 15/861,482 claimed the priority benefit of U.S. provisional patent application 62/472,519 filed on 2017 Mar. 16. U.S. patent application Ser. No. 15/861,482 claimed the priority benefit of U.S. provisional patent application 62/444,860 filed on 2017 Jan. 11. U.S. patent application Ser. No. 15/861,482 was a continuation-in-part of U.S. patent application Ser. No. 15/080,915 filed on 2016 Mar. 25 which issued as U.S. patent Ser. No. 10/028,747 on 2018 Jul. 24. U.S. patent application Ser. No. 15/861,482 was a continuation-in-part of U.S. patent application Ser. No. 14/526,600 filed on 2014 Oct. 29.

U.S. patent application Ser. No. 15/081,909 was a continuation-in-part of U.S. patent application Ser. No. 14/526,600 filed on 2014 Oct. 29. U.S. patent application Ser. No. 15/080,915 was a continuation-in-part of U.S. patent application Ser. No. 14/526,600 filed on 2014 Oct. 29. U.S. patent application Ser. No. 14/526,600 claimed the priority benefit of U.S. provisional patent application 61/897,245 filed on 2013 Oct. 30. U.S. patent application Ser. No. 14/526,600 was a continuation-in-part of U.S. patent application Ser. No. 12/989,048 filed on 2010 Oct. 21 which issued as U.S. Pat. No. 8,974,487 on 2015 Mar. 10. U.S. patent application Ser. No. 12/989,048 claimed the priority benefit of U.S. provisional patent application 61/126,047 filed on 2008 May 1. U.S. patent application Ser. No. 12/989,048 claimed the priority benefit of U.S. provisional patent application 61/126,027 filed on 2008 May 1.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for occluding a cerebral aneurysm.

INTRODUCTION

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain. Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone.

Approximately one-third to one-half of people who suffer a ruptured cerebral aneurysm die within one month of the rupture. Sadly, even among those who survive, approximately one-half suffer significant and permanent deterioration of brain function. Better alternatives for cerebral aneurysm treatment are needed.

REVIEW OF THE RELEVANT ART

U.S. Pat. No. 8,998,947 (Aboytes et al., Apr. 7, 2015, "Devices and Methods for the Treatment of Vascular Defects") discloses an expandable implant that with a first configuration in which the first portion and the second portion are substantially linearly aligned and a second configuration in which the second portion at least partially overlaps the first portion. U.S. patent application 20200205841 (Aboytes et al., Jul. 2, 2020, "Devices, Systems, and Methods for the Treatment of Vascular Defects") and U.S. patent application 20210378681 (Aboytes et al., Dec. 9, 2021, "Devices, Systems, and Methods for the Treatment of Vascular Defects") disclose aneurysm occlusion devices with a first configuration in which a first portion and a second portion are substantially linearly aligned and a second configuration in which the second portion at least partially overlaps the first portion. U.S. patent application 20210244420 (Aboytes et al., Aug. 12, 2021, "Devices and Methods for the Treatment of Vascular Defects") discloses aneurysm occlusion devices with a first configuration in which a first portion and a second portion are substantially linearly aligned and a second configuration in which the second portion at least partially overlaps the first portion.

U.S. patent application 20220031334 (Aguilar, Feb. 3, 2022, "Expandable Devices for Treating Body Lumens") discloses an occlusive device comprising an expandable mesh including an outer mesh and an inner mesh disposed within the outer mesh. U.S. patent application 20230240686 (Ashby et al., Aug. 3, 2023, "Occlusive Devices with Spiral Struts for Treating Vascular Defects") discloses an occlusive device with a plurality of spiral struts. U.S. patent Ser. No. 11/185,335 (Badruddin et al., Nov. 30, 2021, "System for and Method of Treating Aneurysms") discloses an apparatus for treating an aneurysm with an occlusion element disposed on a wire, wherein the occlusion element includes a cover for covering a neck of an aneurysm and an inner anchoring member. U.S. patent application 20170079661 (Bardsley et al., Mar. 23, 2017, "Occlusive Devices"), U.S. patent Ser. No. 10/314,593 (Bardsley et al., Jun. 11, 2019, "Occlusive Devices"), and U.S. patent application 20190269411 (Bardsley et al., Sep. 5, 2019, "Occlusive Devices") disclose an implant with a single- or dual-layer braided body with variable porosity.

U.S. patent application 20110208227 (Becking, Aug. 25, 2011, "Filamentary Devices for Treatment of Vascular Defects") discloses braid-balls for aneurysm occlusion. U.S. patent application 20120316598 (Becking et al., Dec. 13, 2012, "Multiple Layer Filamentary Devices for Treatment of Vascular Defects") and U.S. Pat. No. 9,585,669 (Becking et al., Mar. 17, 2017, "Multiple Layer Filamentary Devices for Treatment of Vascular Defects") disclose braid balls for aneurysm occlusion. U.S. Pat. No. 9,039,726 (Becking, May 26, 2015, "Filamentary Devices for Treatment of Vascular Defects") discloses braid-balls for aneurysm occlusion. U.S. patent application 20200367904 (Becking et al., Nov. 26, 2020, "Multiple Layer Filamentary Devices for Treatment of Vascular Defects") and U.S. patent application 20220022886 (Becking et al., Jan. 27, 2022, "Multiple Layer Filamentary Devices for Treatment of Vascular Defects") disclose braid-balls suitable for aneurysm occlusion.

U.S. patent application 20210228214 (Bowman et al., Jul. 29, 2021, "Devices for Vascular Occlusion") discloses a method of using and delivering an occlusive device. U.S. patent application 20230157696 (Carrillo, May 25, 2023, "Aneurysm Treatment Device and Associated Systems and Methods of Use") discloses an aneurysm treatment device with a tip portion, a body portion, and a base portion. U.S. patent application 20230165587 (Carrillo, Jun. 1, 2023, "Expandable Devices for Treating Body Lumens") discloses an expandable cage with a plurality of mesh stents which receives embolic material therein. U.S. patent application 20220370078 (Chen et al., Nov. 24, 2022, "Vaso-Occlusive Devices") discloses a vaso-occlusive structure made with a gold-platinum-tungsten alloy. U.S. patent application 20230190292 (Choubey et al., Jun. 22, 2023, "Occlusive Devices with Petal-Shaped Regions for Treating Vascular Defects") discloses an occlusive device for treating an aneurysm with a mesh formed from a tubular braid, including a petal-shaped region formed from a flattened section of the tubular braid.

U.S. patent application 20120165919 (Cox et al., Jun. 28, 2012, "Methods and Devices for Treatment of Vascular Defects") and U.S. patent application 20140052233 (Cox et al., Feb. 20, 2014, "Methods and Devices for Treatment of Vascular Defects") disclose an expandable wire body support structure having a low profile radially constrained state, an expanded relaxed state with a substantially spherical or globular configuration having a smooth outer surface, and a porous permeable layer comprising a braided wire occlusive mesh. U.S. patent application 20120283768 (Cox et al., Nov. 8, 2012, "Method and Apparatus for the Treatment of Large and Giant Vascular Defects") discloses the deployment of multiple permeable shell devices within a single vascular defect. U.S. patent Ser. No. 11/179,159 (Cox et al., Nov. 23, 2021, "Methods and Devices for Treatment of Vascular Defects") discloses a device comprising a first hub, a second hub, a support structure having a longitudinal axis, the support structure disposed between the first hub and the second hub, the support structure including a plurality of struts, and a layer of material disposed over the plurality of struts, wherein the first hub is cylindrical and connected to an end of each of the struts of the plurality of struts. U.S. patent application 20230107778 (Cox et al., Apr. 6, 2023, "Methods and Devices for Treatment of Vascular Defects") discloses an expandable body comprising a plurality of elongate filamentary elements each having a first end and a second end, wherein the elements extend from a first end of the device to a second end of the device and back to the first end of the device. U.S. patent application 20110022149 (Cox et al., Jan. 27, 2011, "Methods and Devices for Treatment of Vascular Defects") discloses a device with first ends secured to a first ring and second ends secured to a second ring with the first and second rings being disposed substantially concentric to the longitudinal axis.

U.S. patent application 20200289125 (Dholakia et al., Sep. 17, 2020, "Filamentary Devices Having a Flexible Joint for Treatment of Vascular Defects") discloses an implant with a first permeable shell having a proximal end with a concave or recessed section and a second permeable shell having a convex section that mates with the concave or recessed section. U.S. patent application 20210282785 (Dholakia et al., Sep. 16, 2021, "Devices Having Multiple Permeable Shells for Treatment of Vascular Defects") a device with a plurality of permeable shells connected by a plurality of coils.

U.S. patent applications 20140135811 (Divino et al., May 15, 2014, "Occlusive Devices"), 20140135812 (Divino et al., May 15, 2014, "Occlusive Devices"), 20190282242 (Divino et al., Sep. 19, 2019, "Occlusive Devices"), and 20190290286 (Divino et al., Sep. 26, 2019, "Occlusive Devices") and also U.S. patent Ser. No. 10/327,781 (Divino et al., Jun. 25, 2019, "Occlusive Devices") disclose multiple expandable structures, wherein each of the expandable structures has a unique shape or porosity profile. U.S. patent application 20170281194 (Divino et al., Oct. 5, 2017, "Embolic Medical Devices") discloses an occlusive device with an elongate member having opposing first and second side edges which extend longitudinally along the member and a member width, wherein this member has a collapsed configuration in which the first and second side edges are curled toward each other about a longitudinal axis of the member. U.S. patent application 20190343532 (Divino et al., Nov. 14, 2019, "Occlusive Devices") discloses a device with at least one expandable structure which is adapted to transition from a compressed configuration to an expanded configuration when released into an aneurysm.

U.S. patent application 20200155333 (Franano et al., May 21, 2020, "Ballstent Device and Methods of Use") discloses a rounded, thin-walled, expandable metal structure and a flexible, elongated delivery device. U.S. patent Ser. No. 11/013,516 (Franano et al., May 25, 2021, "Expandable Body Device and Method of Use") discloses a single-lobed, thin-walled, expandable body comprising gold, platinum, or silver. U.S. patent Ser. No. 11/033,275 (Franano et al., Jun. 15, 2021, "Expandable Body Device and Method of Use") discloses devices, designs, methods of manufacturing and using hollow gold structures that can be folded, wrapped, and compressed. U.S. patent application 20210275187 (Franano et al., Sep. 9, 2021, "Expandable Body Device and Method of Use") discloses medical devices comprising a single-lobed, thin-walled, expandable body. U.S. patent application 20190053811 (Garza et al., Feb. 21, 2019, "Flow Attenuation Device") and U.S. patent Ser. No. 11/071,551 (Garza et al., Jul. 27, 2021, "Flow Attenuation Device") disclose an embolic device for treating aneurysms with a desired porosity only at discrete sections.

U.S. patent application 20190365385 (Gorochow et al., Dec. 5, 2019, "Aneurysm Device and Delivery System") and U.S. patent Ser. No. 10/939,915 (Gorochow et al., Mar. 9, 2021, "Aneurysm Device and Delivery System") discloses a braid, wherein translating the braid causes a delivery portion to expand and form a distal sack as well as invert into itself. U.S. patent application 20200113576 (Gorochow et al., Apr. 16, 2020, "Folded Aneurysm Treatment Device and Delivery Method") and U.S. patent application 20210196284 (Gorochow et al., Jul. 1, 2021, "Folded Aneurysm Treatment Device and Delivery Method") disclose an implant having a braided section that folds to form an outer occlusive sack extending across a neck of an aneurysm to engage a wall of the aneurysm from within a sac of the aneurysm and an inner occlusive sack forming a trough nested within the outer occlusive sack. The implant can be closed at one or more of the braid ends to define a substantially enclosed bowl-shaped volume.

U.S. patent Ser. No. 10/653,425 (Gorochow et al., May 19, 2020, "Layered Braided Aneurysm Treatment Device"), U.S. patent application 20200367893 (Xu et al., Nov. 26, 2020, "Layered Braided Aneurysm Treatment Device"), U.S. patent application 20200367898 (Gorochow et al., Nov. 26, 2020, "Layered Braided Aneurysm Treatment Device"), U.S. patent Ser. No. 11/413,046 (Xu et al., Aug. 16, 2022, "Layered Braided Aneurysm Treatment Device"), and U.S. patent application 20200367900 (Pedroso et al., Nov. 26, 2020, "Layered Braided Aneurysm Treatment Device With Corrugations") disclose a tubular braid comprising an open end, a pinched end, and a predetermined shape; wherein, in the predetermined shape, the tubular braid comprises: a first segment extending from the open end to a first inversion, a second segment encircled by the open end such that the second segment is only partially surrounded by the first segment and extending from the first inversion to a second inversion, and a third segment surrounded by the second segment and extending from the second inversion to the pinched end.

U.S. patent application 20210085333 (Gorochow et al., Mar. 25, 2021, "Inverting Braided Aneurysm Treatment System and Method"), U.S. patent Ser. No. 11/278,292 (Gorochow et al., Mar. 22, 2022, "Inverting Braided Aneurysm Treatment System and Method"), and U.S. patent application 20220104829 (Gorochow et al., Apr. 7, 2022, "Inverting Braided Aneurysm Treatment System and Method") disclose a tubular braid with an intrasaccular section, an intravascular section, a pinched section, and a predetermined shape. U.S. patent application 20210169495 (Gorochow et al., Jun. 10, 2021, "Intrasaccular Inverting Braid with Highly Flexible Fill Material") and U.S. patent Ser. No. 11/602,350 (Gorochow et al., Mar. 14, 2023, "Intrasaccular Inverting Braid with Highly Flexible Fill Material") disclose a tubular braided implant which is delivered as a single layer braid, inverted into itself during deployment to form at least two nested sacks and includes additional braid material that can fill the innermost sack.

U.S. patent application 20210186518 (Gorochow et al., Jun. 24, 2021, "Implant Having an Intrasaccular Section and Intravascular Section") and U.S. patent Ser. No. 11/457,926 (Gorochow et al., Oct. 4, 2022, "Implant Having an Intrasaccular Section and Intravascular Section") disclose a tubular braid with an intrasaccular section, an intravascular section, a pinched section, and a predetermined shape. U.S. patent Ser. No. 11/058,430 (Gorochow et al., Jul. 13, 2021, "Aneurysm Device and Delivery System") discloses a braid with a proximal expandable portion for positioning inside an aneurysm and sealing across the neck of the aneurysm. U.S. patent Ser. No. 11/076,861 (Gorochow et al., Aug. 3, 2021, "Folded Aneurysm Treatment Device and Delivery Method") discloses an implant with a fold which defines an annular ridge and a radiopaque marker band. U.S. patent application 20210106338 (Gorochow, Apr. 15, 2021, "Spiral Delivery System for Embolic Braid") discloses a braided implant having a spiral segment. U.S. patent application 20210145449 (Gorochow, May 20, 2021, "Implant Delivery System with Braid Cup Formation") discloses an implant system with an engagement wire, a pull wire, and a braided implant having a distal ring thereon. U.S. patent application 20210169498 (Gorochow, Jun. 10, 2021, "Delivery of Embolic Braid") discloses a braided implant delivery system which attaches a braided implant having a band to a delivery tube, positions the braided implant within an aneurysm, and then releases the band from the delivery tube. U.S. patent Ser. No. 11/051,825 (Gorochow, Jul. 6, 2021, "Delivery System for Embolic Braid") discloses a braided implant which is attached to a releasing component that can be detachably engaged with a delivery tube and a pull wire.

U.S. patent application 20210338250 (Gorochow et al., Nov. 4, 2021, "Intrasaccular Flow Diverter") and U.S. patent Ser. No. 11/523,831 (Gorochow et al., Dec. 13, 2022, "Intrasaccular Flow Diverter") disclose an interior fill braid physically which is inverted over itself to form a proximal inverted end and an opposite free end and a dome braid disposed distally of and secured to the interior fill braid. U.S. patent application 20220202425 (Gorochow et al., Jun. 30, 2022, "Semispherical Braided Aneurysm Treatment System and Method") discloses a tubular braid with three segments and two inversions, one of the three segments extending between the two inversions and forming a sack. U.S. patent application 20210338247 (Gorochow, Nov. 4, 2021, "Double Layer Braid") discloses a double layered braid for treating an aneurysm. U.S. patent Ser. No. 11/583,282 (Gorochow et al., Feb. 21, 2023, "Layered Braided Aneurysm Treatment Device") discloses a method for shaping a tubular braid into a predetermined shape. U.S. patent application 20180070955 (Greene et al., Mar. 15, 2018, "Embolic Containment") discloses a method of treating a neurovascular arteriovenous malformation with liquid embolic and dimethyl sulfoxide.

U.S. patent applications 20150313605 (Griffin, Nov. 5, 2015, "Occlusion Device") and 20190059909 (Griffin, Feb. 28, 2019, "Occlusion Device") and also U.S. patent Ser. No. 10/130,372 (Griffin, Nov. 20, 2018, "Occlusion Device") and U.S. Pat. No. 11,389,174 (Griffin, Jul. 19, 2022, "Occlusion Device") disclose an occlusion device with a substantially solid marker having a proximal end, and a distal end; and a low profile resilient mesh body attached to the distal end of the marker. U.S. patent application 20170156734 (Griffin, Jun. 8, 2017, "Occlusion Device"), U.S. patent Ser. No. 10/285,711 (Griffin, May 14, 2019, "Occlusion Device"), U.S. patent application 20190269414 (Griffin, Sep. 5, 2019, "Occlusion Device"), U.S. patent application 20210153871 (Griffin, May 27, 2021, "Occlusion Device"), and U.S. patent application 20220313274 (Griffin, Oct. 6, 2022, "Occlusion Device") disclose a continuous compressible mesh structure comprising axial mesh carriages configured end to end, wherein each end of each carriage is a pinch point in the continuous mesh structure. U.S. patent Ser. No. 11/471,162 (Griffin, Oct. 18, 2022, "Occlusion Device") discloses an occlusion device for implantation into a body lumen or aneurysm which has a continuous compressible mesh structure comprising axial mesh carriages configured end to end, wherein each end of each carriage is a pinch point in the continuous mesh structure.

U.S. patent application 20200187953 (Hamel et al., Jun. 18, 2020, "Devices, Systems, and Methods for the Treatment of Vascular Defects") discloses a mesh comprising a first end portion, a second end portion, and a length extending between the first and second end portions, and a first lateral edge, a second lateral edge, and a width extending between the first and second lateral edges. U.S. patent application 20210353299 (Hamel et al., Nov. 18, 2021, "Devices, Systems, and Methods for the Treatment of Vascular Defects") discloses a mesh that is curved along its length with an undulating contour across at least a portion of one or both of its length or its width. U.S. patent application 20220330947 (Henkes et al., Oct. 20, 2022, "Implant for the Treatment of Aneurysms") discloses an implant which is rolled up relative to a radial axis in order to form a balled-up configuration.

U.S. patent application 20140358178 (Hewitt et al., Dec. 4, 2014, "Filamentary Devices for Treatment of Vascular Defects"), U.S. Pat. No. 9,078,658 (Hewitt et al., Jul. 14, 2015, "Filamentary Devices for Treatment of Vascular Defects"), U.S. patent application 20160249934 (Hewitt et al., Sep. 1, 2016, "Filamentary Devices for Treatment of Vascular Defects"), U.S. Pat. No. 9,955,976 (Hewitt et al., May 1, 2018, "Filamentary Devices for Treatment of Vascular Defects"), U.S. patent application 20180206849 (Hewitt et al., Jul. 26, 2018, "Filamentary Devices for the Treatment of Vascular Defects"), U.S. patent application 20210007754 (Milhous et al., Jan. 14, 2021, "Filamentary Devices for Treatment of Vascular Defects"), U.S. patent Ser. No. 10/939,914 (Hewitt et al., Mar. 9, 2021, "Filamentary Devices for the Treatment of Vascular Defects"), and U.S. patent application 20210275184 (Hewitt et al., Sep. 9, 2021, "Filamentary Devices for Treatment of Vascular Defects") disclose occlusion devices with permeable shells made of woven braided mesh having a variable mesh density and/or porosity. U.S. patent application 20160249935

(Hewitt et al., Sep. 1, 2016, "Devices for Therapeutic Vascular Procedures"), U.S. patent application 20160367260 (Hewitt et al., Dec. 22, 2016, "Devices for Therapeutic Vascular Procedures"), U.S. Pat. No. 9,629,635 (Hewitt et al., Apr. 25, 2017, "Devices for Therapeutic Vascular Procedures"), and U.S. patent application 20170128077 (Hewitt et al., May 11, 2017, "Devices for Therapeutic Vascular Procedures") disclose a self-expanding resilient permeable shell and a metallic coil secured to the distal end of the permeable shell.

U.S. Pat. No. 9,492,174 (Hewitt et al., Nov. 15, 2016, "Filamentary Devices for Treatment of Vascular Defects"), U.S. patent application 20170095254 (Hewitt et al., Apr. 6, 2017, "Filamentary Devices for Treatment of Vascular Defects"), U.S. patent Ser. No. 10/136,896 (Hewitt et al., Nov. 27, 2018, "Filamentary Devices for Treatment of Vascular Defects"), U.S. patent application 20190192166 (Hewitt et al., Jun. 27, 2019, "Filamentary Devices for Treatment of Vascular Defects"), U.S. patent application 20200289124 (Rangwala et al., Sep. 17, 2020, "Filamentary Devices for Treatment of Vascular Defects"), U.S. patent Ser. No. 10/813,645 (Hewitt et al., Oct. 27, 2020, "Filamentary Devices for Treatment of Vascular Defects"), and U.S. patent application 20210106337 (Hewitt et al., Apr. 15, 2021, "Filamentary Devices for Treatment of Vascular Defects") disclose a self-expanding permeable shell having a radially constrained elongated state configured for delivery within a catheter lumen, an expanded state with a globular and longitudinally shortened configuration relative to the radially constrained state, and a plurality of elongate filaments that are woven together.

U.S. patent application 20190223881 (Hewitt et al., Jul. 25, 2019, "Devices for Therapeutic Vascular Procedures") discloses a self-expanding resilient permeable shell made from elongate resilient filaments with a distal region that extends beyond the distal end of the permeable shell. U.S. patent application 20200289126 (Hewitt et al., Sep. 17, 2020, "Filamentary Devices for Treatment of Vascular Defects"), U.S. patent Ser. No. 11/317,921 (Hewitt et al., May 3, 2022, "Filamentary Devices for Treatment of Vascular Defects"), and U.S. patent application 20220257258 (Hewitt et al., Aug. 18, 2022, "Filamentary Devices for Treatment of Vascular Defects") disclose a permeable shell or mesh with a stiffer proximal portion at the neck of an aneurysm. U.S. patent application 20220192678 (Hewitt et al., Jun. 23, 2022, "Filamentary Devices for Treatment of Vascular Defects") discloses an implant having a first permeable shell having a proximal hub and an open distal end and a second permeable shell having a distal hub and an open proximal end. U.S. patent application 20220257260 (Hewitt et al., Aug. 18, 2022, "Filamentary Devices for Treatment of Vascular Defects") discloses an implant having multiple mesh layers. U.S. patent application 20230114169 (Hewitt et al., Apr. 13, 2023, "Devices for Treatment of Vascular Defects") discloses a permeable woven implant with a radially-constrained state for delivery within a catheter and an expanded state thereafter.

U.S. patent application 20230039246 (Hossan et al., Feb. 9, 2023, "Non-Braided Biodegrable Flow Diverting Device for Endovascular Treatment of Aneurysm and Associated Fabrication Method") discloses a biodegradable flow-diverting device that regulates blood flow into an aneurysmal sac. U.S. patent application 20230263528 (Jones, Aug. 24, 2023, "Intrasacular Flow Diverter and Related Methods") discloses an intrasacular flow diverter with a plurality of wires which are coiled to form a collapsible, substantially spherical frame. U.S. patent application 20230252631 (Kashyap et al., Aug. 10, 2023, "Neural Network Apparatus for Identification, Segmentation, and Treatment Outcome Prediction for Aneurysms") discloses using medical imaging and a neural network to predict outcomes from the potential use of one or more different intrasaccular implant devices. U.S. patent application 20210353300 (Kottenmeier et al., Nov. 18, 2021, "Systems and Methods for Treatment of Defects in the Vasculature") discloses aneurysm occlusion methods and systems including an expandable stent.

U.S. patent application 20230225735 (Kulak et al., Jul. 20, 2023, "Expandable Devices for Treating Body Lumens") discloses a tubular mesh which curves along its longitudinal dimension when implanted in an aneurysm cavity. U.S. patent application 20210137526 (Lee et al., May 13, 2021, "Embolic Devices for Occluding Body Lumens") discloses an embolic device with a first segment forming a first three-dimensional structure, wherein the first three-dimensional structure defines a cavity; and a second segment forming a second three-dimensional structure; wherein the cavity of the first three-dimensional structure is configured to accommodate at least a majority of the second three-dimensional structure. U.S. patent application 20230017150 (Lee et al., Jan. 19, 2023, "Hydrogel Stent and Embolization Device for Cerebral Aneurysm") discloses a hydrogel stent for occluding a cerebral aneurysm.

U.S. patent application 20210128169 (Li et al., May 6, 2021, "Devices, Systems, and Methods for Treatment of Intracranial Aneurysms") and U.S. patent application 20210153872 (Nguyen et al., May 27, 2021, "Devices, Systems, and Methods for Treatment of Intracranial Aneurysms") disclose delivering an occlusive member to an aneurysm cavity and deforming a shape of the occlusive member via introduction of an embolic element to a space between the occlusive member and an inner surface of the aneurysm wall. U.S. patent application 20210128160 (Li et al., May 6, 2021, "Systems and Methods for Treating Aneurysms"), U.S. patent application 20210128167 (Patel et al., May 6, 2021, "Systems and Methods for Treating Aneurysms"), U.S. patent application 20210128168 (Nguyen et al., May 6, 2021, "Systems and Methods for Treating Aneurysms") and disclose delivering an occlusive member (e.g., an expandable braid) to an aneurysm sac in conjunction with an embolic element (e.g., coils, embolic material).

U.S. patent application 20190192168 (Lorenzo et al., Jun. 27, 2019, "Aneurysm Device and Delivery Method") and U.S. patent Ser. No. 10/716,574 (Lorenzo et al., Jul. 21, 2020, "Aneurysm Device and Delivery Method") discloses a self-expanding braid for treating an aneurysm, including a method for inverting and buckling a proximal segment. U.S. patent application 20190223878 (Lorenzo et al., Jul. 25, 2019, "Aneurysm Device and Delivery System") and U.S. patent application 20200397447 (Lorenzo et al., Dec. 24, 2020, "Aneurysm Device and Delivery System") discloses an expandable segment which radially expands inside an outer occlusive sack. U.S. patent application 20210007755 (Lorenzo et al., Jan. 14, 2021, "Intrasaccular Aneurysm Treatment Device with Varying Coatings") discloses an aneurysm intrasaccular implant with coated regions. U.S. patent Ser. No. 10/905,430 (Lorenzo et al., Feb. 2, 2021, "Aneurysm Device and Delivery System") discloses an expandable segment which radially expands inside an outer occlusive sack.

U.S. patent applications 20150272589 (Lorenzo, Oct. 1, 2015, "Aneurysm Occlusion Device") and 20190008522 (Lorenzo, Jan. 10, 2019, "Aneurysm Occlusion Device") and also U.S. patent Ser. No. 11/076,860 (Lorenzo, Aug. 3, 2021, "Aneurysm Occlusion Device") disclose a tubular structure which is constrained by a control ring. U.S. patent application 20180242979 (Lorenzo, Aug. 30, 2018, "Aneurysm Device and Delivery System") and U.S. patent Ser. No. 10/751,066 (Lorenzo, Aug. 25, 2020, "Aneurysm Device and Delivery System") disclose a self-expanding braided tubular member. U.S. patent application 20200375606 (Lorenzo, Dec. 3, 2020, "Aneurysm Method and System") discloses a braided implant which is invertible about the distal implant end. U.S. patent application 20210177429 (Lorenzo, Jun. 17, 2021, "Aneurysm Method and System") discloses a vaso-occlusive device with at least two nested sacks. U.S. patent Ser. No. 11/123,077 (Lorenzo et al., Sep. 21, 2021, "Intrasaccular Device Positioning and Deployment System") discloses implant deployment systems including a braided implant that can be detachably attached to a delivery tube by an expansion ring. U.S. patent application 20210330331 (Lorenzo, Oct. 28, 2021, "Aneurysm Occlusion Device") and U.S. patent Ser. No. 11/154,302 (Lorenzo et al., Oct. 26, 2021, "Aneurysm Occlusion Device") disclose an occlusion device with a substantially annular body disposed on the proximal end region of the device. U.S. patent application 20200038034 (Maguire et al., Feb. 6, 2020, "Vessel Occluder") discloses a vessel occluder with an expandable mesh portion having a flexible membrane that expands within a cavity of the expandable mesh portion.

U.S. patent application 20130245667 (Marchand et al., Sep. 19, 2013, "Filamentary Devices and Treatment of Vascular Defects") discloses a self-expanding resilient permeable shell wherein filaments are bundled and secured to each other at a proximal end. U.S. patent application 20160249937 (Marchand et al., Sep. 1, 2016, "Multiple Layer Filamentary Devices for Treatment of Vascular Defects"), U.S. Pat. No. 9,918,720 (Marchand et al., Mar. 20, 2018, "Multiple Layer Filamentary Devices for Treatment of Vascular Defects"), and U.S. patent Ser. No. 10/238,393 (Marchand et al., Mar. 26, 2019, "Multiple Layer Filamentary Devices for Treatment of Vascular Defects") disclose a permeable shell and an inner structure configured to occlude blood flow. U.S. patent application 20180000489 (Marchand et al., Jan. 4, 2018, "Filamentary Devices for Treatment of Vascular Defects") discloses a self-expanding resilient permeable shell having a plurality of elongate resilient filaments with a woven structure. U.S. patent Ser. No. 10/610,231 (Marchand et al., Apr. 7, 2020, "Filamentary Devices for Treatment of Vascular Defects") discloses a self-expanding resilient permeable shell with a plurality of elongate resilient filaments with a woven structure, wherein the plurality of filaments includes small filaments and large filaments, and wherein the small filaments have a transverse dimension which is smaller than the transverse dimension of the large filaments. U.S. patent application 20200281603 (Marchand et al., Sep. 10, 2020, "Filamentary Devices for Treatment of Vascular Defects") discloses a permeable shell including a really swell polymer.

U.S. patent Ser. No. 11/517,321 (Mauger et al., Dec. 6, 2022, "System and Methods for Embolized Occlusion of Neurovascular Aneurysms") discloses an occlusion device with a reinforcing portion with no porosity. U.S. patent Ser. No. 11/589,872 (Mauger, Feb. 28, 2023, "Vascular Occlusion Devices Utilizing Thin Film Nitinol Foils") discloses an implantable occlusion device wherein mesh components are wrapped around a support structure and slot that enables a disc to be wrapped around the support structure with overlapping portions. U.S. patent application 20230285031 (Mayer et al, Sep. 14, 2023, "Device for Restricting Blood Flow to Aneurysms") discloses a non-occlusive device with a coilable section and a docking section. U.S. patent application 20220249098 (Milhous et al., Aug. 11, 2022, "Filamentary Devices for Treatment of Vascular Defects") discloses a permeable implant with a plurality of scaffolding filaments. U.S. patent application 20230039773 (Monstadt et al., Feb. 9, 2023, "Implant for Treating Aneurysms") discloses an implant which is preset to a specific structure.

U.S. patent Ser. No. 11/426,175 (Morita et al., Aug. 30, 2022, "Expansile Member") discloses an occlusive system comprising: a catheter; a shell deliverable through the catheter, a delivery pusher detachably connected to the shell and configured to navigate the shell through the catheter, wherein the shell has a globular shaped portion. U.S. patent application 20210129275 (Nguyen et al., May 6, 2021, "Devices, Systems, and Methods for Treating Aneurysms") discloses methods of manufacturing an occlusive device including conforming a mesh to a forming assembly and setting a shape of the mesh based on the forming assembly. U.S. patent application 20210275779 (Northrop, Sep. 9, 2021, "Actuating Elements for Bending Medical Devices") discloses an actuating element causes a tube to bend. U.S. patent Ser. No. 11/498,165 (Patel et al., Nov. 15, 2022, "Systems and Methods for Treating Aneurysms") discloses an occlusive implant with a conduit which receives a liquid embolic.

U.S. patent application 20210346032 (Patterson et al., Nov. 11, 2021, "Devices for Treatment of Vascular Defects") discloses an expandable stent for placement in a parent vessel proximal, near, or adjacent an aneurysm. U.S. patent Ser. No. 11/607,226 (Pedroso et al., Mar. 21, 2023, "Layered Braided Aneurysm Treatment Device with Corrugations") discloses an implant with a proximal inversion and two segments. U.S. patent Ser. No. 11/058,431 (Pereira et al., Jul. 13, 2021, "Systems and Methods for Treating Aneurysms") discloses an inverted mesh tube having an outer layer and an inner layer, wherein the outer layer transitions to the inner layer at an inversion fold located at or adjacent to the distal end of the occlusion element. U.S. patent application 20170258473 (Plaza et al., Sep. 14, 2017, "Systems and Methods for Delivery of Stents and Stent-Like Devices") discloses an elongate tubular member having a lumen, an expandable stent, and a delivery device which is placed in a cerebral vessel adjacent to an aneurysm.

U.S. patent applications 20060155323 (Porter et al., Jul. 13, 2006, "Intra-Aneurysm Devices") and 20190298379 (Porter et al., Oct. 3, 2019, "Intra-Aneurysm Devices") and also U.S. patent Ser. No. 10/265,075 (Porter et al., Apr. 23, 2019, "Intra-Aneurysm Devices") disclose an occlusive device having a neck and a dome. U.S. patent application 20210052279 (Porter et al., Feb. 25, 2021, "Intra-Aneurysm Devices") discloses a device including an upper member that sits against the dome of an aneurysm, a lower member that sits in the neck of the aneurysm, and a means of adjusting the overall dimensions of the device. U.S. patent application 20210128165 (Pulugurtha et al., May 6, 2021, "Systems and Methods for Treating Aneurysms") and U.S. patent Ser. No. 11/305,387 (Pulugurtha et al., Apr. 19, 2022, "Systems and Methods for Treating Aneurysms") disclose a distal conduit coupled to an occlusive member with a first lumen extending therethrough and a proximal conduit with a second lumen extending therethrough.

U.S. patent application 20220039804 (Rangwala et al., Feb. 10, 2022, "Flow-Diverting Implant and Delivery Method") discloses a saddle-shaped braided mesh diverter that covers the neck of an aneurysm. U.S. patent Ser. No. 11/559,309 (Rangwala et al., Jan. 24, 2023, "Filamentary Devices for Treatment of Vascular Defects") discloses a permeable implant whose proximal portion is stiffer. U.S. patent application 20230277184 (Rashidi et al., Sep. 7, 2023, "Occlusive Devices with Thrombogenic Inserts") discloses an expandable mesh which spans a neck of the aneurysm with an insert configured to promote thrombosis.

U.S. patent application 20170079662 (Rhee et al., Mar. 23, 2017, "Occlusive Devices") discloses an implant with a frame and a mesh component, wherein the mesh component has a first porosity and the frame has a second porosity. U.S. patent Ser. No. 10/478,194 (Rhee et al., Nov. 19, 2019, "Occlusive Devices") and U.S. patent application 20200038032 (Rhee et al., Feb. 6, 2020, "Occlusive Devices") disclose an implant with a frame and a mesh component, wherein the mesh component has a first porosity and the frame has a second porosity. U.S. patent application 20210128162 (Rhee et al., May 6, 2021, "Devices, Systems, and Methods for Treatment of Intracranial Aneurysms") discloses introduction of an embolic element to a space between an occlusive member and an inner surface of the aneurysm wall.

U.S. patent application 20140330299 (Rosenbluth et al., Nov. 6, 2014, "Embolic Occlusion Device and Method"), U.S. patent application 20180303486 (Rosenbluth et al., Oct. 25, 2018, "Embolic Occlusion Device and Method"), and U.S. patent application 20210259699 (Rosenbluth et al., Aug. 26, 2021, "Embolic Occlusion Device and Method") disclose an occlusion device with a tubular braided member having a first end and a second end and extending along a longitudinal axis, the tubular braided member having a repeating pattern of larger diameter portions and smaller diameter portions arrayed along the longitudinal axis. U.S. patent applications 20160022445 (Ruvalcaba et al., Jan. 28, 2016, "Occlusive Device") and 20190343664 (Ruvalcaba et al., Nov. 14, 2019, "Occlusive Device") U.S. patent Ser. No. 11/389,309 (Ruvalcaba et al., Jul. 19, 2022, "Occlusive Device") disclose an aneurysm embolization device having a single, continuous piece of material that is shape set into a plurality of distinct structural components.

U.S. patent application 20020169473 (Sepetka et al., Nov. 14, 2002, "Devices and Methods for Treating Vascular Malformations") discloses a device with a primary coil to provide structural integrity and secondary windings to fill interstitial spaces. U.S. patent application 20080281350 (Sepetka et al., Nov. 13, 2008, "Aneurysm Occlusion Devices") discloses an implantable occlusion device with a concave or cup-shaped shape after implantation. U.S. Pat. No. 8,597,320 (Sepetka et al., Dec. 3, 2013, "Devices and Methods for Treating Vascular Malformations") discloses a method of filling an aneurysm by advancing a device with a proximal collar and a distal collar through a vascular system and then positioning the device within an aneurysm. U.S. patent application 20140200607 (Sepetka et al., Jul. 17, 2014, "Occlusive Device"), U.S. patent application 20190274691 (Sepetka et al., Sep. 12, 2019, "Occlusive Device"), and U.S. patent Ser. No. 11/045,203 (Sepetka et al., Jun. 29, 2021, "Occlusive Device") disclose multiple sequentially deployed occlusive devices that are connected together to create an extended length. U.S. patent application 20210282784 (Sepetka et al., Sep. 16, 2021, "Occlusive Device") discloses a device comprising a plurality of braided wires and an embolic coil.

U.S. patent application 20170224350 (Shimizu et al., Aug. 10, 2017, "Devices for Vascular Occlusion"), U.S. patent Ser. No. 10/729,447 (Shimizu et al., Aug. 4, 2020, "Devices for Vascular Occlusion"), U.S. patent application 20200323534 (Shimizu et al., Oct. 15, 2020, "Devices for Vascular Occlusion"), U.S. patent Ser. No. 10/980,545 (Bowman et al., Apr. 20, 2021, "Devices for Vascular Occlusion"), U.S. patent application 20210228214 (Bowman et al., Jul. 29, 2021, "Devices for Vascular Occlusion"), and U.S. patent application 20210228214 (Bowman et al., Jul. 29, 2021, "Devices for Vascular Occlusion") disclose an occlusive device, an occlusive device delivery system, method of using, method of delivering an occlusive device, and method of making an occlusive device to treat various intravascular conditions. U.S. patent application 20230031965 (Sivapatham, Feb. 2, 2023, "Intrasaccular Stent Device for Aneurysm Treatment") discloses a system for treating an aneurysm in a blood vessel comprising a catheter, a guidewire, a delivery wire, an intrasaccular stent/retaining device removably attached to the delivery wire, and endovascular coiling.

U.S. patent application 20200305886 (Soto Del Valle et al, Oct. 1, 2020, "Aneurysm Treatment Device") and U.S. patent application 20220225997 (Soto Del Valle et al., Jul. 21, 2022, "Aneurysm Treatment Device") disclose a device with an expandable sack with a free open end and an elongated looping portion. U.S. patent application 20200305885 (Soto Del Valle et al, Oct. 1, 2020, "Aneurysm Treatment Device") discloses an occlusion device that expands to form a cup shape within an aneurysm sac. U.S. patent application 20200375607 (Soto Del Valle et al., Dec. 3, 2020, "Aneurysm Device and Delivery System") discloses a method of expanding mesh segments to form an outer occlusive sack and an inner occlusive sack. U.S. patent Ser. No. 11/337,706 (Soto Del Valle et al., May 24, 2022, "Aneurysm Treatment Device") discloses an implant having an elongated portion and an expandable braided sack portion.

U.S. patent application 20210282789 (Vu et al., Sep. 16, 2021, "Multiple Layer Devices for Treatment of Vascular Defects") discloses a first permeable shell and a second permeable shell, where the second permeable shell sits within an interior cavity of the first permeable shell. U.S. patent application 20220175389 (Wallace et al., Jun. 9, 2022, "Vaso-Occlusive Devices Including a Friction Element") discloses a vaso-occlusive implant with a friction element between a soft braided member and a coil. U.S. patent application 20200187952 (Walsh et al., Jun. 18, 2020, "Intrasaccular Flow Diverter for Treating Cerebral Aneurysms") and U.S. patent application 20220151632 (Walsh et al., May 19, 2022, "Intrasaccular Flow Diverter for Treating Cerebral Aneurysms") disclose a stabilizing frame with two parts, the first part sized to anchor within the sac of the aneurysm and the exterior part sized to anchor against a region of the blood vessel wall adjacent the aneurysm neck.

U.S. patent application 20200029973 (Walzman, Jan. 30, 2020, "Mash Cap for Ameliorating Outpouchings") discloses an embolic device comprising a control element, a catheter element, a delivery microcatheter hypotube, a detachment element, a mesh disc, a distal opening, and at least one attached extension arm. U.S. patent application 20200405347 (Walzman, Dec. 31, 2020, "Mesh Cap for Ameliorating Outpouchings") discloses a self-expandable occluding device which covers the neck of an outpouching and serves as a permanent embolic plug. U.S. patent Ser. No. 10/398,441 (Warner et al., Sep. 3, 2019, "Vascular Occlusion") discloses a vascular treatment system with a containment device, a pusher, and a stopper ring. U.S. patent Ser. No. 11/166,731 (Wolfe et al., Nov. 9, 2021, "Systems and Methods for Treating Aneurysms") discloses an inverted mesh tube having an outer layer and an inner layer, the outer layer transitioning to the inner layer at an inversion fold.

U.S. patent application 20200367906 (Xu et al., Nov. 26, 2020, "Aneurysm Treatment With Pushable Ball Segment") and U.S. patent application 20230016312 (Xu et al., Jan. 19, 2023, "Aneurysm Treatment with Pushable Implanted Braid") disclose a braided implant with a retractable dual proximal layer. U.S. patent application 20220087681 (Xu et al., Mar. 24, 2022, "Inverting Braided Aneurysm Implant with Dome Feature") discloses an implant with a dome feature configured to press into aneurysm walls near the aneurysm's dome and facilitate securement of the braid across the aneurysm's neck. U.S. patent Ser. No. 11/497,504 (Xu et al., Nov. 15, 2022, "Aneurysm Treatment with Pushable Implanted Braid") discloses a braided implant with a retractable dual proximal layer. U.S. patent Ser. No. 11/596,412 (Xu et al., Mar. 7, 2023, "Aneurysm Device and Delivery System") discloses a braid with a proximal portion which goes across an aneurysm neck and an expandable distal portion. U.S. patent application 20230061363 (Yee et al., Mar. 2, 2023, "Embolic Device with Improved Neck Coverage") discloses an embolic device with a flexible structure which has a series of alternating narrow portions and link portions.

U.S. patent application 20200367896 (Zaidat et al., Nov. 26, 2020, "Systems and Methods for Treating Aneurysms") discloses an apparatus for treating an aneurysm in a blood vessel with a first tubular mesh having a first end and a second end coupled together at a proximal end of the occlusion element. U.S. patent Ser. No. 11/202,636 (Zaidat et al., Dec. 21, 2021, "Systems and Methods for Treating Aneurysms"), U.S. patent application 20220022884 (Wolfe et al., Jan. 27, 2022, "Systems and Methods for Treating Aneurysms"), and U.S. patent application 20220211383 (Pereira et al., Jul. 7, 2022, "Systems and Methods for Treating Aneurysms") disclose an apparatus for treating an aneurysm including an occlusion element configured to be releasably coupled to an elongate delivery shaft and a distal end, a proximal end, and a longitudinal axis extending between the distal end and the proximal end. U.S. patent application 20220054141 (Zaidat et al., Feb. 24, 2022, "Systems and Methods for Treating Aneurysms") discloses an apparatus for treating an aneurysm in a blood vessel with a first tubular mesh having a first end and a second end coupled together at a proximal end of the occlusion element.

SUMMARY OF THE INVENTION

An intrasacular aneurysm occlusion device can have nested proximal and distal meshes, wherein the proximal mesh covers an aneurysm neck and the distal mesh is expanded to fill the aneurysm sac by the insertion of embolic members and/or material into the distal mesh. The distal mesh is more flexible and less stiff than the proximal mesh, enabling it to conform to the walls of even an irregularly-shaped aneurysm sac when expanded.

In an example, a proximal mesh can be bowl-shaped or torus-shaped with a central opening, column, and/or hub through which embolic members and/or material is inserted. In an example, proximal and distal meshes can be created separately and then attached together. In another example, proximal and distal meshes can be portions, sections, and/or lobes of the same mesh structure which has been radially-constrained, folded, inverted, and/or everted.

BRIEF INTRODUCTION TO THE FIGURES

Figure 16:
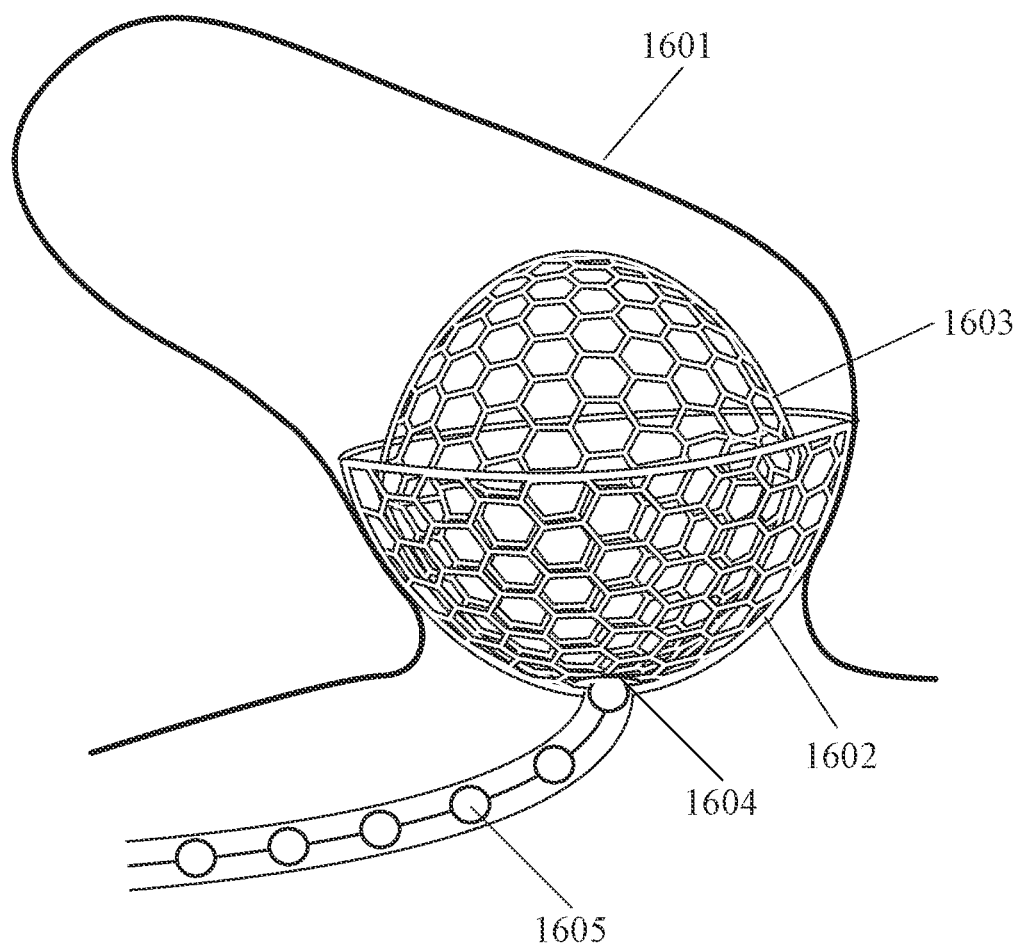
Figure 17:
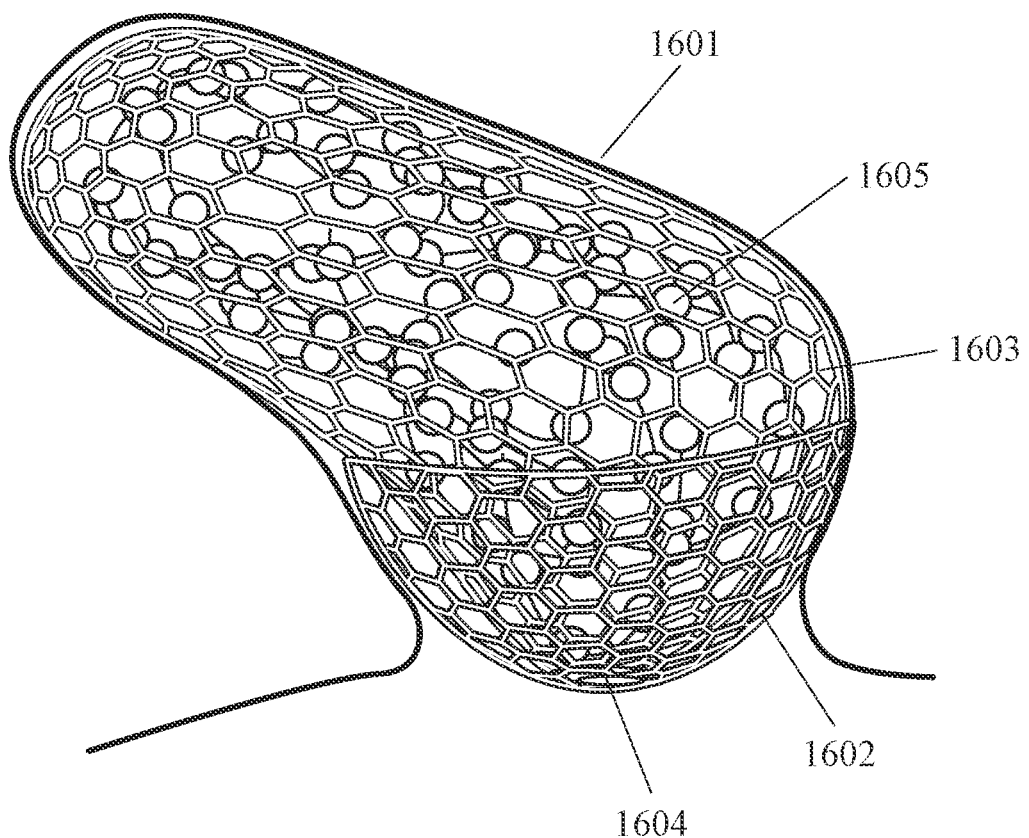

FIGS. 16 and 17 show side views, at two different times, of an intrasacular aneurysm occlusion device comprising a proximal mesh, a distal mesh, an opening in the proximal mesh, and embolic members and/or embolic material which is inserted through the opening into the distal mesh, wherein insertion of the embolic members and/or embolic material into the distal mesh expands the distal mesh to fill the aneurysm sac.

DETAILED DESCRIPTION OF THE FIGURES

In an example, an intrasacular aneurysm occlusion device can comprise: a proximal mesh (e.g. mesh, net, stent, or shell) which is configured to be inserted and expanded within an aneurysm sac; a distal mesh (e.g. mesh, net, stent, or shell) which is configured to be inserted and expanded within the aneurysm sac; an opening in the proximal mesh; and embolic members and/or embolic material which is inserted through the opening into the distal mesh, wherein insertion of the embolic members and/or embolic material into the distal mesh expands the distal mesh to fill the aneurysm sac. The distal mesh is flexible, so that after it has been expanded by insertion of the embolic members and/or material, it conforms to the shape of even an irregularly-shaped aneurysm sac.

In an example, an intrasacular aneurysm occlusion device can comprise: a first mesh or net which is configured to be inserted and expanded within an aneurysm sac, wherein the first mesh or net has a first proximal-to-distal length, wherein the first mesh or net has a first stiffness level, and wherein the first mesh or net has a first elasticity level; and a second mesh or net which is in contact with a proximal portion of the first mesh or net, wherein the second mesh or net has a second proximal-to-distal length, wherein the second mesh or net has a second stiffness level, wherein the second mesh or net has a second elasticity level, wherein the second proximal-to-distal length is less than the first proximal-to-distal length, and wherein the second stiffness level is greater than the first stiffness level and/or the second elasticity level is less than the first elasticity level.

In an example, the second mesh or net can be inside the first mesh or net. In an example, the first mesh or net can be inside the second mesh or net. In an example, the device can further comprise a central proximal opening in one or both meshes or nets through which embolic material is inserted. In an example, the first mesh or net can have a globular shape and the second mesh or net can have a bowl shape. In an example, the first mesh or net and the second mesh or net can be separate structures which are attached to each other. In an example, the first mesh or net and the second mesh or net can be portions, sections, and/or lobes of the same mesh structure which has been radially-constrained, folded, inverted, and/or everted.

In another example, an intrasacular aneurysm occlusion device can comprise: a globular outer mesh or net which is configured to be inserted and expanded within an aneurysm sac; an inner mesh or net which is inside the outer mesh or net; and a central column along a proximal-to-distal longitudinal axis of the inner mesh or net.

In an example, an inner mesh or net can have a toroidal shape. In an example, the central column can comprise a central lumen, opening, or hole in a toroidal shaped inner mesh or net. In an example, embolic material can be inserted through the central column. In an example, the outer mesh or net and the inner mesh or net can be separate structures which are attached to each other. In an example, the outer mesh or net and the inner mesh or net can be portions, sections, and/or lobes of the same structure which has been radially-constrained, folded, inverted, and/or everted.

In another example, an intrasacular aneurysm occlusion device can comprise: a multi-layer or multi-wall bowl-shaped mesh or net which is configured to be inserted and expanded within an aneurysm sac so as to cover the aneurysm neck, wherein the mesh or net further comprises: a proximal layer or wall which is configured to face toward the aneurysm neck; a distal layer or wall which is configured to face toward the aneurysm dome; and a thrombogenic member which is inserted between the proximal layer or wall and the distal layer or wall.

In an example, the proximal layer or wall can have a hemispherical, hemiellipsoidal, or half-toroidal shape. In an example, the distal layer or wall can have a hemispherical, hemi-ellipsoidal, frustal, funnel, and/or hyperboloidal shape. In an example, a gap between the proximal layer or wall and the distal layer or wall can be narrower toward both the center and the circumference of the mesh or net. In an example, a gap between the proximal layer or wall and the distal layer or wall can be narrower only toward the circumference of the mesh or net. In an example, the proximal layer or wall and the distal layer or wall can be separate structures which are attached to each other. In an example, the proximal layer or wall and the distal layer or wall can be portions, sections, and/or lobes of the same structure which has been radially-constrained, folded, inverted, and/or everted.

Figure 1:
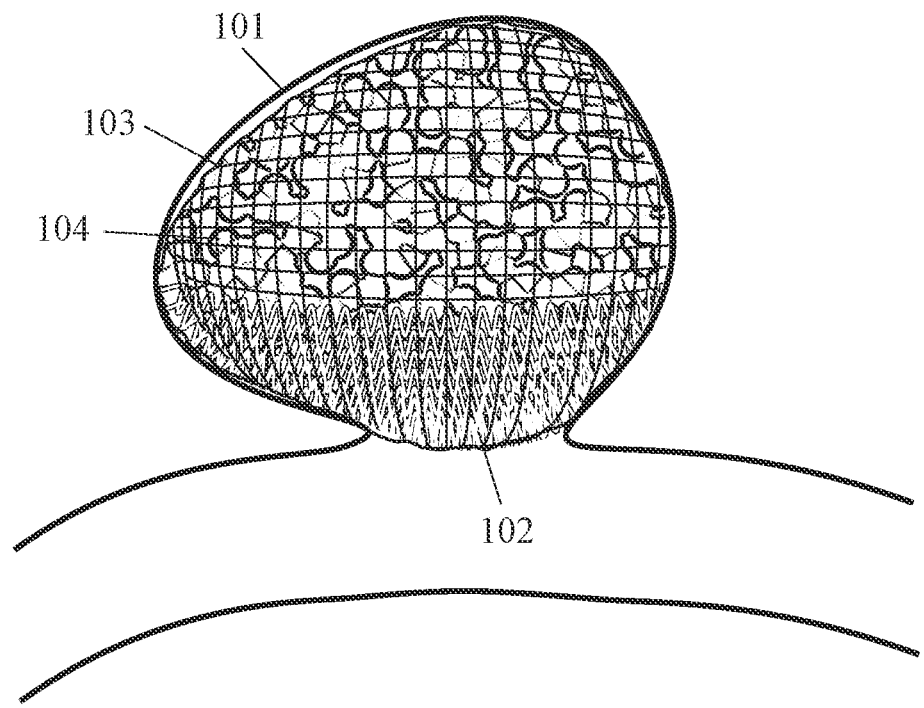
FIG. 1 shows an aneurysm occlusion device with a resilient wider-than-neck portion and a flexible sac-filling portion.

FIG. 1 shows an example of an intrasacular aneurysm occlusion device comprising: a resilient wider-than-neck portion 102 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 103 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 104 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability.

In this example, a resilient wider-than-neck portion of the device and a flexible sac-filling portion of the device are parts of the same convex structure. The resilient wider-than-neck portion is the proximal part of this structure and the flexible sac-filling portion is the distal part of this device. In an example, the resilient wider-than-neck portion can comprise the proximal surface of the device and the flexible sac-filling portion can comprise non-proximal surfaces (e.g. distal and peripheral) of the device. In an example, an intrasacular aneurysm occlusion device need not be of uniform tensile strength, flexibility, plasticity, or elasticity. It can be more flexible at one or more locations. Accordingly, in this example, although the resilient wider-than-neck and flexible sac-filling portions of this device are both part of the same structure, they differ in flexibility and porosity. The flexible sac-filling portion is more flexible and more porous than the resilient wider-than-neck portion. Relevant example variations discussed elsewhere in this disclosure or priority-linked disclosures can also be applied to this example.

Figure 2:
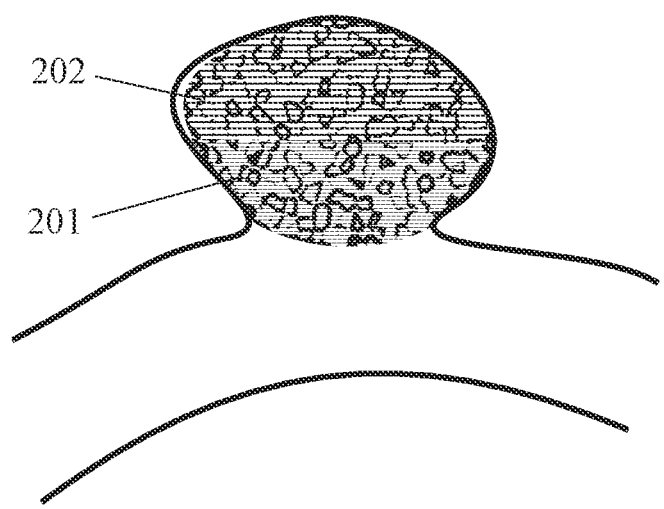
FIG. 2 shows an aneurysm occlusion device with a high-flexibility distal portion and a low-flexibility proximal portion.

FIG. 2 shows an example of an intrasacular aneurysm occlusion device comprising: an intrasacular arcuate expandable member with a high-flexibility distal portion 202 and a low-flexibility proximal portion 201. In an example, an intrasacular arcuate expandable member can have a distal portion with a first level of flexibility and a proximal portion with a second level of flexibility, wherein the second level is less than the first level. In an example, an intrasacular arcuate expandable member can have a distal portion with a first level of elasticity and a proximal portion with a second level of elasticity, wherein the second level is less than the first level. In an example, the high-flexibility distal portion of an arcuate expandable member can have an irregular expanded arcuate three-dimensional shape which conforms to the walls of an irregularly-shaped aneurysm sac, while the low-flexibility proximal portion prevents the expandable member from protruding out of the aneurysm sac. Relevant example variations discussed elsewhere in this disclosure or priority-linked disclosures can also be applied to this example.

Figure 3:
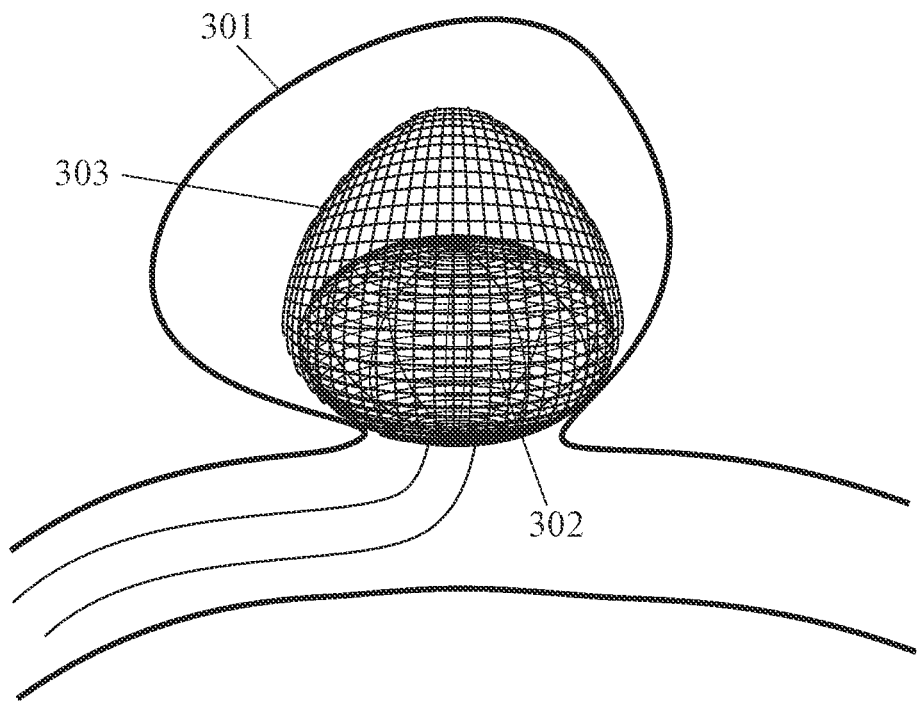
FIG. 3 shows an aneurysm occlusion device with a distal mesh and a proximal mesh, wherein the proximal mesh is stiffer than the first mesh, the proximal mesh is inside the distal mesh, and the distal mesh is ellipsoidal.

FIG. 3 shows an example of a intrasacular aneurysm occlusion device comprising: a resilient wider-than-neck portion 302 (such as a stent or neck bridge) of a device with a first (constrained) configuration as it is transported to an aneurysm sac 301 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 303 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability.

In this example, a resilient wider-than-neck portion expands within the aneurysm sac to an ellipsoidal shape with a width that is greater than the width of the aneurysm neck. In an example, the expanded shape of the wider-than-neck portion can be selected from the group consisting of: apple shape; bowl shape; compress-sphere shape; cylinder; disk; doughnut shape; egg shape; ellipsoid; Frisbee™ shape; frustum; hourglass shape; oval; peanut shape; pear shape; pumpkin shape; ring shape; Saturn shape; sphere; tire shape; and torus.

The flexible sac-filling portion of the device shown in FIG. 3 can comprise a first mesh or net with a first proximal-to-distal length, a first stiffness level, and a first elasticity level. The resilient wider-than-neck portion of the device shown in FIG. 3 can comprise a second mesh or net with a second proximal-to-distal length, a second stiffness level, and a second elasticity level. As shown in FIG. 3, the second proximal-to-distal length can be less than the first proximal-to-distal length. As discussed above, the second elasticity level can be less than the first elasticity level. Since stiffness can be the opposite of elasticity and/or flexibility, the second stiffness level can be greater than the first stiffness level.

As discussed above in accordance with the example in FIG. 3, an intrasacular aneurysm occlusion device can comprise: a first mesh or net (e.g. mesh, net, shell, or stent) which is configured to be inserted and expanded within an aneurysm sac, wherein the first mesh or net has a first proximal-to-distal length, wherein the first mesh or net has a first stiffness level, and wherein the first mesh or net has a first elasticity level; and a second mesh or net (e.g. mesh, net, shell, or stent) which is in contact with a proximal portion of the first mesh or net, wherein the second mesh or net has a second proximal-to-distal length, wherein the second mesh or net has a second stiffness level, wherein the second mesh or net has a second elasticity level, wherein the second proximal-to-distal length is less than the first proximal-to-distal length, and wherein the second stiffness level is greater than the first stiffness level and/or the second elasticity level is less than the first elasticity level.

As shown in FIG. 3, the second mesh or net can be inside the first mesh or net. As shown in FIG. 3, the second mesh or net can be inside the first mesh or net and in contact with a proximal portion of the first mesh or net. In an example, the first mesh or net and the second mesh or net can be connected at a proximal hub. Alternatively, the first mesh or net and the second mesh or net can be connected at a distal hub. In an example, there can be a central proximal opening in one or both meshes or nets through which embolic material can be inserted. In an example, the first mesh or net can have a generally globular (e.g. spherical, oblate spherical, ellipsoidal or toroidal) shape and the second mesh or net can have a bowl (e.g. hemispherical, hemi-ellipsoidal, or half-toroidal) shape.

In an example, filaments (e.g. wires or strands) comprising the first mesh or net can have a first thickness and filaments (e.g. wires or strands) comprising the second mesh or net can have a second thickness, wherein the second thickness is greater than the first thickness. In an example, the second proximal-to-distal length can be between 25% and 75% of the first proximal-to-distal length. In an example, the second mesh or net can be in contact with only the proximal third of the first mesh or net. In an example, the second proximal-to-distal length can be between 20% and 40% of the first proximal-to-distal length. In this example, the first mesh or net and the second mesh or net are separate structures which are connected. In an alternative example, the first mesh or net and the second mesh or net can be portions, sections, and/or lobes of the same (tubular) mesh structure which has been radially-constrained, inverted, and/or everted.

In an example, a proximal portion of an intrasacular occlusion device can comprise a resilient wider-than-neck portion with a first softness level and a distal portion of this intrasacular occlusion device can comprise a flexible sac-filling portion with a second softness level, wherein the second level is greater than the first level. In an example, the proximal portion of an intrasacular occlusion device can comprise a resilient wider-than-neck portion with a first stiffness level and a distal portion of this intrasacular occlusion device can comprise a flexible sac-filling portion with a second stiffness level, wherein the second level is less than the first level.

In an example, a proximal surface of a flexible sac-filling portion of a device can have a first thickness; the distal surface of a flexible sac-filling portion of a device can have a second thickness; and the first thickness can be greater than the second thickness. In an example, a proximal part of a flexible sac-filling portion can have a first width and a distal part of the flexible sac-filling portion can have a second width, wherein the second width is greater than the first width. In an example, different areas of flexible sac-filling portion can have different levels of resiliency.

In an example, a resilient wider-than-neck portion and a flexible sac-filling portion can be different parts of the same continuous intrasacular occlusion device, but have different properties. In an example, the proximal portion of this intrasacular occlusion device can comprise a resilient wider-than-neck portion with a first density level and a distal portion of this intrasacular occlusion device can comprise a flexible sac-filling portion with a second density level, wherein the second level is less than the first level. In an example, the proximal portion of an intrasacular occlusion device can comprise a resilient wider-than-neck portion with a first elasticity level and a distal portion of this intrasacular occlusion device can comprise a flexible sac-filling portion with a second elasticity level, wherein the second level is greater than the first level. In an example, the proximal portion of an intrasacular occlusion device can comprise a resilient wider-than-neck portion with a first flexibility level and a distal portion of this intrasacular occlusion device can comprise a flexible sac-filling portion with a second flexibility level, wherein the second level is greater than the first level.

In an example, a resilient wider-than-neck portion of a device can have a first porosity level and a flexible sac-filling portion can have a second porosity level, wherein the second level is greater than the first level. In an example, a resilient wider-than-neck portion of a device can have a first rigidity level and a flexible sac-filling portion can have a second rigidity level, wherein the second level is less than the first level. In an example, a flexible sac-filling portion of a device can be larger in its second (expanded) configuration than the size of the resilient wider-than-neck portion of a device in its second (expanded) configuration. In an example, a resilient wider-than-neck portion of a device can have a first softness level and a flexible sac-filling portion can have a second softness level, wherein the second level is greater than the first level. In an example, a resilient wider-than-neck portion of a device can have a first stiffness level and a flexible sac-filling portion can have a second stiffness level, wherein the second level is less than the first level. In an example, a flexible sac-filling portion of a device can be larger in its second (expanded) configuration than a resilient wider-than-neck portion of a device in its second (expanded) configuration.

In an example, an aneurysm occlusion device can comprise: (1) a resilient wider-than-neck portion of the device; wherein the resilient wider-than-neck portion has a first configuration while it is being transported to an aneurysm sac; wherein the resilient wider-than-neck portion has a second configuration after it has been delivered into and expanded within the aneurysm sac; wherein the resilient wider-than-neck portion in its second configuration has a width in a plane which is substantially parallel to the circumference of the neck of the aneurysm sac and this width is greater than the diameter of the neck of the aneurysm sac; and wherein the resilient wider-than-neck in its second configuration has a first level of resiliency, rigidity, and/or stiffness; and (2) a flexible sac-filling portion of the device; wherein the flexible sac-filling portion has a first configuration while it is being transported to an aneurysm sac; wherein the flexible sac-filling portion has a second configuration after it has been delivered into and expanded within the aneurysm sac; wherein the flexible sac-filling portion is expanded from its first configuration to its second configuration by the insertion of embolic members into the flexible sac-filling portion; and wherein the flexible sac-filling portion in its second configuration has a second level of resiliency, rigidity, and/or stiffness which is less than the first level of resiliency, rigidity, and/or stiffness.

In an example, an aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a proximal location and a second tensile strength at a distal location, and wherein the second tensile strength is less than the first tensile strength. In an example, an aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a proximal location and a second elasticity at a distal location, and wherein the second elasticity is greater than the first elasticity.

In an example, an aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a proximal location and a second flexibility at a distal location, and wherein the second flexibility is greater than the first flexibility. In an example, an aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a proximal location and a second porosity at a distal location, and wherein the second porosity is greater than the first porosity. Relevant embodiment variations discussed elsewhere in this disclosure or in priority-linked disclosures can also apply to this example.

In an example, an intrasacular aneurysm occlusion device can be formed from multiple arcuate portions connected together in parallel with the plane of an aneurysm neck. In an example, a multi-portion longitudinal stack can comprise a centrally-connected plurality of proximal, central, and distal arcuate portions. In an example, different arcuate portions of a multi-portion stack need not be of uniform tensile strength, flexibility, plasticity, or elasticity. For example, distal arcuate portions of a stack can be more flexible (and/or have lower tensile strength) than proximal arcuate portions. Also, distal arcuate portions of a stack can be more porous than proximal arcuate portions of the stack.

In an example, an intrasacular aneurysm occlusion device can comprise: a net or mesh with a first level of radial stiffness, measured in newtons per meter or pounds per inch; wherein the net or mesh is configured to be inserted into and expanded in a first location within an aneurysm sac; and a stent with a second level of radial stiffness, measured in newtons per meter or pounds per inch; wherein the stent is configured to be inserted into and expanded in a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded in a first location within an aneurysm sac; and a stent with a second level of radial stiffness, measured in newtons per meter or pounds per inch; wherein the stent is configured to be inserted into and expanded in a second location within the aneurysm sac; wherein the first level is less than the second level; and wherein the first location is further from the aneurysm neck than the second location.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is further from the aneurysm neck than the second location.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is further from the aneurysm neck than the second location.

In an example, an intrasacular aneurysm occlusion device can comprise: (1) a stent (or neck bridge); wherein the stent (or neck bridge) has a first configuration while it is being transported to an aneurysm sac; wherein the stent (or neck bridge) has a second configuration after it has been delivered into and expanded within the aneurysm sac; wherein the stent (or neck bridge) in its second configuration has a width in a plane which is substantially parallel to the circumference of the neck of the aneurysm sac and this width is greater than the diameter of the neck of the aneurysm sac; and wherein the stent (or neck bridge) in its second configuration has a first level of resiliency, rigidity, and/or stiffness; and (2) a flexible net (or mesh); wherein the flexible net (or mesh) has a first configuration while it is being transported to an aneurysm sac; wherein the flexible net (or mesh) has a second configuration after it has been delivered into and expanded within the aneurysm sac; wherein the flexible net (or mesh) is expanded from its first configuration to its second configuration by the insertion of embolic members into the flexible net (or mesh); and wherein the flexible net (or mesh) in its second configuration has a second level of resiliency, rigidity, and/or stiffness which is less than the first level of resiliency, rigidity, and/or stiffness.

In an example, an intrasacular aneurysm occlusion device can comprise: (1) an intravascular delivery lumen; (2) a plurality of embolic members; (3) a proximal neck bridge; wherein proximal is defined as closer to the aneurysm neck and distal is defined as closer to the aneurysm dome; wherein the neck bridge is configured to occlude the neck of an aneurysm sac; wherein the neck bridge has a first configuration while it is being transported through the delivery lumen to an aneurysm sac and a second configuration after it has been expanded within the aneurysm sac; wherein the neck bridge in its second configuration has a width which is greater than the diameter of the neck of the aneurysm sac; and wherein the neck bridge in its second configuration has a first level of flexibility, elasticity, and/or malleability; and (4) a distal net or mesh; wherein distal is defined as being closer to an aneurysm dome and proximal is defined as closer to the aneurysm neck; wherein the net or mesh has a first configuration while it is being transported through the delivery lumen to an aneurysm sac; wherein the net or mesh has a second configuration after it has been expanded within the aneurysm sac; wherein the net or mesh is configured to conform to the walls of an aneurysm sac in its second configuration; wherein the net or mesh is expanded from its first configuration to its second configuration by the insertion of the embolic members into the net or mesh; wherein the net or mesh in its second configuration has a second level of flexibility, elasticity, and/or malleability which is greater than the first level of flexibility, elasticity, and/or malleability.

In an example, different portions, segments, or undulations of a continuous intrasacular aneurysm occlusion device can have different braid pitches. In an example, a proximal portion, segment, or undulation of an intrasacular aneurysm occlusion device can have a first braid pitch and a distal portion, segment, or undulation of a device can have a second braid pitch. In an example, different portions, segments, or undulations of a continuous intrasacular aneurysm occlusion device can have different braid filament sizes. In an example, a proximal portion, segment, or undulation of an intrasacular aneurysm occlusion device can have a first braid filament size and a distal portion, segment, or undulation of a device can have a second braid filament size.

In an example, different portions, segments, or undulations of a continuous intrasacular convex structure can have different braid pitches. In an example, a proximal portion, segment, or undulation of a continuous intrasacular convex structure can have a first braid pitch and a distal portion, segment, or undulation of a device can have a second braid pitch. In an example, different portions, segments, or undulations of a continuous intrasacular convex structure can have different braid filament sizes. In an example, a proximal portion, segment, or undulation of a continuous intrasacular convex structure can have a first braid filament size and a distal portion, segment, or undulation of a device can have a second braid filament size.

In an example, different portions, segments, or undulations of a continuous intrasacular convex structure can have different braid patterns. In an example, a proximal portion, segment, or undulation of a continuous intrasacular convex structure can have a first braid pattern and a distal portion, segment, or undulation of a device can have a second braid pattern. In an example, different portions, segments, or undulations of a continuous intrasacular convex structure can have different braid densities. In an example, a proximal portion, segment, or undulation of a continuous intrasacular convex structure can have a higher braid density than a distal portion, segment, or undulation of a device. In an example, different portions, segments, or undulations of a continuous intrasacular convex structure can have different braid angles. In an example, a proximal portion, segment, or undulation of a continuous intrasacular convex structure can have a greater braid angle than a distal portion, segment, or undulation of a device.

In an example, resilient wider-than-neck and flexible sac-filling portions of a device can be different portions of the same continuous embolic structure which is inserted into an aneurysm sac. In an example, a resilient wider-than-neck portion of a device and a flexible sac-filling portion of a device can be proximal and distal portions, respectively, of an intrasacular occlusion device. In an example, a resilient wider-than-neck portion of a device can comprise the proximal surface of an intrasacular occlusion device and a flexible sac-filling portion can comprise the distal and lateral surfaces of this intrasacular occlusion device. In an example, a resilient wider-than-neck portion can be a proximal part, portion, segment, or undulation of this structure and a flexible sac-filling portion can be a distal (and/or peripheral) part, portion, segment, or undulation of this structure. In an example, a resilient wider-than-neck portion can be a proximal part, portion, segment, or undulation of an intrasacular aneurysm occlusion device and a flexible sac-filling portion can be a distal (and/or peripheral) part, portion, segment, or undulation of a device. In an example, a resilient wider-than-neck portion can be a proximal part, portion, segment, or undulation of an intrasacular embolic stack of parts, portions, segments, or undulations and a flexible sac-filling portion can be a distal (and/or peripheral) part, portion, segment, or undulation of this stack. Relevant example variations discussed elsewhere in this disclosure or priority-linked disclosures can also be applied to this example.

Figure 4:
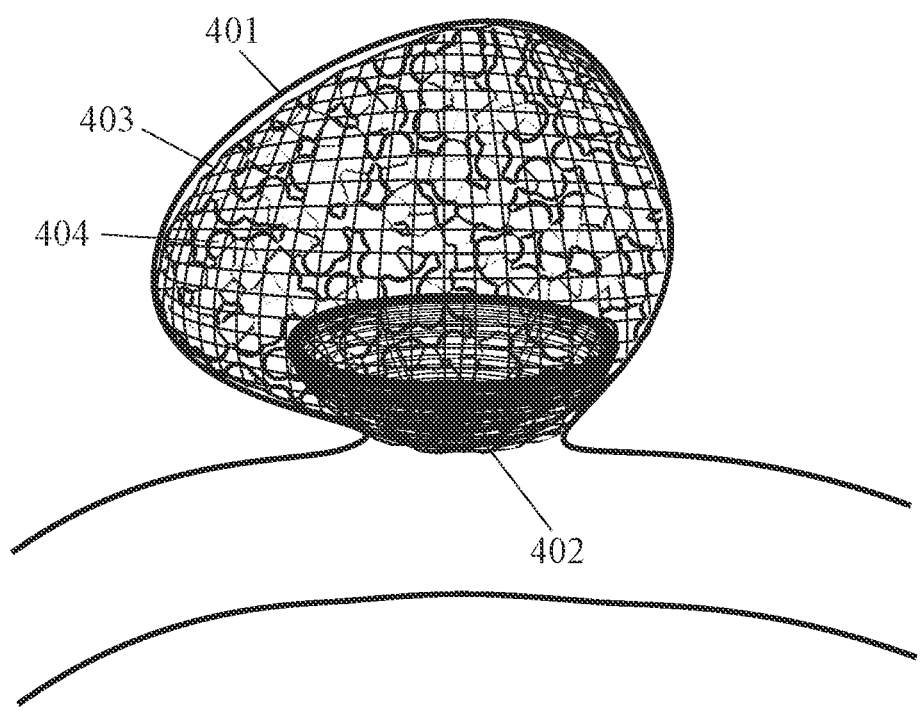
FIG. 4 shows an aneurysm occlusion device with a distal mesh and a proximal mesh, wherein the proximal mesh is stiffer than the first mesh, the proximal mesh is inside the distal mesh, and the proximal mesh is bowl-shaped.

FIG. 4 shows an example of a intrasacular aneurysm occlusion device comprising: a resilient wider-than-neck portion 402 (such as a stent or neck bridge) of a device with a first (constrained) configuration as it is transported to an aneurysm sac 401 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 403 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 404 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability.

In FIG. 4, the resilient wider-than-neck portion of the device has self-expanded into a bowl shape. In an example, a resilient wider-than-neck portion of a device can be expanded into a bowl shape in a multi-step transition from its first (constrained) configuration to its second (expanded) configuration. In an example of a multi-step transition, the resilient wider-than-neck portion can be expanded to a spherical or ellipsoidal shape in a first step and then this sphere or ellipsoid can be collapsed into a (two-layer) bowl shape in a second step. In an example, it can be collapsed from a spherical or ellipsoidal shape to a bowl shape by pulling a wire, cord, string, or cable which is connected to its distal surface but not connected to its proximal surface.

The flexible sac-filling portion of the device shown in FIG. 4 comprises a first mesh or net with a first proximal-to-distal length, a first stiffness level, and a first elasticity level. The resilient wider-than-neck portion of the device shown in FIG. 4 comprises a second mesh or net with a second proximal-to-distal length, a second stiffness level, and a second elasticity level. As shown in FIG. 4, the second proximal-to-distal length can be less than the first proximal-to-distal length. As discussed above, the second elasticity level can be less than the first elasticity level. Since stiffness can be the opposite of elasticity and/or flexibility, the second stiffness level can be greater than the first stiffness level.

As discussed above in accordance with the example in FIG. 4, an intrasacular aneurysm occlusion device can comprise: a first mesh or net (e.g. mesh, net, shell, or stent) which is configured to be inserted and expanded within an aneurysm sac, wherein the first mesh or net has a first proximal-to-distal length, wherein the first mesh or net has a first stiffness level, and wherein the first mesh or net has a first elasticity level; and a second mesh or net (e.g. mesh, net, shell, or stent) which is in contact with a proximal portion of the first mesh or net, wherein the second mesh or net has a second proximal-to-distal length, wherein the second mesh or net has a second stiffness level, wherein the second mesh or net has a second elasticity level, wherein the second proximal-to-distal length is less than the first proximal-to-distal length, and wherein the second stiffness level is greater than the first stiffness level and/or the second elasticity level is less than the first elasticity level.

In an example, filaments (e.g. wires or strands) comprising the first mesh or net can have a first thickness and filaments (e.g. wires or strands) comprising the second mesh or net can have a second thickness, wherein the second thickness is greater than the first thickness. As shown in FIG. 4, the second mesh or net can be in contact with only the proximal half of the first mesh or net. As also shown in FIG. 4, the second proximal-to-distal length can be between 25% and 75% of the first proximal-to-distal length. In an example, the second mesh or net can be in contact with only the proximal third of the first mesh or net. In an example, the second proximal-to-distal length can be between 20% and 40% of the first proximal-to-distal length.

As shown in FIG. 4, the second mesh or net can be inside the first mesh or net. In an alternative embodiment, the second mesh or net can be outside the first mesh or net. In this example, the first mesh or net has an irregular shape. In another example, the first mesh or net can have a generally globular (e.g. spherical, oblate spherical or ellipsoidal or toroidal) shape. In this example, the second mesh or net has a bowl (e.g. hemispherical, hemi-ellipsoidal, or half-toroidal) shape. In this example, the first mesh or net and the second mesh or net can be connected at a proximal hub. In another example, the first mesh or net and the second mesh or net can be connected at a distal hub. In an example, there can be a central proximal opening in one or both of the meshes or nets through which embolic material (e.g. coils, liquid embolic material, string-of-pearls embolics, or embolic pieces). In this example, the first mesh or net and the second mesh or net are separate structures which have been connected. In an alternative example, the first mesh or net and the second mesh or net can be portions, sections, and/or lobes of the same (tubular) mesh structure which has been radially-constrained, inverted, and/or everted.

In an example, a proximal portion of an intrasacular occlusion device can comprise a resilient wider-than-neck portion with a first softness level and a distal portion of this intrasacular occlusion device can comprise a flexible sac-filling portion with a second softness level, wherein the second level is greater than the first level. In an example, the proximal portion of an intrasacular occlusion device can comprise a resilient wider-than-neck portion with a first stiffness level and a distal portion of this intrasacular occlusion device can comprise a flexible sac-filling portion with a second stiffness level, wherein the second level is less than the first level.

In an example, a proximal surface of a flexible sac-filling portion of a device can have a first thickness; the distal surface of a flexible sac-filling portion of a device can have a second thickness; and the first thickness can be greater than the second thickness. In an example, a proximal part of a flexible sac-filling portion can have a first width and a distal part of the flexible sac-filling portion can have a second width, wherein the second width is greater than the first width. In an example, different areas of flexible sac-filling portion can have different levels of resiliency.

In an example, a resilient wider-than-neck portion and a flexible sac-filling portion can be different parts of the same continuous intrasacular occlusion device, but have different properties. In an example, the proximal portion of this intrasacular occlusion device can comprise a resilient wider-than-neck portion with a first density level and a distal portion of this intrasacular occlusion device can comprise a flexible sac-filling portion with a second density level, wherein the second level is less than the first level. In an example, the proximal portion of an intrasacular occlusion device can comprise a resilient wider-than-neck portion with a first elasticity level and a distal portion of this intrasacular occlusion device can comprise a flexible sac-filling portion with a second elasticity level, wherein the second level is greater than the first level. In an example, the proximal portion of an intrasacular occlusion device can comprise a resilient wider-than-neck portion with a first flexibility level and a distal portion of this intrasacular occlusion device can comprise a flexible sac-filling portion with a second flexibility level, wherein the second level is greater than the first level.

In an example, a resilient wider-than-neck portion of a device can have a first porosity level and a flexible sac-filling portion can have a second porosity level, wherein the second level is greater than the first level. In an example, a resilient wider-than-neck portion of a device can have a first rigidity level and a flexible sac-filling portion can have a second rigidity level, wherein the second level is less than the first level. In an example, a flexible sac-filling portion of a device can be larger in its second (expanded) configuration than the size of the resilient wider-than-neck portion of a device in its second (expanded) configuration. In an example, a resilient wider-than-neck portion of a device can have a first softness level and a flexible sac-filling portion can have a second softness level, wherein the second level is greater than the first level. In an example, a resilient wider-than-neck portion of a device can have a first stiffness level and a flexible sac-filling portion can have a second stiffness level, wherein the second level is less than the first level. In an example, a flexible sac-filling portion of a device can be larger in its second (expanded) configuration than a resilient wider-than-neck portion of a device in its second (expanded) configuration.

In an example, an aneurysm occlusion device can comprise: (1) a resilient wider-than-neck portion of the device; wherein the resilient wider-than-neck portion has a first configuration while it is being transported to an aneurysm sac; wherein the resilient wider-than-neck portion has a second configuration after it has been delivered into and expanded within the aneurysm sac; wherein the resilient wider-than-neck portion in its second configuration has a width in a plane which is substantially parallel to the circumference of the neck of the aneurysm sac and this width is greater than the diameter of the neck of the aneurysm sac; and wherein the resilient wider-than-neck in its second configuration has a first level of resiliency, rigidity, and/or stiffness; and (2) a flexible sac-filling portion of the device; wherein the flexible sac-filling portion has a first configuration while it is being transported to an aneurysm sac; wherein the flexible sac-filling portion has a second configuration after it has been delivered into and expanded within the aneurysm sac; wherein the flexible sac-filling portion is expanded from its first configuration to its second configuration by the insertion of embolic members into the flexible sac-filling portion; and wherein the flexible sac-filling portion in its second configuration has a second level of resiliency, rigidity, and/or stiffness which is less than the first level of resiliency, rigidity, and/or stiffness.

In an example, an aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a proximal location and a second tensile strength at a distal location, and wherein the second tensile strength is less than the first tensile strength. In an example, an aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a proximal location and a second elasticity at a distal location, and wherein the second elasticity is greater than the first elasticity.

In an example, an aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a proximal location and a second flexibility at a distal location, and wherein the second flexibility is greater than the first flexibility. In an example, an aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a proximal location and a second porosity at a distal location, and wherein the second porosity is greater than the first porosity. Relevant embodiment variations discussed elsewhere in this disclosure or in priority-linked disclosures can also apply to this example.

In an example, an intrasacular aneurysm occlusion device can be formed from multiple arcuate portions connected together in parallel with the plane of an aneurysm neck. In an example, a multi-portion longitudinal stack can comprise a centrally-connected plurality of proximal, central, and distal arcuate portions. In an example, different arcuate portions of a multi-portion stack need not be of uniform tensile strength, flexibility, plasticity, or elasticity. For example, distal arcuate portions of a stack can be more flexible (and/or have lower tensile strength) than proximal arcuate portions. Also, distal arcuate portions of a stack can be more porous than proximal arcuate portions of the stack.

In an example, an intrasacular aneurysm occlusion device can comprise: a net or mesh with a first level of radial stiffness, measured in newtons per meter or pounds per inch; wherein the net or mesh is configured to be inserted into and expanded in a first location within an aneurysm sac; and a stent with a second level of radial stiffness, measured in newtons per meter or pounds per inch; wherein the stent is configured to be inserted into and expanded in a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded in a first location within an aneurysm sac; and a stent with a second level of radial stiffness, measured in newtons per meter or pounds per inch; wherein the stent is configured to be inserted into and expanded in a second location within the aneurysm sac; wherein the first level is less than the second level; and wherein the first location is further from the aneurysm neck than the second location.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is further from the aneurysm neck than the second location.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is further from the aneurysm neck than the second location.

In an example, an intrasacular aneurysm occlusion device can comprise: (1) a stent (or neck bridge); wherein the stent (or neck bridge) has a first configuration while it is being transported to an aneurysm sac; wherein the stent (or neck bridge) has a second configuration after it has been delivered into and expanded within the aneurysm sac; wherein the stent (or neck bridge) in its second configuration has a width in a plane which is substantially parallel to the circumference of the neck of the aneurysm sac and this width is greater than the diameter of the neck of the aneurysm sac; and wherein the stent (or neck bridge) in its second configuration has a first level of resiliency, rigidity, and/or stiffness; and (2) a flexible net (or mesh); wherein the flexible net (or mesh) has a first configuration while it is being transported to an aneurysm sac; wherein the flexible net (or mesh) has a second configuration after it has been delivered into and expanded within the aneurysm sac; wherein the flexible net (or mesh) is expanded from its first configuration to its second configuration by the insertion of embolic members into the flexible net (or mesh); and wherein the flexible net (or mesh) in its second configuration has a second level of resiliency, rigidity, and/or stiffness which is less than the first level of resiliency, rigidity, and/or stiffness.

In an example, an intrasacular aneurysm occlusion device can comprise: (1) an intravascular delivery lumen; (2) a plurality of embolic members; (3) a proximal neck bridge; wherein proximal is defined as closer to the aneurysm neck and distal is defined as closer to the aneurysm dome; wherein the neck bridge is configured to occlude the neck of an aneurysm sac; wherein the neck bridge has a first configuration while it is being transported through the delivery lumen to an aneurysm sac and a second configuration after it has been expanded within the aneurysm sac; wherein the neck bridge in its second configuration has a width which is greater than the diameter of the neck of the aneurysm sac; and wherein the neck bridge in its second configuration has a first level of flexibility, elasticity, and/or malleability; and (4) a distal net or mesh; wherein distal is defined as being closer to an aneurysm dome and proximal is defined as closer to the aneurysm neck; wherein the net or mesh has a first configuration while it is being transported through the delivery lumen to an aneurysm sac; wherein the net or mesh has a second configuration after it has been expanded within the aneurysm sac; wherein the net or mesh is configured to conform to the walls of an aneurysm sac in its second configuration; wherein the net or mesh is expanded from its first configuration to its second configuration by the insertion of the embolic members into the net or mesh; wherein the net or mesh in its second configuration has a second level of flexibility, elasticity, and/or malleability which is greater than the first level of flexibility, elasticity, and/or malleability.

In an example, different portions, segments, or undulations of a continuous intrasacular aneurysm occlusion device can have different braid pitches. In an example, a proximal portion, segment, or undulation of an intrasacular aneurysm occlusion device can have a first braid pitch and a distal portion, segment, or undulation of a device can have a second braid pitch. In an example, different portions, segments, or undulations of a continuous intrasacular aneurysm occlusion device can have different braid filament sizes. In an example, a proximal portion, segment, or undulation of an intrasacular aneurysm occlusion device can have a first braid filament size and a distal portion, segment, or undulation of a device can have a second braid filament size.

In an example, different portions, segments, or undulations of a continuous intrasacular convex structure can have different braid pitches. In an example, a proximal portion, segment, or undulation of a continuous intrasacular convex structure can have a first braid pitch and a distal portion, segment, or undulation of a device can have a second braid pitch. In an example, different portions, segments, or undulations of a continuous intrasacular convex structure can have different braid filament sizes. In an example, a proximal portion, segment, or undulation of a continuous intrasacular convex structure can have a first braid filament size and a distal portion, segment, or undulation of a device can have a second braid filament size.

In an example, different portions, segments, or undulations of a continuous intrasacular convex structure can have different braid patterns. In an example, a proximal portion, segment, or undulation of a continuous intrasacular convex structure can have a first braid pattern and a distal portion, segment, or undulation of a device can have a second braid pattern. In an example, different portions, segments, or undulations of a continuous intrasacular convex structure can have different braid densities. In an example, a proximal portion, segment, or undulation of a continuous intrasacular convex structure can have a higher braid density than a distal portion, segment, or undulation of a device. In an example, different portions, segments, or undulations of a continuous intrasacular convex structure can have different braid angles. In an example, a proximal portion, segment, or undulation of a continuous intrasacular convex structure can have a greater braid angle than a distal portion, segment, or undulation of a device.

In an example, resilient wider-than-neck and flexible sac-filling portions of a device can be different portions of the same continuous embolic structure which is inserted into an aneurysm sac. In an example, a resilient wider-than-neck portion of a device and a flexible sac-filling portion of a device can be proximal and distal portions, respectively, of an intrasacular occlusion device. In an example, a resilient wider-than-neck portion of a device can comprise the proximal surface of an intrasacular occlusion device and a flexible sac-filling portion can comprise the distal and lateral surfaces of this intrasacular occlusion device. In an example, a resilient wider-than-neck portion can be a proximal part, portion, segment, or undulation of this structure and a flexible sac-filling portion can be a distal (and/or peripheral) part, portion, segment, or undulation of this structure. In an example, a resilient wider-than-neck portion can be a proximal part, portion, segment, or undulation of an intrasacular aneurysm occlusion device and a flexible sac-filling portion can be a distal (and/or peripheral) part, portion, segment, or undulation of a device. In an example, a resilient wider-than-neck portion can be a proximal part, portion, segment, or undulation of an intrasacular embolic stack of parts, portions, segments, or undulations and a flexible sac-filling portion can be a distal (and/or peripheral) part, portion, segment, or undulation of this stack. Relevant example variations discussed elsewhere in this disclosure or priority-linked disclosures can also be applied to this example.

Figure 5:
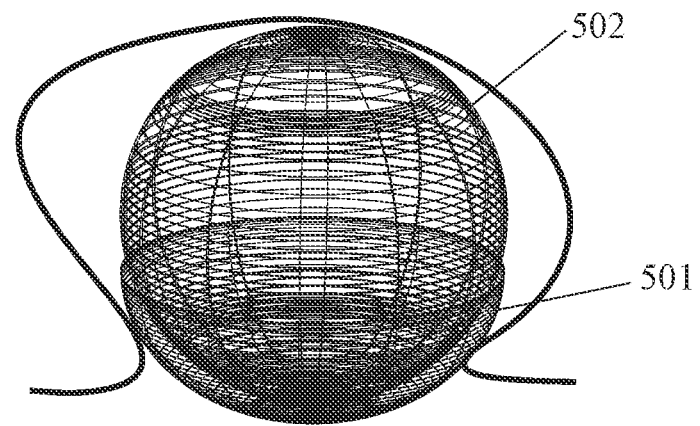
FIG. 5 shows an aneurysm occlusion device with a distal mesh and a proximal mesh, wherein the proximal mesh is stiffer than the first mesh, the distal mesh is nested within a concavity of the proximal mesh, and the proximal mesh is bowl-shaped.

FIG. 5 shows an example of an intrasacular aneurysm occlusion device comprising: an intrasacular arcuate distal stent 502 and an intrasacular arcuate proximal stent 501, wherein the proximal stent has a concavity into which a portion of the distal stent fits when the device is deployed within an aneurysm sac. In an example, a distal stent can be spherical when it is expanded and a proximal stent can be hemispherical when it is expanded.

In an example, the proximal stent can be an inverted dome or other section of a sphere when it is expanded. In an example, an intrasacular aneurysm occlusion device can comprise a distal ball stent and a proximal hemispherical stent, wherein both are expanded and overlap each other when they are deployed within an aneurysm sac. In an example, a distal surface of a proximal hemispherical stent can overlap a proximal surface of a distal ball stent. In an example, a distal stent can be an ellipsoid when it is expanded and a proximal stent can be a section of an ellipsoid when it is expanded. In this example, the arcuate distal stent and the arcuate proximal stent form a double-thickness wire mesh which covers the aneurysm neck.

In an example, a distal stent can have a compressed first configuration as it is conveyed through a catheter and an expanded second configuration after it exits the catheter within an aneurysm sac. In an example, the maximum width of a distal stent in its second configuration can be wider than the aneurysm neck. In an example, a proximal stent can have a compressed first configuration as it is conveyed through a catheter and an expanded second configuration after it exits the catheter within an aneurysm sac.

The intrasacular arcuate distal stent shown in FIG. 5 can comprise a first mesh or net. The intrasacular arcuate proximal stent shown in FIG. 5 can comprise a second mesh or net. As shown in FIG. 5, the first mesh or net can be generally spherical (e.g. globular, spherical, oblate spherical, and/or ellipsoidal), the second mesh or net can be generally hemispherical (e.g. bowl shaped or inverted-dome shaped), and one mesh or net can fit into the other mesh or net. In this example, a proximal portion of the globular mesh fits into the concavity of the bowl-shaped mesh. In another example, the bowl-shaped mesh can fit inside a proximal portion of the globular mesh.

In accordance with the above discussion, an intrasacular aneurysm occlusion device can comprise: a first mesh or net (e.g. mesh, net, shell, or stent) which is configured to be inserted and expanded within an aneurysm sac, wherein the first mesh or net has a first proximal-to-distal length, wherein the first mesh or net has a first stiffness level, and wherein the first mesh or net has a first elasticity level; and a second mesh or net (e.g. mesh, net, shell, or stent) which is in contact with a proximal portion of the first mesh or net, wherein the second mesh or net has a second proximal-to-distal length, wherein the second mesh or net has a second stiffness level, wherein the second mesh or net has a second elasticity level, wherein the second proximal-to-distal length is less than the first proximal-to-distal length, and wherein the second stiffness level is greater than the first stiffness level and/or the second elasticity level is less than the first elasticity level.

In an example, filaments (e.g. wires or strands) comprising the first mesh or net can have a first thickness and filaments (e.g. wires or strands) comprising the second mesh or net can have a second thickness, wherein the second thickness is greater than the first thickness. In an example, the second mesh or net can be in contact with only the proximal half of the first mesh or net. In an example, the second proximal-to-distal length can be between 25% and 75% of the first proximal-to-distal length. In an example, the second mesh or net can be in contact with only the proximal third of the first mesh or net. In an example, the second proximal-to-distal length can be between 20% and 40% of the first proximal-to-distal length.

In the example shown in FIG. 5, the first mesh or net fits inside the concavity of the second mesh or net. In another example, the second mesh or net can be inside the first mesh or net. In an example, the first mesh or net can have a generally globular (e.g. spherical, oblate spherical or ellipsoidal or toroidal) shape and the second mesh or net can have a bowl (e.g. hemispherical, hemi-ellipsoidal, or half-toroidal) shape. In an example, the first mesh or net and the second mesh or net can be connected at a proximal hub. In an example, the first mesh or net and the second mesh or net can be connected at a proximal hub but not connected at a distal hub. In an example, there can be a central proximal opening in the first mesh or net through which embolic material (e.g. coils, congealing embolic liquid, string-of-pearls embolic strands, or embolic pieces) is inserted. In this example, the first and second meshes are separate structures which have been connected. In another example, the first mesh or net and the second mesh or net can be portions, sections, and/or lobes of the same (tubular) mesh structure which has been radially-constrained, inverted, and/or everted.

In an example, a proximal portion of an intrasacular occlusion device can comprise a resilient wider-than-neck portion with a first softness level and a distal portion of this intrasacular occlusion device can comprise a flexible sac-filling portion with a second softness level, wherein the second level is greater than the first level. In an example, the proximal portion of an intrasacular occlusion device can comprise a resilient wider-than-neck portion with a first stiffness level and a distal portion of this intrasacular occlusion device can comprise a flexible sac-filling portion with a second stiffness level, wherein the second level is less than the first level.

In an example, a proximal surface of a flexible sac-filling portion of a device can have a first thickness; the distal surface of a flexible sac-filling portion of a device can have a second thickness; and the first thickness can be greater than the second thickness. In an example, a proximal part of a flexible sac-filling portion can have a first width and a distal part of the flexible sac-filling portion can have a second width, wherein the second width is greater than the first width. In an example, different areas of flexible sac-filling portion can have different levels of resiliency.

In an example, a resilient wider-than-neck portion and a flexible sac-filling portion can be different parts of the same continuous intrasacular occlusion device, but have different properties. In an example, the proximal portion of this intrasacular occlusion device can comprise a resilient wider-than-neck portion with a first density level and a distal portion of this intrasacular occlusion device can comprise a flexible sac-filling portion with a second density level, wherein the second level is less than the first level. In an example, the proximal portion of an intrasacular occlusion device can comprise a resilient wider-than-neck portion with a first elasticity level and a distal portion of this intrasacular occlusion device can comprise a flexible sac-filling portion with a second elasticity level, wherein the second level is greater than the first level. In an example, the proximal portion of an intrasacular occlusion device can comprise a resilient wider-than-neck portion with a first flexibility level and a distal portion of this intrasacular occlusion device can comprise a flexible sac-filling portion with a second flexibility level, wherein the second level is greater than the first level.

In an example, a resilient wider-than-neck portion of a device can have a first porosity level and a flexible sac-filling portion can have a second porosity level, wherein the second level is greater than the first level. In an example, a resilient wider-than-neck portion of a device can have a first rigidity level and a flexible sac-filling portion can have a second rigidity level, wherein the second level is less than the first level. In an example, a flexible sac-filling portion of a device can be larger in its second (expanded) configuration than the size of the resilient wider-than-neck portion of a device in its second (expanded) configuration. In an example, a resilient wider-than-neck portion of a device can have a first softness level and a flexible sac-filling portion can have a second softness level, wherein the second level is greater than the first level. In an example, a resilient wider-than-neck portion of a device can have a first stiffness level and a flexible sac-filling portion can have a second stiffness level, wherein the second level is less than the first level. In an example, a flexible sac-filling portion of a device can be larger in its second (expanded) configuration than a resilient wider-than-neck portion of a device in its second (expanded) configuration.

In an example, an aneurysm occlusion device can comprise: (1) a resilient wider-than-neck portion of the device; wherein the resilient wider-than-neck portion has a first configuration while it is being transported to an aneurysm sac; wherein the resilient wider-than-neck portion has a second configuration after it has been delivered into and expanded within the aneurysm sac; wherein the resilient wider-than-neck portion in its second configuration has a width in a plane which is substantially parallel to the circumference of the neck of the aneurysm sac and this width is greater than the diameter of the neck of the aneurysm sac; and wherein the resilient wider-than-neck in its second configuration has a first level of resiliency, rigidity, and/or stiffness; and (2) a flexible sac-filling portion of the device; wherein the flexible sac-filling portion has a first configuration while it is being transported to an aneurysm sac; wherein the flexible sac-filling portion has a second configuration after it has been delivered into and expanded within the aneurysm sac; wherein the flexible sac-filling portion is expanded from its first configuration to its second configuration by the insertion of embolic members into the flexible sac-filling portion; and wherein the flexible sac-filling portion in its second configuration has a second level of resiliency, rigidity, and/or stiffness which is less than the first level of resiliency, rigidity, and/or stiffness.

In an example, an aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a proximal location and a second tensile strength at a distal location, and wherein the second tensile strength is less than the first tensile strength. In an example, an aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a proximal location and a second elasticity at a distal location, and wherein the second elasticity is greater than the first elasticity.

In an example, an aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a proximal location and a second flexibility at a distal location, and wherein the second flexibility is greater than the first flexibility. In an example, an aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a proximal location and a second porosity at a distal location, and wherein the second porosity is greater than the first porosity. Relevant embodiment variations discussed elsewhere in this disclosure or in priority-linked disclosures can also apply to this example.

In an example, an intrasacular aneurysm occlusion device can be formed from multiple arcuate portions connected together in parallel with the plane of an aneurysm neck. In an example, a multi-portion longitudinal stack can comprise a centrally-connected plurality of proximal, central, and distal arcuate portions. In an example, different arcuate portions of a multi-portion stack need not be of uniform tensile strength, flexibility, plasticity, or elasticity. For example, distal arcuate portions of a stack can be more flexible (and/or have lower tensile strength) than proximal arcuate portions. Also, distal arcuate portions of a stack can be more porous than proximal arcuate portions of the stack.

In an example, an intrasacular aneurysm occlusion device can comprise: a net or mesh with a first level of radial stiffness, measured in newtons per meter or pounds per inch; wherein the net or mesh is configured to be inserted into and expanded in a first location within an aneurysm sac; and a stent with a second level of radial stiffness, measured in newtons per meter or pounds per inch; wherein the stent is configured to be inserted into and expanded in a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded in a first location within an aneurysm sac; and a stent with a second level of radial stiffness, measured in newtons per meter or pounds per inch; wherein the stent is configured to be inserted into and expanded in a second location within the aneurysm sac; wherein the first level is less than the second level; and wherein the first location is further from the aneurysm neck than the second location.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is further from the aneurysm neck than the second location.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is further from the aneurysm neck than the second location.

In an example, an intrasacular aneurysm occlusion device can comprise: (1) a stent (or neck bridge); wherein the stent (or neck bridge) has a first configuration while it is being transported to an aneurysm sac; wherein the stent (or neck bridge) has a second configuration after it has been delivered into and expanded within the aneurysm sac; wherein the stent (or neck bridge) in its second configuration has a width in a plane which is substantially parallel to the circumference of the neck of the aneurysm sac and this width is greater than the diameter of the neck of the aneurysm sac; and wherein the stent (or neck bridge) in its second configuration has a first level of resiliency, rigidity, and/or stiffness; and (2) a flexible net (or mesh); wherein the flexible net (or mesh) has a first configuration while it is being transported to an aneurysm sac; wherein the flexible net (or mesh) has a second configuration after it has been delivered into and expanded within the aneurysm sac; wherein the flexible net (or mesh) is expanded from its first configuration to its second configuration by the insertion of embolic members into the flexible net (or mesh); and wherein the flexible net (or mesh) in its second configuration has a second level of resiliency, rigidity, and/or stiffness which is less than the first level of resiliency, rigidity, and/or stiffness.

In an example, an intrasacular aneurysm occlusion device can comprise: (1) an intravascular delivery lumen; (2) a plurality of embolic members; (3) a proximal neck bridge; wherein proximal is defined as closer to the aneurysm neck and distal is defined as closer to the aneurysm dome; wherein the neck bridge is configured to occlude the neck of an aneurysm sac; wherein the neck bridge has a first configuration while it is being transported through the delivery lumen to an aneurysm sac and a second configuration after it has been expanded within the aneurysm sac; wherein the neck bridge in its second configuration has a width which is greater than the diameter of the neck of the aneurysm sac; and wherein the neck bridge in its second configuration has a first level of flexibility, elasticity, and/or malleability; and (4) a distal net or mesh; wherein distal is defined as being closer to an aneurysm dome and proximal is defined as closer to the aneurysm neck; wherein the net or mesh has a first configuration while it is being transported through the delivery lumen to an aneurysm sac; wherein the net or mesh has a second configuration after it has been expanded within the aneurysm sac; wherein the net or mesh is configured to conform to the walls of an aneurysm sac in its second configuration; wherein the net or mesh is expanded from its first configuration to its second configuration by the insertion of the embolic members into the net or mesh; wherein the net or mesh in its second configuration has a second level of flexibility, elasticity, and/or malleability which is greater than the first level of flexibility, elasticity, and/or malleability.

In an example, different portions, segments, or undulations of a continuous intrasacular aneurysm occlusion device can have different braid pitches. In an example, a proximal portion, segment, or undulation of an intrasacular aneurysm occlusion device can have a first braid pitch and a distal portion, segment, or undulation of a device can have a second braid pitch. In an example, different portions, segments, or undulations of a continuous intrasacular aneurysm occlusion device can have different braid filament sizes. In an example, a proximal portion, segment, or undulation of an intrasacular aneurysm occlusion device can have a first braid filament size and a distal portion, segment, or undulation of a device can have a second braid filament size.

In an example, different portions, segments, or undulations of a continuous intrasacular convex structure can have different braid pitches. In an example, a proximal portion, segment, or undulation of a continuous intrasacular convex structure can have a first braid pitch and a distal portion, segment, or undulation of a device can have a second braid pitch. In an example, different portions, segments, or undulations of a continuous intrasacular convex structure can have different braid filament sizes. In an example, a proximal portion, segment, or undulation of a continuous intrasacular convex structure can have a first braid filament size and a distal portion, segment, or undulation of a device can have a second braid filament size.

In an example, different portions, segments, or undulations of a continuous intrasacular convex structure can have different braid patterns. In an example, a proximal portion, segment, or undulation of a continuous intrasacular convex structure can have a first braid pattern and a distal portion, segment, or undulation of a device can have a second braid pattern. In an example, different portions, segments, or undulations of a continuous intrasacular convex structure can have different braid densities. In an example, a proximal portion, segment, or undulation of a continuous intrasacular convex structure can have a higher braid density than a distal portion, segment, or undulation of a device. In an example, different portions, segments, or undulations of a continuous intrasacular convex structure can have different braid angles. In an example, a proximal portion, segment, or undulation of a continuous intrasacular convex structure can have a greater braid angle than a distal portion, segment, or undulation of a device.

In an example, resilient wider-than-neck and flexible sac-filling portions of a device can be different portions of the same continuous embolic structure which is inserted into an aneurysm sac. In an example, a resilient wider-than-neck portion of a device and a flexible sac-filling portion of a device can be proximal and distal portions, respectively, of an intrasacular occlusion device. In an example, a resilient wider-than-neck portion of a device can comprise the proximal surface of an intrasacular occlusion device and a flexible sac-filling portion can comprise the distal and lateral surfaces of this intrasacular occlusion device. In an example, a resilient wider-than-neck portion can be a proximal part, portion, segment, or undulation of this structure and a flexible sac-filling portion can be a distal (and/or peripheral) part, portion, segment, or undulation of this structure. In an example, a resilient wider-than-neck portion can be a proximal part, portion, segment, or undulation of an intrasacular aneurysm occlusion device and a flexible sac-filling portion can be a distal (and/or peripheral) part, portion, segment, or undulation of a device. In an example, a resilient wider-than-neck portion can be a proximal part, portion, segment, or undulation of an intrasacular embolic stack of parts, portions, segments, or undulations and a flexible sac-filling portion can be a distal (and/or peripheral) part, portion, segment, or undulation of this stack. Relevant example variations discussed elsewhere in this disclosure or priority-linked disclosures can also be applied to this example.

Figure 6:
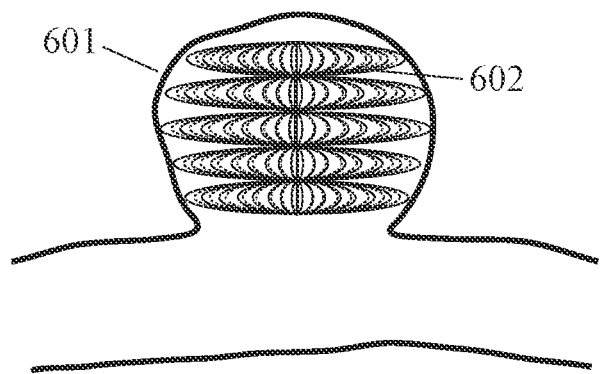
FIG. 6 shows an aneurysm occlusion device with a plurality of radial lobes along its proximal-to-distal longitudinal axis.

FIG. 6 shows an example of an intrasacular aneurysm occlusion device comprising: a series of connected embolic ellipsoids (including 602) which are configured to be inserted into an aneurysm sac 601. In an example, this device can comprise a series of centrally-connected arcuate structures which have individual shapes which are not ellipsoids. In an example, the shapes of these centrally-connected structures can be selected from the group consisting of: apple shape; bowl shape; compressed-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus.

In an example, an intrasacular aneurysm occlusion device can comprise multiple centrally-aligned arcuate embolic structures or portions. In an example, a multi-portion longitudinal stack can comprise a centrally-connected plurality of proximal, central, and distal arcuate portions. In an example, different arcuate portions of a multi-portion stack need not be of uniform tensile strength, flexibility, plasticity, or elasticity. For example, distal arcuate portions of a stack can be more flexible (and/or have lower tensile strength) than proximal arcuate portions. Also, distal arcuate portions of a stack can be more porous than proximal arcuate portions of the stack.

In an example, a stack of multiple centrally-aligned arcuate embolic structures or portions as shown in FIG. 6 can comprise a plurality of radial lobes along a proximal-to-distal longitudinal axis of a device. In an example, a centrally-connected plurality of proximal, central, and distal arcuate portions of a device as shown in FIG. 6 can comprise proximal, central, and distal radial lobes. As shown in FIG. 6, proximal, central, and distal radial lobes can have different sizes. In an example, different radial lobes can have different shapes selected from the group consisting of: apple shape; bowl shape; compressed-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus. In an example, a central lobe can have a compressed-sphere shape. In an example, proximal and distal radial lobes can have rounded disk or Frisbee shapes.

In accordance with the above discussion an intrasacular aneurysm occlusion device like the one shown in FIG. 6 can comprise: a mesh or net (e.g. mesh, net, shell, or stent) with a plurality of radial lobes along its proximal-to-distal longitudinal axis which is configured to be inserted and expanded within an aneurysm sac, wherein the mesh or net further comprises: a central lobe; a proximal lobe which extends proximally from the central mesh lobe to span the aneurysm neck; and a distal lobe which extends distally from the central lobe toward the aneurysm dome, wherein the proximal lobe has a different shape and a smaller size than the central lobe, and wherein the distal lobe has a different shape and a smaller size than the central lobe.

In an example, the shapes of the proximal and distal radial lobes can be more longitudinally-compressed than the shape of a central lobe. In an example, a central lobe can have a generally globular (e.g. spherical, oblate spherical or ellipsoidal) shape, while proximal and distal radial lobes can have rounded disk or Frisbee shapes. In an example, the width of a central lobe can be greater than the width of a proximal lobe or distal lobe. In an example, the length of a central lobe can be greater than the length of a proximal lobe or distal lobe. In an example, proximal, central, and distal radial lobes can collectively form a "lantern shape" (e.g. like the Green Lantern symbol from the comic book character or a folded paper lantern) or a "TIE fighter shape" (e.g. like the craft that Darth Vader piloted in the first Star Wars movie). OK, so pretty apparent here that I am a nerd, but if you are actually reading through this whole thing then you probably are as well. In an example, proximal, central, and distal lobes can be portions, sections, and/or lobes of the same (tubular) mesh structure which has been radially-constrained.

In an example, a first shape-changing embolic member and a second shape-changing embolic member can be part of a centrally-aligned sequence and/or series of two shape-changing embolic members which collectively occlude an aneurysm. In an example, a first shape-changing embolic member and a second shape-changing embolic member can be part of a centrally-aligned sequence and/or series of three shape-changing embolic members which collectively occlude an aneurysm. In an example, a first shape-changing embolic member and a second shape-changing embolic member can be part of a centrally-aligned sequence and/or series of four shape-changing embolic members which collectively occlude an aneurysm. In an example, a first shape-changing embolic member and a second shape-changing embolic member can be part of a centrally-aligned sequence and/or series of five or more shape-changing embolic members which collectively occlude an aneurysm.

In an example, a first shape-changing embolic member and a second shape-changing embolic member can be part of a centrally-aligned sequence of two shape-changing elliptical or toroidal embolic members which collectively occlude an aneurysm. In an example, a first shape-changing embolic member and a second shape-changing embolic member can be part of a centrally-aligned sequence of three shape-changing elliptical or toroidal embolic members which collectively occlude an aneurysm. In an example, a first shape-changing embolic member and a second shape-changing embolic member can be part of a centrally-aligned sequence of four shape-changing elliptical or toroidal embolic members which collectively occlude an aneurysm. In an example, a first shape-changing embolic member and a second shape-changing embolic member can be part of a centrally-aligned sequence of five or more shape-changing elliptical or toroidal embolic members which collectively occlude an aneurysm.

In an example, a first shape-changing embolic member can have a shape in its second configuration which is selected from the group consisting of: ellipsoid, paraboloid, sphere, disk, cylinder, ovaloid, convex lens, wheel, tire, doughnut, and torus. In an example, a first shape-changing embolic member can have a cross-sectional shape in the X-Z plane in its second configuration which is selected from the group consisting of: ellipse, reflected parabola, circle, oval, convex lens, and torus. In an example, a second shape-changing embolic member can have a shape in its fourth configuration which is selected from the group consisting of: ellipsoid, paraboloid, sphere, disk, cylinder, ovaloid, convex lens, wheel, tire, doughnut, and torus. In an example, a second shape-changing embolic member can have a cross-sectional shape in the XX-ZZ plane in its fourth configuration which is selected from the group consisting of: ellipse, reflected parabola, circle, oval, convex lens, and torus.

In an example, a plurality of shape-changing embolic members can share a common central axis within an aneurysm sac. In an example, a plurality of shape-changing embolic members can form a stack of connected ellipsoid disks which share a common central axis within the aneurysm sac. In an example, a stack of connected ellipsoids can fill a greater volume of the aneurysm sac than would be filled by a single hollow-mesh structure (such as a wire-mesh single sphere or ellipsoid that is expanded with an aneurysm sac) with a similar-size perimeter as the combined stack of connected ellipsoid disks. In an example, at least one of the connected ellipsoids has a circumference that is larger than the circumference of the aneurysm neck in order to help keep the stack within the aneurysm sac.

In an example, the sizes of first and second shape-changing embolic members can be the same. In an example, the shapes of first and second shape-changing embolic members can be the same. In an example, the sizes of first and second shape-changing embolic members can be different. In an example, the shapes of first and second shape-changing embolic members can be different. In an example, a first shape-changing embolic member can have a circumference in its second configuration that is larger than the circumference of an aneurysm neck in order to keep it within the aneurysm sac. In an example, a second shape-changing embolic member can have a circumference in its fourth configuration that is larger than the circumference of an aneurysm neck in order to keep it within the aneurysm sac.

The size of a second shape-changing embolic member can be greater than the size of a first shape-changing embolic member. The shape of a second shape-changing embolic member can be different than the shape of a first shape-changing embolic member. In an example, a distal-to-proximal sequence of multiple shape-changing embolic members can be progressively larger and/or wider as they are sequentially deployed in an aneurysm. In an example, a distal-to-proximal sequence of multiple shape-changing embolic members can first be progressively larger and/or wider and then progressively smaller and/or narrower as they are sequentially deployed in an aneurysm. In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac.

In an example, a device for occluding an aneurysm can comprise: a multiple-width longitudinal mesh which is configured to be inserted into an aneurysm sac; wherein the multiple-width longitudinal mesh has a distal-to-proximal longitudinal axis prior to insertion into the aneurysm sac, wherein the multiple-width longitudinal mesh has a length dimension along (or parallel to) the distal-to-proximal longitudinal axis, wherein the multiple-width longitudinal mesh has a width dimension perpendicular (or orthogonal) to the length dimension, and wherein the multiple-width longitudinal mesh has a thickness dimension perpendicular (or orthogonal) to the length dimension and the width dimension; wherein the multiple-width longitudinal mesh further comprises a plurality of narrow longitudinal segments with a first average length, a first average width, and a first average thickness; wherein the multiple-width longitudinal mesh further comprises a plurality of wide longitudinal segments with a second average length, a second average width, and a second average thickness; and wherein the second average width is at least 50% more than the first average width, wherein the second average width is at least twice the second average thickness, wherein the second average length is at least equal to the first average length, and wherein these three dimensional comparisons are made after the multiple-width longitudinal mesh has been inserted into the aneurysm sac.

In an example, a device for occluding an aneurysm can comprise: a multiple-width longitudinal mesh which is configured to be inserted into an aneurysm sac; wherein the multiple-width longitudinal mesh has a first configuration prior to insertion into the aneurysm sac and a second configuration after insertion into aneurysm sac; wherein the multiple-width longitudinal mesh has a distal-to-proximal longitudinal axis in the first configuration; wherein the multiple-width longitudinal mesh has a length dimension along (or parallel to) the distal-to-proximal longitudinal axis, wherein the multiple-width longitudinal mesh has a width dimension perpendicular (or orthogonal) to the length dimension, and wherein the multiple-width longitudinal mesh has a thickness dimension perpendicular (or orthogonal) to the length dimension and the width dimension; wherein the multiple-width longitudinal mesh further comprises a plurality of narrow longitudinal segments with a first average length, a first average width, and a first average thickness; wherein the multiple-width longitudinal mesh further comprises a plurality of wide longitudinal segments with a second average length, a second average width, and a second average thickness; and wherein the second average width is at least 50% more than the first average width in the second configuration; wherein the second average width is at least twice the second average thickness in the second configuration; and wherein the second average length is at least equal to the first average length in the second configuration.

In an example, a first shape-changing embolic member and a second shape-changing embolic member can be part of a centrally-aligned sequence and/or series of two shape-changing embolic members which collectively occlude an aneurysm. In an example, a first shape-changing embolic member and a second shape-changing embolic member can be part of a centrally-aligned sequence and/or series of three shape-changing embolic members which collectively occlude an aneurysm. In an example, a first shape-changing embolic member and a second shape-changing embolic member can be part of a centrally-aligned sequence and/or series of four shape-changing embolic members which collectively occlude an aneurysm. In an example, a first shape-changing embolic member and a second shape-changing embolic member can be part of a centrally-aligned sequence and/or series of five or more shape-changing embolic members which collectively occlude an aneurysm.

In an example, a first shape-changing embolic member and a second shape-changing embolic member can be part of a centrally-aligned sequence of two shape-changing elliptical or toroidal embolic members which collectively occlude an aneurysm. In an example, a first shape-changing embolic member and a second shape-changing embolic member can be part of a centrally-aligned sequence of three shape-changing elliptical or toroidal embolic members which collectively occlude an aneurysm. In an example, a first shape-changing embolic member and a second shape-changing embolic member can be part of a centrally-aligned sequence of four shape-changing elliptical or toroidal embolic members which collectively occlude an aneurysm. In an example, a first shape-changing embolic member and a second shape-changing embolic member can be part of a centrally-aligned sequence of five or more shape-changing elliptical or toroidal embolic members which collectively occlude an aneurysm.

In an example, a flexible sac-filling portion of a device can have multiple longitudinal sections, undulations, bulges, or segments with different levels of porosity, flexibility, or tensile strength. In an example, a flexible sac-filling portion of a device can comprise a longitudinal sequence of centrally-connected sections, undulations, or bulges with different levels of porosity, flexibility, or tensile strength. In an example, a flexible sac-filling portion of a device can comprise a longitudinal sequence of two centrally-connected sections, undulations, or bulges with different levels of porosity, flexibility, or tensile strength. In an example, a flexible sac-filling portion of a device can comprise a longitudinal sequence of three centrally-connected sections, undulations, or bulges with different levels of porosity, flexibility, or tensile strength. In an example, a flexible sac-filling portion of a device can comprise a longitudinal sequence with distal, central, and proximal sections, undulations, or bulges which are centrally connected to each other with different levels of porosity, flexibility, or tensile strength. In an example, an intrasacular aneurysm occlusion device can comprise a longitudinal stack of centrally-connected embolic sections, undulations, or bulges with different levels of porosity, flexibility, or tensile strength. In an example, an intrasacular aneurysm occlusion device can comprise a longitudinal stack of two centrally-connected embolic sections, undulations, or bulges with different levels of porosity, flexibility, or tensile strength. In an example, an intrasacular aneurysm occlusion device can comprise a longitudinal stack of three centrally-connected embolic sections, undulations, or bulges with different levels of porosity, flexibility, or tensile strength.

In an example, a flexible sac-filling portion of a device can have a large-scale shape (with potential smaller-scale perimeter perturbations, blebs, or undulations) which is selected from the group consisting of: sphere; ellipsoid; cylinder; ring; egg shape; water drop shape; apple, pumpkin, onion, or pear shape; folded paper lantern shape; and torus. In an example, a flexible sac-filling portion of a device can have a shape which is spherical or elliptical on a large scale, but which can have perturbations, blebs, lobes, or undulations on a small scale.

In an example, a portion of a device can have multiple longitudinal sections, undulations, bulges, or segments with non-uniform porosity, flexibility, elasticity, or tensile strength. In an example, a device can comprise a longitudinal sequence of centrally-connected sections, undulations, or bulges with non-uniform porosity, flexibility, elasticity, or tensile strength. In an example, a device can comprise a longitudinal sequence of two centrally-connected sections, undulations, or bulges with non-uniform porosity, flexibility, elasticity, or tensile strength. In an example, a device can comprise a longitudinal sequence of three centrally-connected sections, undulations, or bulges with non-uniform porosity, flexibility, elasticity, or tensile strength. In an example, a device can comprise a longitudinal sequence with distal, central, and proximal sections, undulations, or bulges which are centrally connected to each other with non-uniform porosity, flexibility, elasticity, or tensile strength.

In an example, a proximal part of a flexible sac-filling portion can have multiple layers and a distal part of the flexible sac-filling portion can have a single layer. In an example, a flexible sac-filling portion of a device can have multiple longitudinal sections, undulations, bulges, or segments. In an example, a flexible sac-filling portion of a device can comprise a longitudinal sequence of centrally-connected sections, undulations, or bulges. In an example, a flexible sac-filling portion of a device can comprise a longitudinal sequence of two centrally-connected sections, undulations, or bulges. In an example, a flexible sac-filling portion of a device can comprise a longitudinal sequence of three centrally-connected sections, undulations, or bulges. In an example, a flexible sac-filling portion of a device can comprise a longitudinal sequence with distal, central, and proximal sections, undulations, or bulges which are centrally connected to each other. In an example, an intrasacular aneurysm occlusion device can comprise a longitudinal stack of centrally-connected embolic sections, undulations, or bulges. In an example, an intrasacular aneurysm occlusion device can comprise a longitudinal stack of two centrally-connected embolic sections, undulations, or bulges. In an example, an intrasacular aneurysm occlusion device can comprise a longitudinal stack of three centrally-connected embolic sections, undulations, or bulges.

In an example, an arcuate embolic structure can be a wire structure. In an example, an arcuate embolic structure can have a first orientation when it exits the aneurysm sac but then be compressed into a second orientation. In an example, the series of connected arcuate embolic structures can form a stack of connected arcuate embolic structures which share a common central axis within the aneurysm sac. In an example, the series of connected arcuate embolic structures can form a stack of connected arcuate embolic structures which share a common central axis within the aneurysm sac and fill a greater volume of the aneurysm sac than would be filled by a single hollow mesh structure with a similar size perimeter as the stack of connected arcuate embolic structures. In an example, at least one of the connected arcuate embolic structures can have a circumference that is larger than the circumference of the aneurysm neck in order to help keep the overall structure within the aneurysm sac. In an example, a series of connected arcuate embolic structures can form a longitudinally undulating and/or sinusoidal embolic stack within an aneurysm sac. In an example, an embolic structure deployed in an aneurysm sac can have undulating and/or sinusoidal variation in width. In an example, an embolic structure deployed in an aneurysm sac can comprise a longitudinally-undulating series of centrally-connected portions or sections.

In an example, an intrasacular aneurysm occlusion device can comprise a longitudinal stack of centrally-connected embolic sections, undulations, or bulges with non-uniform porosity, flexibility, elasticity, or tensile strength. In an example, an intrasacular aneurysm occlusion device can comprise a longitudinal stack of two centrally-connected embolic sections, undulations, or bulges with non-uniform porosity, flexibility, elasticity, or tensile strength. In an example, an intrasacular aneurysm occlusion device can comprise a longitudinal stack of three centrally-connected embolic sections, undulations, or bulges with non-uniform porosity, flexibility, elasticity, or tensile strength.

In an example, the longest axes of the plurality of shape-changing embolic members can be longitudinally and sequentially aligned in their first configurations and the longest axes of the plurality of shape-changing embolic members can be parallel to each other in their second configurations. In an example, a plurality of shape-changing embolic members are centrally-aligned. In an example, differences in the sizes and/or widths of a series of multiple shape-changing embolic members can be adjusted, controlled, and/or varied in real time by a person deploying them in order to best match the contours of a specific aneurysm sac.

In an example, an aneurysm occlusion device can comprise: a generally spherical (wire and/or polymer) mesh (or net) which is inserted into an aneurysm sac; wherein the generally spherical mesh has a first elasticity level; wherein the generally spherical mesh (or net) centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the generally spherical mesh and/or disk or ellipsoidal shaped mesh are filled with embolic material (such as microsponges, hydrogels, or coils).

In an example, an aneurysm occlusion device can comprise: a generally spherical (wire and/or polymer) mesh (or net) which is inserted into an aneurysm sac; wherein the generally spherical mesh has a first elasticity level; wherein the generally spherical mesh centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; wherein the disk or ellipsoidal shaped mesh is (centrally) connected to the generally spherical mesh; and wherein the generally spherical mesh and/or the disk or ellipsoidal shaped mesh are filled with embolic material (such as microsponges, hydrogels, or coils). Relevant example variations discussed elsewhere in this disclosure or priority-linked disclosures can also be applied to this example.

Figure 7:
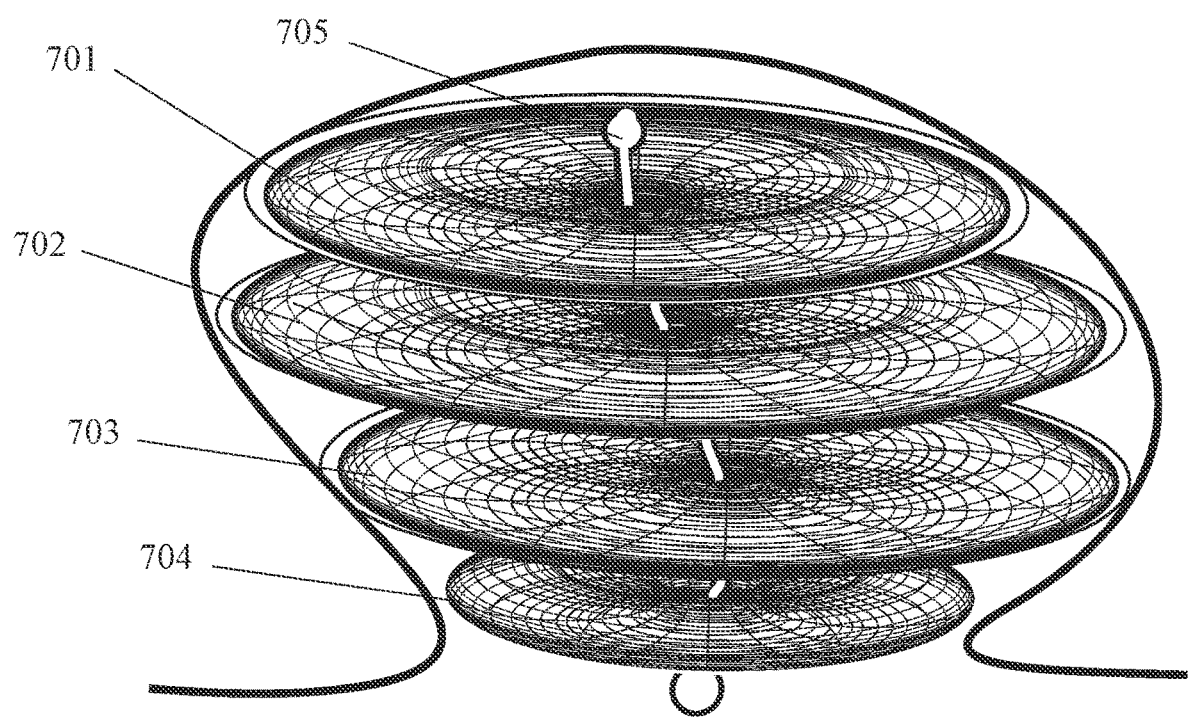
FIG. 7 shows an aneurysm occlusion device with a plurality of connected radial structures along its proximal-to-distal longitudinal axis.

FIG. 7 shows an example of a intrasacular aneurysm occlusion device comprising: a series of at least three arcuate three-dimensional stents (four in this example —701, 702, 703, and 704) which is deployed within an aneurysm sac, wherein the arcuate three-dimensional stents in the series are connected to each other by a connector 705; and wherein the arcuate three-dimensional stents in the series have first compressed configurations as they travel within a catheter and second expanded configurations after they are delivered from the catheter into an aneurysm sac. In an example, arcuate three-dimensional stents in the series can be centrally connected to each other. In an example, the centroids of arcuate three-dimensional stents in the series can be (pair-wise) attached to each other by a central connector. In an example, the shape of an arcuate three-dimensional stent can be selected from the group consisting of: apple shape; bowl shape; compressed-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus.

A series of at three arcuate three-dimensional stents can comprise three radial structures along a proximal-to-distal longitudinal axis of a device. In an example, these three radial structures can comprise proximal, central, and distal radial lobes. As shown in FIG. 7, proximal, central, and distal radial lobes can have different sizes. As shown in FIG. 7, a central lobe can be larger than proximal and distal lobes. in a longitudinal series can have different shapes selected from the group consisting of: apple shape; bowl shape; compressed-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus. In an example, a central lobe can have a compressed-sphere shape. In an example, proximal and distal lobes can have rounded disk or Frisbee shapes.

In accordance with the above discussion, an intrasacular aneurysm occlusion device can comprise: a mesh or net (e.g. mesh, net, shell, or stent) with a plurality of radial lobes along its proximal-to-distal longitudinal axis which is configured to be inserted and expanded within an aneurysm sac, wherein the mesh or net further comprises: a central lobe; a proximal lobe which extends proximally from the middle mesh lobe to span the aneurysm neck; and a distal lobe which extends distally from the middle lobe toward the aneurysm dome, wherein the proximal lobe has a different shape and a smaller size than the central lobe, and wherein the distal lobe has a different shape and a smaller size than the central lobe.

In an example, the shapes of the proximal and distal lobes can be more longitudinally-compressed than the shape of the middle lobe. In an example, a central lobe can have a generally globular (e.g. spherical, oblate spherical or ellipsoidal) shape and proximal and distal lobes can have rounded disk, oblate spheroid, or Frisbee shapes. As shown in FIG. 7, the size of a central lobe can be greater than the size of a proximal lobe or a distal lobe. In an example, the proximal, central, and distal lobes can collectively form: a "lantern shape" (e.g. like the Green Lantern symbol from the comic book character or a folded paper lantern); and/or a "TIE fighter shape" (e.g. like the craft that Darth Vader piloted in the first Star Wars movie). In this example, different lobes are different structures which have been connected together. In another example, the proximal, central, and distal lobes can be portions, sections, and/or lobes of the same (tubular) mesh structure which has been radially-constrained.

In an example, a first shape-changing embolic member and a second shape-changing embolic member can be part of a centrally-aligned sequence and/or series of two shape-changing embolic members which collectively occlude an aneurysm. In an example, a first shape-changing embolic member and a second shape-changing embolic member can be part of a centrally-aligned sequence and/or series of three shape-changing embolic members which collectively occlude an aneurysm. In an example, a first shape-changing embolic member and a second shape-changing embolic member can be part of a centrally-aligned sequence and/or series of four shape-changing embolic members which collectively occlude an aneurysm. In an example, a first shape-changing embolic member and a second shape-changing embolic member can be part of a centrally-aligned sequence and/or series of five or more shape-changing embolic members which collectively occlude an aneurysm.

In an example, a first shape-changing embolic member and a second shape-changing embolic member can be part of a centrally-aligned sequence of two shape-changing elliptical or toroidal embolic members which collectively occlude an aneurysm. In an example, a first shape-changing embolic member and a second shape-changing embolic member can be part of a centrally-aligned sequence of three shape-changing elliptical or toroidal embolic members which collectively occlude an aneurysm. In an example, a first shape-changing embolic member and a second shape-changing embolic member can be part of a centrally-aligned sequence of four shape-changing elliptical or toroidal embolic members which collectively occlude an aneurysm. In an example, a first shape-changing embolic member and a second shape-changing embolic member can be part of a centrally-aligned sequence of five or more shape-changing elliptical or toroidal embolic members which collectively occlude an aneurysm.

In an example, a first shape-changing embolic member can have a shape in its second configuration which is selected from the group consisting of: ellipsoid, paraboloid, sphere, disk, cylinder, ovaloid, convex lens, wheel, tire, doughnut, and torus. In an example, a first shape-changing embolic member can have a cross-sectional shape in the X-Z plane in its second configuration which is selected from the group consisting of: ellipse, reflected parabola, circle, oval, convex lens, and torus. In an example, a second shape-changing embolic member can have a shape in its fourth configuration which is selected from the group consisting of: ellipsoid, paraboloid, sphere, disk, cylinder, ovaloid, convex lens, wheel, tire, doughnut, and torus. In an example, a second shape-changing embolic member can have a cross-sectional shape in the XX-ZZ plane in its fourth configuration which is selected from the group consisting of: ellipse, reflected parabola, circle, oval, convex lens, and torus.

In an example, a plurality of shape-changing embolic members can share a common central axis within an aneurysm sac. In an example, a plurality of shape-changing embolic members can form a stack of connected ellipsoid disks which share a common central axis within the aneurysm sac. In an example, a stack of connected ellipsoids can fill a greater volume of the aneurysm sac than would be filled by a single hollow-mesh structure (such as a wire-mesh single sphere or ellipsoid that is expanded with an aneurysm sac) with a similar-size perimeter as the combined stack of connected ellipsoid disks. In an example, at least one of the connected ellipsoids has a circumference that is larger than the circumference of the aneurysm neck in order to help keep the stack within the aneurysm sac.

In an example, the sizes of first and second shape-changing embolic members can be the same. In an example, the shapes of first and second shape-changing embolic members can be the same. In an example, the sizes of first and second shape-changing embolic members can be different. In an example, the shapes of first and second shape-changing embolic members can be different. In an example, a first shape-changing embolic member can have a circumference in its second configuration that is larger than the circumference of an aneurysm neck in order to keep it within the aneurysm sac. In an example, a second shape-changing embolic member can have a circumference in its fourth configuration that is larger than the circumference of an aneurysm neck in order to keep it within the aneurysm sac.

The size of a second shape-changing embolic member can be greater than the size of a first shape-changing embolic member. The shape of a second shape-changing embolic member can be different than the shape of a first shape-changing embolic member. In an example, a distal-to-proximal sequence of multiple shape-changing embolic members can be progressively larger and/or wider as they are sequentially deployed in an aneurysm. In an example, a distal-to-proximal sequence of multiple shape-changing embolic members can first be progressively larger and/or wider and then progressively smaller and/or narrower as they are sequentially deployed in an aneurysm. In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac.

In an example, a device for occluding an aneurysm can comprise: a multiple-width longitudinal mesh which is configured to be inserted into an aneurysm sac; wherein the multiple-width longitudinal mesh has a distal-to-proximal longitudinal axis prior to insertion into the aneurysm sac, wherein the multiple-width longitudinal mesh has a length dimension along (or parallel to) the distal-to-proximal longitudinal axis, wherein the multiple-width longitudinal mesh has a width dimension perpendicular (or orthogonal) to the length dimension, and wherein the multiple-width longitudinal mesh has a thickness dimension perpendicular (or orthogonal) to the length dimension and the width dimension; wherein the multiple-width longitudinal mesh further comprises a plurality of narrow longitudinal segments with a first average length, a first average width, and a first average thickness; wherein the multiple-width longitudinal mesh further comprises a plurality of wide longitudinal segments with a second average length, a second average width, and a second average thickness; and wherein the second average width is at least 50% more than the first average width, wherein the second average width is at least twice the second average thickness, wherein the second average length is at least equal to the first average length, and wherein these three dimensional comparisons are made after the multiple-width longitudinal mesh has been inserted into the aneurysm sac.

In an example, a device for occluding an aneurysm can comprise: a multiple-width longitudinal mesh which is configured to be inserted into an aneurysm sac; wherein the multiple-width longitudinal mesh has a first configuration prior to insertion into the aneurysm sac and a second configuration after insertion into aneurysm sac; wherein the multiple-width longitudinal mesh has a distal-to-proximal longitudinal axis in the first configuration; wherein the multiple-width longitudinal mesh has a length dimension along (or parallel to) the distal-to-proximal longitudinal axis, wherein the multiple-width longitudinal mesh has a width dimension perpendicular (or orthogonal) to the length dimension, and wherein the multiple-width longitudinal mesh has a thickness dimension perpendicular (or orthogonal) to the length dimension and the width dimension; wherein the multiple-width longitudinal mesh further comprises a plurality of narrow longitudinal segments with a first average length, a first average width, and a first average thickness; wherein the multiple-width longitudinal mesh further comprises a plurality of wide longitudinal segments with a second average length, a second average width, and a second average thickness; and wherein the second average width is at least 50% more than the first average width in the second configuration; wherein the second average width is at least twice the second average thickness in the second configuration; and wherein the second average length is at least equal to the first average length in the second configuration.

In an example, a first shape-changing embolic member and a second shape-changing embolic member can be part of a centrally-aligned sequence and/or series of two shape-changing embolic members which collectively occlude an aneurysm. In an example, a first shape-changing embolic member and a second shape-changing embolic member can be part of a centrally-aligned sequence and/or series of three shape-changing embolic members which collectively occlude an aneurysm. In an example, a first shape-changing embolic member and a second shape-changing embolic member can be part of a centrally-aligned sequence and/or series of four shape-changing embolic members which collectively occlude an aneurysm.

In an example, a first shape-changing embolic member and a second shape-changing embolic member can be part of a centrally-aligned sequence and/or series of five or more shape-changing embolic members which collectively occlude an aneurysm.

In an example, a first shape-changing embolic member and a second shape-changing embolic member can be part of a centrally-aligned sequence of two shape-changing elliptical or toroidal embolic members which collectively occlude an aneurysm. In an example, a first shape-changing embolic member and a second shape-changing embolic member can be part of a centrally-aligned sequence of three shape-changing elliptical or toroidal embolic members which collectively occlude an aneurysm. In an example, a first shape-changing embolic member and a second shape-changing embolic member can be part of a centrally-aligned sequence of four shape-changing elliptical or toroidal embolic members which collectively occlude an aneurysm. In an example, a first shape-changing embolic member and a second shape-changing embolic member can be part of a centrally-aligned sequence of five or more shape-changing elliptical or toroidal embolic members which collectively occlude an aneurysm.

In an example, a flexible sac-filling portion of a device can have multiple longitudinal sections, undulations, bulges, or segments with different levels of porosity, flexibility, or tensile strength. In an example, a flexible sac-filling portion of a device can comprise a longitudinal sequence of centrally-connected sections, undulations, or bulges with different levels of porosity, flexibility, or tensile strength. In an example, a flexible sac-filling portion of a device can comprise a longitudinal sequence of two centrally-connected sections, undulations, or bulges with different levels of porosity, flexibility, or tensile strength. In an example, a flexible sac-filling portion of a device can comprise a longitudinal sequence of three centrally-connected sections, undulations, or bulges with different levels of porosity, flexibility, or tensile strength. In an example, a flexible sac-filling portion of a device can comprise a longitudinal sequence with distal, central, and proximal sections, undulations, or bulges which are centrally connected to each other with different levels of porosity, flexibility, or tensile strength. In an example, an intrasacular aneurysm occlusion device can comprise a longitudinal stack of centrally-connected embolic sections, undulations, or bulges with different levels of porosity, flexibility, or tensile strength. In an example, an intrasacular aneurysm occlusion device can comprise a longitudinal stack of two centrally-connected embolic sections, undulations, or bulges with different levels of porosity, flexibility, or tensile strength. In an example, an intrasacular aneurysm occlusion device can comprise a longitudinal stack of three centrally-connected embolic sections, undulations, or bulges with different levels of porosity, flexibility, or tensile strength.

In an example, a flexible sac-filling portion of a device can have a large-scale shape (with potential smaller-scale perimeter perturbations, blebs, or undulations) which is selected from the group consisting of: sphere; ellipsoid; cylinder; ring; egg shape; water drop shape; apple, pumpkin, onion, or pear shape; folded paper lantern shape; and torus. In an example, a flexible sac-filling portion of a device can have a shape which is spherical or elliptical on a large scale, but which can have perturbations, blebs, lobes, or undulations on a small scale.

In an example, a portion of a device can have multiple longitudinal sections, undulations, bulges, or segments with non-uniform porosity, flexibility, elasticity, or tensile strength. In an example, a device can comprise a longitudinal sequence of centrally-connected sections, undulations, or bulges with non-uniform porosity, flexibility, elasticity, or tensile strength. In an example, a device can comprise a longitudinal sequence of two centrally-connected sections, undulations, or bulges with non-uniform porosity, flexibility, elasticity, or tensile strength. In an example, a device can comprise a longitudinal sequence of three centrally-connected sections, undulations, or bulges with non-uniform porosity, flexibility, elasticity, or tensile strength. In an example, a device can comprise a longitudinal sequence with distal, central, and proximal sections, undulations, or bulges which are centrally connected to each other with non-uniform porosity, flexibility, elasticity, or tensile strength.

In an example, a proximal part of a flexible sac-filling portion can have multiple layers and a distal part of the flexible sac-filling portion can have a single layer. In an example, a flexible sac-filling portion of a device can have multiple longitudinal sections, undulations, bulges, or segments. In an example, a flexible sac-filling portion of a device can comprise a longitudinal sequence of centrally-connected sections, undulations, or bulges. In an example, a flexible sac-filling portion of a device can comprise a longitudinal sequence of two centrally-connected sections, undulations, or bulges. In an example, a flexible sac-filling portion of a device can comprise a longitudinal sequence of three centrally-connected sections, undulations, or bulges. In an example, a flexible sac-filling portion of a device can comprise a longitudinal sequence with distal, central, and proximal sections, undulations, or bulges which are centrally connected to each other. In an example, an intrasacular aneurysm occlusion device can comprise a longitudinal stack of centrally-connected embolic sections, undulations, or bulges. In an example, an intrasacular aneurysm occlusion device can comprise a longitudinal stack of two centrally-connected embolic sections, undulations, or bulges. In an example, an intrasacular aneurysm occlusion device can comprise a longitudinal stack of three centrally-connected embolic sections, undulations, or bulges.

In an example, an arcuate embolic structure can be a wire structure. In an example, an arcuate embolic structure can have a first orientation when it exits the aneurysm sac but then be compressed into a second orientation. In an example, the series of connected arcuate embolic structures can form a stack of connected arcuate embolic structures which share a common central axis within the aneurysm sac. In an example, the series of connected arcuate embolic structures can form a stack of connected arcuate embolic structures which share a common central axis within the aneurysm sac and fill a greater volume of the aneurysm sac than would be filled by a single hollow mesh structure with a similar size perimeter as the stack of connected arcuate embolic structures. In an example, at least one of the connected arcuate embolic structures can have a circumference that is larger than the circumference of the aneurysm neck in order to help keep the overall structure within the aneurysm sac. In an example, a series of connected arcuate embolic structures can form a longitudinally undulating and/or sinusoidal embolic stack within an aneurysm sac. In an example, an embolic structure deployed in an aneurysm sac can have undulating and/or sinusoidal variation in width. In an example, an embolic structure deployed in an aneurysm sac can comprise a longitudinally-undulating series of centrally-connected portions or sections.

In an example, an intrasacular aneurysm occlusion device can comprise a longitudinal stack of centrally-connected embolic sections, undulations, or bulges with non-uniform porosity, flexibility, elasticity, or tensile strength. In an example, an intrasacular aneurysm occlusion device can comprise a longitudinal stack of two centrally-connected embolic sections, undulations, or bulges with non-uniform porosity, flexibility, elasticity, or tensile strength. In an example, an intrasacular aneurysm occlusion device can comprise a longitudinal stack of three centrally-connected embolic sections, undulations, or bulges with non-uniform porosity, flexibility, elasticity, or tensile strength.

In an example, the longest axes of the plurality of shape-changing embolic members can be longitudinally and sequentially aligned in their first configurations and the longest axes of the plurality of shape-changing embolic members can be parallel to each other in their second configurations. In an example, a plurality of shape-changing embolic members are centrally-aligned. In an example, differences in the sizes and/or widths of a series of multiple shape-changing embolic members can be adjusted, controlled, and/or varied in real time by a person deploying them in order to best match the contours of a specific aneurysm sac.

In an example, an aneurysm occlusion device can comprise: a generally spherical (wire and/or polymer) mesh (or net) which is inserted into an aneurysm sac; wherein the generally spherical mesh has a first elasticity level; wherein the generally spherical mesh (or net) centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; and wherein the generally spherical mesh and/or disk or ellipsoidal shaped mesh are filled with embolic material (such as microsponges, hydrogels, or coils).

In an example, an aneurysm occlusion device can comprise: a generally spherical (wire and/or polymer) mesh (or net) which is inserted into an aneurysm sac; wherein the generally spherical mesh has a first elasticity level; wherein the generally spherical mesh centroid is a first distance from the aneurysm neck; and an ellipsoidal (wire) mesh inserted into the aneurysm sac; wherein the disk or ellipsoidal shaped mesh has a second elasticity level which is less than the first elasticity level; wherein the disk or ellipsoidal shaped mesh centroid is a second distance from the aneurysm neck; wherein the second distance is less than the first distance; wherein the disk or ellipsoidal shaped mesh spans the aneurysm neck; wherein the disk or ellipsoidal shaped mesh is (centrally) connected to the generally spherical mesh; and wherein the generally spherical mesh and/or the disk or ellipsoidal shaped mesh are filled with embolic material (such as microsponges, hydrogels, or coils). Relevant example variations discussed elsewhere in this disclosure or priority-linked disclosures can also be applied to this example.

Figure 8:
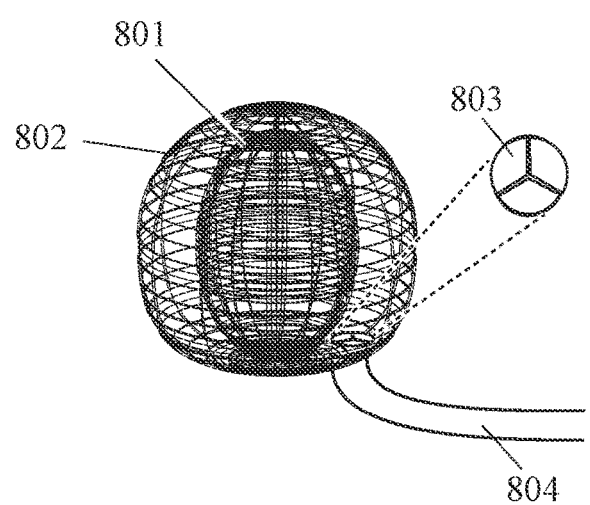
FIG. 8 shows an aneurysm occlusion device with a globular outer mesh and a globular inner mesh inside the outer mesh or net.

FIG. 8 shows an example of a intrasacular aneurysm occlusion device comprising: an inner convex mesh 801 which is configured to be radially-expanded within an aneurysm; an outer convex mesh (or net) 802 which is configured to be radially-expanded within the aneurysm, wherein the inner convex mesh is inside the outer convex mesh; a valve 803 in the outer convex mesh (or net); and a catheter 804 through which embolic members (e.g. coils, hydrogels, microsponges, beads, or string-of-pearls strands) are inserted into the space between the inner convex mesh and the outer convex mesh. After the embolic members have been inserted, the valve is closed and the catheter is removed.

As shown in FIG. 8, an intrasacular aneurysm occlusion device can comprise one mesh (e.g. mesh, net, shell, or stent) inside another mesh (e.g. mesh, net, shell, or stent). As discussed above, a mesh (e.g. mesh, net, shell, or stent) can have a shape which is selected from the group consisting of: apple shape; bowl shape; compress-sphere shape; cylinder; disk; doughnut shape; egg shape; ellipsoid; Frisbee™ shape; frustum; hourglass shape; oval; peanut shape; pear shape; pumpkin shape; ring shape; Saturn shape; sphere; tire shape; and torus. In an example, an outer convex shell can have a spherical, oblate spherical, or ellipsoidal shape. In an example, an inner convex shell can have a toroidal shape. A toroidal shape comprises an outer globular perimeter with a central columnar hole, so a device with a toroidal shell inside a globular (e.g. spherical, oblate spherical, or ellipsoidal) shell collectively forms a first globular shell, a second globular shell inside the first globular shell, and a central columnar mesh inside the second globular shell.

In accordance with the above discussion, an intrasacular aneurysm occlusion device can comprise: a globular (e.g. spherical, oblate spherical, or ellipsoidal) outer mesh or net (e.g. mesh, net, shell, or stent) which is configured to be inserted and expanded within an aneurysm sac; a globular (e.g. spherical, oblate spherical, or ellipsoidal) inner mesh or net e.g. mesh, net, shell, or stent) which is inside the outer mesh or net; and a central column (e.g. column, cylinder, tube, or lumen) along a proximal-to-distal longitudinal axis of the inner mesh or net.

As shown in FIG. 8, the inner mesh or net is connected to a proximal portion (e.g. proximal hub) of the outer mesh or net. In another example, an inner mesh or net can be connected to a distal portion (e.g. distal hub) of the outer mesh or net. In an example, there can be a central proximal opening in one or more of the meshes through which embolic material (e.g. coils, embolic liquid, string-of-pearls embolic strands, or embolic pieces) can be inserted. In an example, embolic material can be inserted through the central column.

In an example, the width (e.g. cross-sectional diameter) of the central column can be between 5% and 20% of the width (e.g. cross-sectional diameter) of the inner mesh or net. In an example, the width (e.g. cross-sectional diameter) of the central column can be between 5% and 20% of the width (e.g. cross-sectional diameter) of the outer mesh or net. In an example, the width (e.g. cross-sectional diameter) of the central column can be between 10% and 30% of the width (e.g. cross-sectional diameter) of the inner mesh or net. In an example, the width (e.g. cross-sectional diameter) of the central column can be between 10% and 30% of the width (e.g. cross-sectional diameter) of the outer mesh or net. In an example, the outer mesh, the inner mesh, and the central column can be portions, sections, and/or lobes of the same (tubular) mesh structure which has been radially-constrained, inverted, and/or everted.

In an example, an aneurysm occlusion device can comprise: a longitudinal lumen that is inserted into the parent blood vessel of an aneurysm; a flexible expandable member (such as a net or mesh) which is expanded within the aneurysm sac by the insertion of embolic members into that flexible expandable member; and a resilient expandable member (such as a cylindrical stent or ring stent) that is attached to a central portion of the flexible expandable member and expanded within the aneurysm sac in order to keep the flexible expandable member from slipping out of the aneurysm sac.

In an example, a resilient wider-than-neck portion and a flexible sac-filling portion can be different parts of the same continuous intrasacular occlusion device, but have different properties. In an example, the proximal portion of this intrasacular occlusion device can comprise a resilient wider-than-neck portion with a first density level and a distal portion of this intrasacular occlusion device can comprise a flexible sac-filling portion with a second density level, wherein the second level is less than the first level. In an example, the proximal portion of an intrasacular occlusion device can comprise a resilient wider-than-neck portion with a first elasticity level and a distal portion of this intrasacular occlusion device can comprise a flexible sac-filling portion with a second elasticity level, wherein the second level is greater than the first level. In an example, the proximal portion of an intrasacular occlusion device can comprise a resilient wider-than-neck portion with a first flexibility level and a distal portion of this intrasacular occlusion device can comprise a flexible sac-filling portion with a second flexibility level, wherein the second level is greater than the first level. In an example, a resilient wider-than-neck portion and a flexible sac-filling portion can be nested. In an example, resilient wider-than-neck portion and a flexible sac-filling portion can be concentric.

In an example, a resilient wider-than-neck portion of a device and a flexible sac-filling portion of a device can be (longitudinally) coaxial in their first configurations. In an example, a resilient wider-than-neck portion of a device and a flexible sac-filling portion of a device can be (longitudinally) co-linear in their first configurations. In an example, a flexible sac-filling portion can be folded or pleated so as to have multiple layers in its first configuration and be expanded so as to have a single layer in its second configuration.

In an example, a resilient wider-than-neck portion of a device and a flexible sac-filling portion of a device can be coaxial but not nested in their first configurations. In an example, a resilient wider-than-neck portion of a device and a flexible sac-filling portion of a device can be both coaxial and nested in their second configurations. In an example, a flexible sac-filling portion of a device can overlap a resilient wider-than-neck portion of a device. In an example, a resilient wider-than-neck portion of a device can be separate from, but nested within, a flexible sac-filling portion of a device. In an example, a flexible sac-filling portion and a resilient wider-than-neck portion can be concentric. In an example, a concave proximal surface of a flexible sac-filling portion of a device can fit into a convex distal surface of a resilient wider-than-neck portion of a device in their second configurations. In an example, expansion of the proximal surface of a flexible sac-filling portion can be constrained by the distal surface of a resilient wider-than-neck portion and the distal surface of a flexible sac-filling portion can be constrained by aneurysm walls.

In an example, a resilient wider-than-neck portion of a device can have multiple layers. In an example, a plurality of layers can fit into each other in nested manner, creating a multi-layer portion of a device which spans and occludes an aneurysm neck from inside the aneurysm sac. In an example, a resilient wider-than-neck portion can comprise a multi-layer bowl or hemisphere, a multi-layer sphere or ball, a multi-layer ellipsoid or ovaloid, a multi-layer torus or ring, or a multi-layer disk. In an example, a portion can have a metal layer and a polymer layer. In an example, an inner layer can be metal and an outer layer can be made from a polymer. In an example, a resilient wider-than-neck portion of a device can have a biologically-active outer layer which encourages cell growth for more thorough embolization of the aneurysm neck. In an example, a resilient wider-than-neck portion can have multiple layers of material with different mesh or braid directions, different porosity levels, different elasticity levels, and/or different rigidity levels.

In an example, a resilient wider-than-neck portion of a device can have a single layer in its first configuration and multiple layers in its second configuration. In an example, a resilient wider-than-neck portion of a device can be folded and/or curved back on itself in its second configuration so as to have multiple layers in its second configuration. In an example, the proximal part of a resilient wider-than-neck portion of a device can have a single layer as it is transported through a delivery lumen to an aneurysm sac and can have two overlapping layers after it is released from the lumen. In an example, it can be folded after expansion within the aneurysm sac. In an example, a resilient wider-than-neck portion of a device can be a mesh, net, lattice, or braid whose proximal part comprises a single layer in it first configuration (as it is transported through a delivery lumen to an aneurysm sac) and two or more overlapping layers in its second configuration (after the resilient wider-than-neck portion is released from the lumen and deployed within the aneurysm sac).

In an example, a resilient wider-than-neck portion of a device can be inside a flexible sac-filling portion of a device. In an example, a flexible sac-filling portion of a device can surround a resilient wider-than-neck portion of a device. In an example, the proximal surface of a flexible sac-filling portion of a device can overlap the distal surface of a resilient wider-than-neck portion of a device. In an example, a resilient wider-than-neck portion of a device can be inside a proximal area of a flexible sac-filling portion of a device. In an example, the proximal surface of a flexible sac-filling portion of a device can overlap the proximal surface of a resilient wider-than-neck portion of a device. In an example, a flexible sac-filling portion can overlap a resilient wider-than-neck portion, especially in their second configurations. In an example, the distal surface of a resilient wider-than-neck portion of a device and the proximal surface of a flexible sac-filling portion of a device may not overlap in their first configurations (as they are transported through a delivery lumen to an aneurysm sac) but do overlap in their second configurations (after they are released from the lumen and expanded within the aneurysm sac).

In an example, a resilient wider-than-neck portion of a device can have an opening through which embolic members are inserted into the flexible sac-filling portion of a device. In an example, this opening can have a one-way valve which enables embolic members to be inserted into the flexible sac-filling portion of a device but not escape out. In an example, this opening can be closed after the sac-filling portion has been expanded. In an example, a resilient wider-than-neck portion of a device can have one or more adjustable openings. In an example, these openings can allow blood to escape from an aneurysm sac (as the resilient wider-than-neck portion and/or the flexible sac-filling portion are being expanded within the aneurysm sac), but then be closed to prevent blood from re-entering the aneurysm sac. In an example, an opening can be manually and/or remotely changed from a first (open) configuration to a second (closed) configuration. In an example, a resilient wider-than-neck portion can have two openings: a first opening through which embolic material is inserted into the aneurysm sac and a second opening through which blood can exit the aneurysm sac while embolic material is being inserted into the aneurysm sac. In an example, the device can further comprise a closure mechanism (which closes an opening) selected from the group consisting of: tensile ring; drawstring; electromagnetic melting mechanism; insertable plug; clamp; hydrogel plug; and bioactive congealing plug.

In an example, an intrasacular aneurysm occlusion device can comprise: a net or mesh which is configured to be expanded within an aneurysm sac, wherein the net or mesh is expanded by being filled with a plurality of embolic members, wherein the net or mesh conforms to the walls of the aneurysm sac after it has been expanded, and wherein the net or mesh has a first elastic modulus; and a stent which is configured to be expanded within the aneurysm sac, wherein the stent is expanded inside the proximal half of the net or mesh, wherein the stent has an ellipsoidal or toroidal shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: (1) an intravascular delivery lumen; (2) a plurality of embolic members; (3) a inner stent; wherein the inner stent is configured to occlude the neck of an aneurysm sac; wherein the inner stent has a first configuration while it is being transported through the delivery lumen to an aneurysm sac and a second configuration after it has been expanded within the aneurysm sac; wherein the inner stent in its second configuration has a width which is greater than the diameter of the neck of the aneurysm sac; and wherein the inner stent in its second configuration has a first level of flexibility, elasticity, and/or malleability; and (4) a outer net or mesh; wherein the net or mesh has a first configuration while it is being transported through the delivery lumen to an aneurysm sac; wherein the net or mesh has a second configuration after it has been expanded within the aneurysm sac; wherein the net or mesh is configured to conform to the walls of an aneurysm sac in its second configuration; wherein the net or mesh is expanded from its first configuration to its second configuration by the insertion of the embolic members into the net or mesh; wherein the net or mesh in its second configuration has a second level of flexibility, elasticity, and/or malleability which is greater than the first level of flexibility, elasticity, and/or malleability.

In an example, the centers of flexible sac-filling and resilient wider-than-neck portions of a device can be attached to each other. In an example, a flexible sac-filling portion can be centrally aligned with a resilient wider-than-neck portion. In an example, a flexible sac-filling portion and a resilient wider-than-neck portion can be longitudinally aligned. In an example, a flexible sac-filling portion can be attached to the distal end of resilient wider-than-neck portion. In an example, a resilient wider-than-neck portion can be attached to the proximal end of a flexible sac-filling portion. In an example, the proximal surface of a flexible sac-filling portion can be attached to the distal surface of a resilient wider-than-neck portion. In an example, the lateral perimeters of flexible sac-filling and resilient wider-than-neck portions of a device can be attached to each other.

In different embodiments of a device, the resilient wider-than-neck and flexible sac-filling portions of a device can have different locations relative to each other and to an aneurysm sac. In an example, one portion can be more proximal (e.g. closer to the aneurysm neck) than the other portion. In an example, one portion can be inside the other portion. In an example, a resilient wider-than-neck portion of a device in its second configuration can be proximal relative to a flexible sac-filling portion of a device in its second configuration, wherein proximal is defined as closer to the aneurysm neck and distal is defined as closer to the top of the aneurysm dome. In an example, a resilient wider-than-neck portion of a device can be inside (e.g. nested within) a flexible sac-filling portion of a device. Alternatively, a flexible sac-filling portion of a device can be inside (e.g. nested within) a resilient wider-than-neck portion of a device. In an example, a resilient wider-than-neck portion of a device in its second configuration can be central relative to a flexible sac-filling portion of a device in its second configuration, wherein central is defined as closer to the centroid of the aneurysm sac and peripheral is defined as closer to the walls of the aneurysm sac. In an example, a resilient wider-than-neck portion of a device in its second configuration can be peripheral relative to a flexible sac-filling portion of a device in its second configuration.

There can also be differences among example embodiments of a device in whether the resilient wider-than-neck and flexible sac-filling portions of a device are separate structures or are portions of the same structure. In an example, resilient wider-than-neck and flexible sac-filling portions of a device can be separate structures. In an example, resilient wider-than-neck and flexible sac-filling portions of a device can be formed as separate structures, but can then be attached to each other at one or more points. In an example, resilient wider-than-neck and flexible sac-filling portions of a device can be different portions of the same structure. In an example, resilient wider-than-neck and flexible sac-filling portions of a device can be proximal and distal portions, respectively, of the same structure. In an example, resilient wider-than-neck and flexible sac-filling portions of a device can be proximal and distal portions, respectively, of a single continuous structure. In an example, resilient wider-than-neck and flexible sac-filling portions of a device can be inner and outer portions or layers, respectively, of the same structure. In an example, resilient wider-than-neck and flexible sac-filling portions of a device can be inner and outer portions or layers, respectively, of the same continuous structure.

In an example, a proximal portion of a distal mesh can fit inside a distal concavity of a proximal mesh. In an example, a proximal portion of a distal mesh can be nested within a distal concavity of a proximal mesh. In an example, a proximal mesh can overlap a proximal portion of a distal mesh. In an example, between 20% and 40% of the surface of a distal mesh can be nested within a concavity of a proximal mesh. In an example, between 30% and 66% of the surface of a distal mesh can be nested within a concavity of a proximal mesh. In an example, distal and proximal meshes can be coaxial. In an example, the distal mesh and the proximal mesh can share a common longitudinal axis. In an example, a proximal portion of a distal mesh can be attached to a proximal mesh. In an example, a proximal portion of a distal mesh can be fused to a portion of the proximal mesh by the application of electromagnetic energy. In an example, a proximal portion of a distal mesh can be attached to a portion of a proximal mesh by a wire, string, suture, or other filament.

In an example, a toroidal mesh can be the outer surface of a torus. This is analogous to the outer surface of a bagel. Following this analogy, the central opening in the toroidal mesh is analogous to the hole in a bagel, although probably not as relatively large as the hole in a bagel. In an example, the cross-sectional area of the central opening in the toroidal mesh can be between 5% to 15% of the maximum cross-sectional area of the toroidal mesh. In an example, the cross-sectional area of the central opening in the toroidal mesh can be between 10% to 30% of the maximum cross-sectional area of the toroidal mesh. In an example, a toroidal mesh can be created geometrically by rotating a circle or ellipse around a vertical axis (in space) which is to the right or left of the circle or ellipse. In an example, the opening can have a hyperbolic cross-section. In an example, a toroidal mesh can radially expand within the aneurysm sac to a width which is greater than the width of the aneurysm neck.

In an example, an inner convex mesh can be spherical. In an example, an inner convex mesh can be ellipsoidal. In an example, an inner convex mesh can be apple, barrel, or pear shaped. In an example, an inner convex mesh can be toroidal. In an example, an inner convex mesh can be hyperbolic, dumbbell, peanut, or hour-glass shaped. In an example, an inner convex mesh can be disk shaped. In an example, an inner convex mesh can be shaped like a paper lantern. In an example, an inner convex mesh can be a wire mesh and/or frame. In an example, an inner convex mesh can be a woven or braided wire mesh and/or frame. In an example, an inner convex mesh can be made from metal and polymer components. In an example, an outer convex mesh (or net) can be spherical. In an example, an outer convex mesh can be ellipsoidal. In an example, an outer convex mesh can be apple, barrel, or pear shaped. In an example, an outer convex mesh can be shaped like a paper lantern. In an example, an outer convex mesh can be a wire mesh and/or frame. In an example, an outer convex mesh can be a woven or braided wire mesh and/or frame.

In an example, an outer convex mesh (or net) can be made from metal and polymer components. In an example, an inner convex mesh can be made from a metal and an outer convex mesh can be made from a polymer. In an example, inner and outer convex meshes can be nested. In an example, inner and outer convex meshes can be concentric. In an example, inner and outer convex meshes can be attached to each other. In an example, the proximal ends of inner and outer convex meshes can be attached to each other. In an example, the distal ends of inner and outer convex meshes can be attached to each other. In an example: the proximal ends of inner and outer convex meshes can be attached to each other; and the distal ends of inner and outer convex meshes can be attached to each other.

In an example, there can be an opening and/or lumen through a proximal stent through which embolic members and/or material is inserted into the flexible net or mesh. In an example, this opening and/or lumen can be centrally-located with respect to the proximal surface of the proximal stent. In an example, this opening and/or lumen can be centrally-located with respect to the longitudinal axis of the proximal stent. In an example, this opening and/or lumen can be an opening and/or lumen through a hub into which proximal ends of braided wires or tubes of the stent are bound or attached. In an example, this opening and/or lumen can be off-axial with respect to the longitudinal axis of the proximal stent.

In an example, there can be an opening and/or lumen through a proximal stent through which embolic members and/or material is inserted into a distal portion of the aneurysm sac. In an example, this opening and/or lumen can be centrally-located with respect to the proximal surface of the proximal stent. In an example, this opening and/or lumen can be centrally-located with respect to the longitudinal axis of the proximal stent. In an example, this opening and/or lumen can be an opening and/or lumen through a hub into which proximal ends of braided wires or tubes of the stent are bound or attached. In an example, this opening and/or lumen can be off-axial with respect to the longitudinal axis of the proximal stent.

In an example, a tubular mesh can be soldered, melted, glued, or crimped onto an annular member. In an example, an annular member can have an inner ring and an outer ring, wherein a tubular mesh is fixed (e.g. soldered, melted, glued, or crimped) between the two rings. In an example, an annular member can comprise an inner ring or cylinder and an outer elastic band, wherein the tubular mesh is held between the inner and outer portions. In this example, an annular member can be centrally-located with respect to a proximal surface of the flexible net or mesh. In an example, an annular member can be centrally-located with respect to the longitudinal axis of the flexible net or mesh. In an example, an annular member can be a hub into which proximal ends of braided wires or tubes of the stent are bound or attached. In an example, an annular member can be off-axial with respect to the longitudinal axis of the flexible net or mesh.

In an example, a net or mesh can be soldered, melted, glued, or crimped onto an annular member which forms an opening through a flexible net or mesh. In an example, an annular member which forms an opening through a flexible net or mesh can have an inner ring and an outer ring, wherein a net or mesh is fixed (e.g. soldered, melted, glued, or crimped) between the two rings. In an example, an annular member which forms an opening through a flexible net or mesh can comprise an inner ring or cylinder and an outer elastic band, wherein a net or mesh is held between the inner and outer portions. In an example, an annular member which forms an opening through a flexible net or mesh can be centrally-located with respect to a proximal surface of the flexible net or mesh. In an example, an annular member which forms an opening through a flexible net or mesh can be centrally-located with respect to the longitudinal axis of the flexible net or mesh. In an example, an annular member which forms an opening through a flexible net or mesh can be a hub into which proximal ends of braided wires or tubes of the stent are bound or attached. In an example, an annular member which forms an opening through a flexible net or mesh can be off-axial with respect to the longitudinal axis of the flexible net or mesh.

In an example, an opening through a flexible implant through which embolic members and/or embolic material is inserted can be centrally located with respect to the proximal portion of the implant. In an example, an opening through a flexible implant through which embolic members and/or embolic material is inserted can be aligned with the longitudinal axis of the proximal portion of the implant. In an example, an opening through a flexible implant through which embolic members and/or embolic material is inserted can be connected to a catheter. In an example, an opening through a flexible implant through which embolic members and/or embolic material is inserted can be detachably connected to a catheter. In an example, an opening through a flexible implant through which embolic members and/or embolic material is inserted can be connected to a catheter, wherein this connection can be broken by application of electromagnetic energy. Relevant example variations discussed elsewhere in this disclosure or priority-linked disclosures can also be applied to this example.

Figure 9:
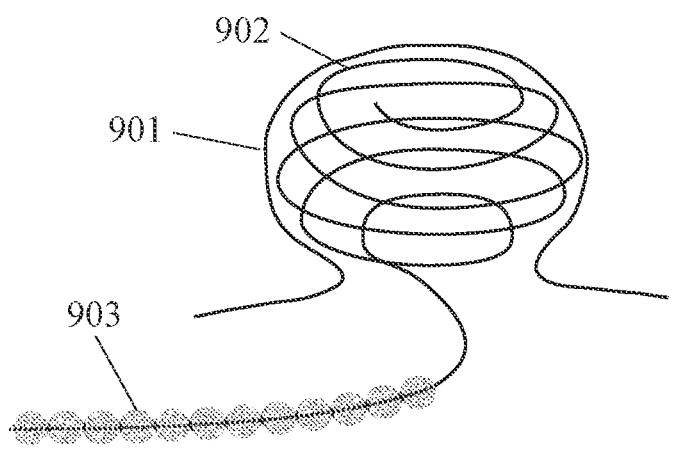
FIG. 9 shows an aneurysm occlusion device comprising a helical wire, wherein the maximum diameter of the helical structure of the wire is larger than the diameter of the aneurysm neck.

FIG. 9 shows an example of a intrasacular aneurysm occlusion device comprising: a helical wire 902 which is configured to be inserted into an aneurysm sac 901, wherein the maximum diameter of the helical structure of the wire is larger than the diameter of the aneurysm neck; and a longitudinal plurality of sliding embolic masses 903 (e.g. compressible balls, soft polyhedrons, microsponges, hydrogels, longitudinal meshes, longitudinal ribbons, or soft coils)

which can slide along the length of the helical wire, wherein the sliding embolic masses are slid (e.g. pushed) along the length of the helical wire into the aneurysm sac after the helical wire has been inserted into the aneurysm sac, and wherein accumulation of the sliding embolic masses within the aneurysm sac reduces and/or prevents blood flow into the aneurysm sac.

As shown in FIG. 9, an intrasacular aneurysm occlusion device can comprise a helical wire. In an example, the maximum diameter of a helical wire structure can expand to be larger than the diameter of an aneurysm neck. In an example, an intrasacular aneurysm occlusion device can comprise: a globular (e.g. spherical, oblate spherical, or ellipsoidal) mesh or net (e.g. mesh, net, shell, or stent) which is configured to be inserted and expanded within an aneurysm sac, wherein the mesh or net comprises a plurality of helical filaments (e.g. wires or strands).

In an example, there can be variation in the thickness, weave or braid density, and/or elasticity of helical filaments along the length (e.g. longitudinal axis) of the mesh or net. In an example, proximal portions of the helical filaments can be thicker than distal portions of the helical filaments. In an example, proximal portions of the helical filaments can be more densely woven or braided together than distal portions of the helical filaments. In an example, proximal portions of the helical filaments can be less elastic than distal portions of the helical filaments. In an example, the helical filaments can intersect and/or overlap each other.

In an example, a first set of helical filaments can spiral around the mesh or net in a first direction (e.g. clockwise) and a second set of helical filaments can spiral around the mesh or net in a second direction (e.g. counter-clockwise), wherein the second direction is radially-opposite the first direction. In an example, first and second ends of the helical filaments can be connected to proximal and distal hubs, respectively. In an example, the helical filaments can extend out distally from a proximal hub, loop around the distal portion of the mesh or net, and then return to the proximal hub, such that both ends of the helical filaments are connected to the proximal hub. In an example, the helical filaments can extend out proximally from a distal hub, loop around the proximal portion of the mesh or net, and then return to the distal hub, such that both ends of the helical filaments are connected to the distal hub.

In an example, an intrasacular aneurysm occlusion device can comprise: a mesh or net (e.g. mesh, net, shell, or stent) which is configured to be inserted and expanded within an aneurysm sac, wherein the mesh or net further comprises: a proximal portion comprising one or more helical or spiral filaments (e.g. wires or strands); and a distal portion comprising a hexagonal (e.g. honeycomb) mesh or grid.

In an example, a flexible sac-filling portion of a device can be created by braiding. In an example, a flexible sac-filling portion of a device can be a porous braided member (with holes, openings, and/or pores). In an example, a flexible sac-filling portion of a device can be braid or weave of filaments, wires, fibers, or threads. In an example, a flexible sac-filling portion can comprise a braid or weave of fibers or threads. In an example, a flexible sac-filling portion of a device comprise helical and/or spiral wires or filaments. In an example, a flexible sac-filling portion of a device can be created by braiding wires or filaments into a braid pattern selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern. In an example, the stiffness of the proximal portion of the net or mesh relative to that of the distal portion can be increased by integrating a helical wire into the proximal portion of the net or mesh.

In an example, a proximal surface of a resilient wider-than-neck portion of a device can have a higher density and/or lower porosity than a distal surface of the resilient wider-than-neck portion. In an example, a proximal part of a resilient wider-than-neck portion of a device can have multiple layers, while a distal part of the resilient wider-than-neck portion only has a single layer. In an example, a flexible sac-filling portion of a device can comprise braided, woven, or wound wires or filaments. In an example, a resilient wider-than-neck portion can comprise an expandable mesh, network, lattice, or radial array of wires or other stiff fibers. In an example, these wires or filament can be helical. In an example, these wires or filaments can comprise radial spokes. In an example, a resilient wider-than-neck portion can have multiple layers, thereby forming a multi-layer stent or neck bridge. In an example, a resilient wider-than-neck portion can be a hollow convex wire mesh, net, lattice, or braided structure.

In an example, a net or mesh which is inserted into an aneurysm sac can have a structure which is selected from the group consisting of: braided or woven shell, braided or woven structure, braided or woven tubular structure with inverted end portions, braided or woven tubular structure with tied ends, braided textile sphere, braided wire sphere, dual-layer braided or woven structure, hollow braided or woven structure, spherical braided or woven structure, and tubular braided or woven structure. In an example, a net or mesh which is inserted into an aneurysm sac can have a structure which is selected from the group consisting of: 3D-printed convex net or mesh, flexible metal mesh or net, metal hexagonal mesh or net, and polymer hexagonal mesh or net.

In an example, a net or mesh with hexagonal openings (e.g. pores) can be made using 3D printing. In an example, a flexible metal net or mesh with hexagonal openings (e.g. pores) can be made by 3D printing with liquid metal. In an example, a net or mesh with hexagonal openings (e.g. pores) can be made by 3D printing with a polymer. In an example, a net or mesh with hexagonal openings (e.g. pores) can be made by 3D printing with an elastomeric polymer. In an example, a net or mesh with hexagonal openings (e.g. pores) can be made by 3D printing with a silicone-based polymer. In an example, a net or mesh with hexagonal openings (e.g. pores) can be made by 3D printing with polydimethylsiloxane (PDMS).

In an example, a proximal portion of a net or mesh which is inserted into an aneurysm sac can have a structure which is selected from the group consisting of: 3D-printed convex proximal portion of a net or mesh, flexible metal mesh or net, metal hexagonal mesh or net, and polymer hexagonal mesh or net. In an example, a proximal portion of a net or mesh which is inserted into an aneurysm sac can have a structure which is selected from the group consisting of: containment bag, dual-layer body, flexible aneurysm liner, hollow framing structure, hollow shell structure, and thin-wall flexible metal sphere with holes. In an example, a proximal portion of a net or mesh which is inserted into an aneurysm sac can be a balloon with holes. In an example, a proximal portion of a net or mesh which is inserted into an aneurysm sac can be a cellular lattice or a hollow array of biological cells.

In an example, an aneurysm occlusion device which is inserted into an aneurysm sac can have a structure which is selected from the group consisting of: braided or woven shell, braided or woven structure, braided or woven tubular structure with inverted end portions, braided or woven tubular structure with tied ends, braided textile sphere, braided wire sphere, dual-layer braided or woven structure, hollow braided or woven structure, spherical braided or woven structure, and tubular braided or woven structure. In an example, an aneurysm occlusion device which is inserted into an aneurysm sac can have a structure which is selected from the group consisting of: 3D-printed convex aneurysm occlusion device, flexible metal mesh or net, metal hexagonal mesh or net, and polymer hexagonal mesh or net.

In an example, an intrasaccular aneurysm occlusion device can comprise: an expandable net or mesh with hexagonal openings (e.g. pores) which is inserted into an aneurysm sac; three-dimensional embolic members which are inserted into and retained within the expandable net or mesh after the net or mesh has been inserted into the aneurysm sac; and one or more strands which connect embolic members to each other; wherein the expandable net or mesh further comprises a radially-resilient proximal portion which self-expands within the aneurysm sac to cover the aneurysm neck from inside the aneurysm sac; and wherein the expandable net or mesh further comprises a flexible distal portion which is expanded by the insertion and retention of embolic members within the net or mesh to conform to the shape of remaining portion of the aneurysm sac which is not filled by the proximal portion.

In an example, at least one portion of a net or mesh for insertion into an aneurysm sac can be selected from the group consisting of: 3D-printed convex net or mesh, balloon with holes, braided or woven shell, braided or woven structure, braided or woven tubular structure with inverted end portions, braided or woven tubular structure with tied ends, braided textile sphere, braided wire sphere, cellular lattice, containment bag, dual-layer body, dual-layer braided or woven structure, flexible aneurysm liner, flexible metal mesh or net, hollow braided or woven structure, hollow framing structure, hollow shell structure, hollow sphere of biological cells, metal hexagonal mesh or net, polymer hexagonal mesh or net, spherical braided or woven structure, thin-wall flexible metal sphere with holes, and tubular braided or woven structure.

In an example, the proximal portion can have a shape which is selected from the group consisting of: heart-shaped, helical, hemispherical, hexagon-shaped, hexahedron, hub-and-spokes-shaped, multi-lobed, multi-planar, non-spherical surface of revolution, noodle-shaped, oblate spheroid, octagon-shaped, octahedron, ovaloid, and pancake-shaped. In an example, the proximal portion can have a shape which is selected from the group consisting of: paraboloid of revolution, peanut-shaped, pear-shaped, pentagonal-shaped, polyhedron-shaped, prolate-spheroid-shaped, pyramidal, rectangular, and ring-shaped. In an example, the proximal portion can have a shape which is selected from the group consisting of: semi-circular, sinusoidal, shape with radially-extending-protrusions, spherical, square, star-shaped, tapered, telescoping, tetrahedronal, toroidal, and truncated-sphere-shaped.

In one possible embodiment, a bowl-of-spaghetti type aneurysm occlusion device can comprise: (a) a catheter; (b) one or more embolic coils which are inserted through the catheter into an aneurysm sac; (c) a neck bridge (e.g. stent, lattice, mesh, or framework) which expands (e.g. self-expands) to a bowl or cup shape within the aneurysm sac, expanding to a diameter which is at least 10% larger than the diameter of the aneurysm neck; (d) an opening in the neck bridge through which the coils are inserted into the aneurysm sac; and (e) a remotely-activated closure mechanism which closes the opening after the coils have been inserted into the aneurysm sac. Alternatively, a bowl-of-spaghetti type aneurysm occlusion device can comprise: (a) a catheter; (b) one or more embolic coils which are inserted through the catheter into an aneurysm sac; (c) a neck bridge (e.g. stent, lattice, mesh, or framework) with a helical wire which expands (e.g. self-expands) into a bowl or cup shape within the aneurysm sac, expanding to a diameter which is larger than the maximum diameter of the aneurysm neck; (d) a (central) opening in the neck bridge through which the coils are inserted into the aneurysm sac; and (e) a closure mechanism which closes the opening after the coils have been inserted into the aneurysm sac.

In an example, a string-of-pearls embolic member can comprise a longitudinal series of embolic components (e.g. the pearls) which are connected by a flexible filament or wire (e.g. the string). In an example, a flexible net can have quadrilateral-shaped openings. In an example, a flexible net can have hexagonal openings. In an example, a flexible net can have triangular openings. In an example, a flexible net can have circular openings. In an example, embolic components (e.g. the pearls) in a string-of-pearls embolic member can be generally spherical and openings in a flexible net can be generally circular. In an example, embolic components (e.g. the pearls) in a string-of-pearls embolic member can be generally polygonal and openings in a flexible net can be generally circular. In an example, embolic components (e.g. the pearls) in a string-of-pearls embolic member can be generally spherical and openings in a flexible net can be generally polygonal.

In an example, a neck bridge can comprise a wire mesh. In an example, a neck bridge can comprise a braided or woven wire mesh. In an example, wires in neck bridge can have a hub-and-spoke configuration, wherein the hubs are at central proximal and distal locations and the spokes extend radially outward from the hubs. In an example, wires in a neck bridge can have a ring-and-spoke configuration, wherein a subset of wires extend radially outward from a central location and a subset of wires encircle the central location in rings. In an example, rings may be closer together toward the center of the neck bridge than the periphery of the neck bridge. In an example, wires in a neck bridge may form a hexagonal mesh (e.g. honeycomb mesh). In an example, wires in neck bridge may be undulating (e.g. sinusoidal). In an example, a neck bridge can comprise a wire mesh with helical wires.

In an example, a tubular mesh can have hexagonal openings. In an example, a tubular mesh with hexagonal openings can be made using 3D printing. In an example, a flexible metal tubular mesh with hexagonal openings can be made by 3D printing with liquid metal. In an example, a tubular mesh with hexagonal openings can be made by 3D printing with a polymer. In an example, a tubular mesh with hexagonal openings can be made by 3D printing with an elastomeric polymer. In an example, a tubular mesh with hexagonal openings can be made by 3D printing with a silicone-based polymer. In an example, a tubular mesh with hexagonal openings can be made by 3D printing with polydimethylsiloxane (PDMS).

In an example, a method for occluding a cerebral aneurysm can comprise: delivering (e.g. delivering, advancing, and/or navigating) a flexible 3D-printed implant through a longitudinal lumen (e.g. a catheter) to a cerebral aneurysm, wherein the 3D-printed implant is a net or mesh with hexagonal pores and/or openings; wherein the flexible 3D-printed implant is in a radially-constrained first configuration as it is delivered through the lumen; inserting the flexible 3D-printed implant into the aneurysm sac from the lumen, wherein the flexible 3D-printed implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the flexible implant, wherein accumulation of embolic members and/or embolic material inside the flexible 3D-printed implant causes the flexible 3D-printed implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant. Relevant example variations discussed elsewhere in this disclosure or priority-linked disclosures can also be applied to this example.

Figure 10:
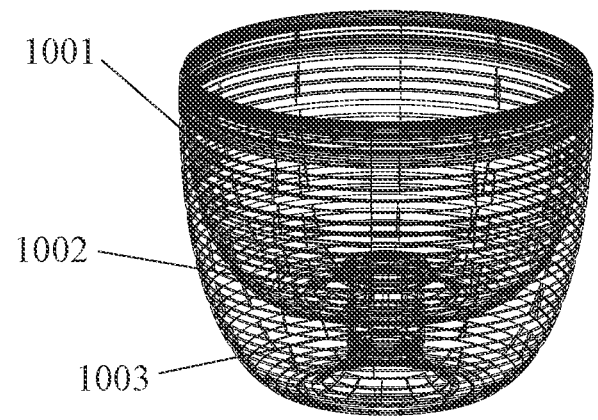
FIG. 10 shows a first example of an aneurysm occlusion device with a multi-layer or multi-wall bowl-shaped mesh with a proximal layer or wall which faces toward the aneurysm neck and a distal layer or wall which faces toward the aneurysm dome.

FIG. 10 shows an example of a intrasacular aneurysm occlusion device comprising: at least one annular member (two in this example, a proximal annular member 1003 and a distal annular member 1002), wherein an annular member is selected from the group consisting of a ring, a band, a cylinder, a tube, and a catheter; a flexible net or mesh, wherein the flexible net or mesh has a spherical, ellipsoidal, generally-globular, hemispherical, and/or bowl-shaped configuration formed by encircling, pinching, inverting, and/or everting a tubular mesh 1001 at one or more longitudinal locations using the at least one annular member.

In an example, a flexible net or mesh can have a radially-compressed configuration for delivery through a catheter into an aneurysm sac. In an example, a flexible net or mesh can be inserted and expanded within the aneurysm sac. In an example, embolic members and/or embolic material can be inserted into the interior of the flexible net or mesh through the one or more of the annular members. In the example shown in FIG. 10, there are two annular members: a proximal annular member which radially constrains the proximal end of a tubular mesh; and a distal annular member which radially constrains a distal end of the tubular mesh. In this example, the flexible net or mesh has a double-layer bowl shape which is formed from the tubular mesh. In FIG. 10, the distal portion of the tubular mesh has been compressed and inverted into the concavity of the proximal portion of the tubular mesh, thereby forming a double-layer bowl-shaped flexible net or mesh.

The intrasacular aneurysm occlusion device shown in FIG. 10 is a multi-layer or multi-wall bowl-shaped mesh which is configured to be inserted into an aneurysm sac and cover the aneurysm neck. In this example, a multi-layer or multi-wall bowl-shaped mesh is formed by radially-constraining and then folding, inverting, and/or everting a tubular mesh. In the example shown in FIG. 10, a bowl-shaped mesh with a proximal layer or wall and a distal layer or wall is formed by radially-constraining and then folding, inverting, and/or everting a tubular mesh. In another example, a proximal layer or wall of a bowl-shaped mesh and a distal layer or wall of the bowl-shaped mesh can be separate structures which are connected together.

In an example, one or more embolic members can be inserted through an opening in the proximal wall of a double-walled bowl-shaped mesh. The one or more embolic members promote therapeutic clotting of blood inside in the aneurysm sac, so the one or more embolic members are thrombogenic members. In an example, one or more thrombogenic members can be inserted into the double-walled bowl-shaped mesh. In an example, a thrombogenic member can be inserted into the interior of a double-walled bowl-shaped mesh.

As discussed above, an intrasacular aneurysm occlusion device can comprise: a multi-layer or multi-wall bowl-shaped mesh or net (e.g. mesh, net, shell, or stent) which is configured to be inserted and expanded within an aneurysm sac so as to cover the aneurysm neck, wherein the mesh or net further comprises: a proximal layer or wall which is configured to face toward the aneurysm neck; a distal layer or wall which is configured to face toward the aneurysm dome; and a thrombogenic member which is inserted between the proximal layer or wall and the distal layer or wall.

In an example, the proximal layer or wall of a double-walled bowl-shaped mesh can have a hemispherical, hemiellipsoidal, or half-toroidal shape. In an example, the distal layer or wall of the double-walled bowl-shaped mesh can have a hemispherical, hemi-ellipsoidal, frustal, funnel, and/or hyperboloidal shape. In an example, there can be a gap between the proximal layer or wall and the distal layer or wall. In an example, there can be variability in the width of the gap between the proximal layer or wall and the distal layer or wall. In an example, the gap between the proximal layer or wall and the distal layer or wall can be narrowest toward the center and toward the circumference of the mesh or net. In an example, the proximal layer or wall and the distal layer or wall can be connected to a central proximal hub. In an example, the proximal layer or wall and the distal layer or wall can be portions of the same (tubular) mesh structure which has been folded, radially-constrained, inverted, and/or everted.

In an example, a bowl-shaped mesh can be shaped like a lower section of a sphere or ellipsoid. In an example, a bowl-shaped mesh can have a hemi-spherical or hemi-ellipsoidal shape. In an example, a bowl-shaped mesh can be a wire mesh and/or frame. In an example, a bowl-shaped mesh can have a single layer. In an example, a bowl-shaped mesh can have two or more layers. In an example, a bowl-shaped mesh can be a woven or braided wire mesh and/or frame. In an example, a bowl-shaped mesh can be cut from metal. In an example, a bowl-shaped mesh can be made from metal and polymer components. In an example, a bowl-shaped mesh can comprise a wire frame and a polymer mesh. In an example, a bowl-shaped mesh can comprise a wire frame and a polymer layer. In an example, a bowl-shaped mesh can be made from nitinol. In an example, the bowl-shaped mesh can radially-expand within the aneurysm sac to a width which is greater than the width of the aneurysm neck.

In an example, a bowl-shaped mesh can have uniform elasticity. In an example, a bowl-shaped mesh can have uniform porosity. In an example, a bowl-shaped mesh can have a uniform durometer level. In an example, a central portion of a bowl-shaped mesh can have a greater durometer level than a peripheral portion of a bowl-shaped mesh. In an example, the outer perimeter of a bowl-shaped mesh can have a greater durometer level than the central portion of a bowl-shaped mesh. In an example, a central portion of a bowl-shaped mesh can have a lower durometer level a peripheral portion of a bowl-shaped mesh. In an example, the outer perimeter of a bowl-shaped mesh can have a lower durometer level than the central portion of a bowl-shaped mesh. In an example, layers of a bowl-shaped mesh can be closer together near the center of the bowl-shaped mesh and farther apart around the periphery of the bowl-shaped mesh.

In an example, a central portion of a bowl-shaped mesh can have greater porosity than a peripheral portion of a bowl-shaped mesh. In an example, the outer perimeter of a bowl-shaped mesh can have greater porosity than the central portion of a bowl-shaped mesh. In an example, a central portion of a bowl-shaped mesh can have lower porosity than a peripheral portion of a bowl-shaped mesh. In an example, the outer perimeter of a bowl-shaped mesh can have lower porosity than the central portion of a bowl-shaped mesh. In an example, a central portion of a bowl-shaped mesh can be more elastic than a peripheral portion of a bowl-shaped mesh. In an example, the outer perimeter of a bowl-shaped mesh can be more elastic than the central portion of a bowl-shaped mesh. In an example, the outer perimeter of a bowl-shaped mesh can be less elastic than the central portion of a bowl-shaped mesh. In an example, layers of a bowl-shaped mesh can be farther apart near the center of the bowl-shaped mesh and closer together in the periphery of the bowl-shaped mesh.

In this example, a lumen can extend outward from surface of a bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved and bound together and the bowl-shaped mesh can be formed before the device is deployed. In an example, the distal and proximal ends of the tubular mesh can be moved and bound together to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted. Relevant example variations discussed elsewhere in this disclosure or priority-linked disclosures can also be applied to this example.

Figure 11:
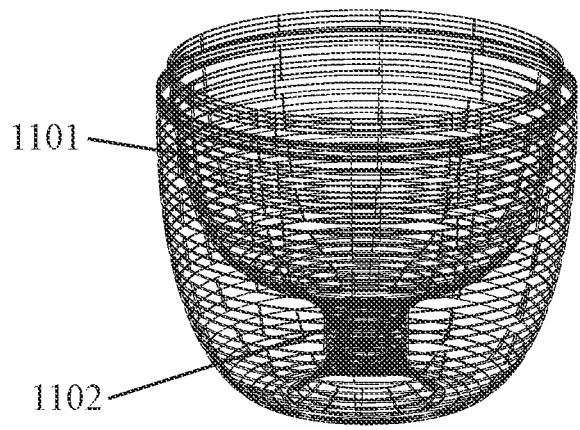
FIG. 11 shows a second example of an aneurysm occlusion device with a multi-layer or multi-wall bowl-shaped mesh with a proximal layer or wall which faces toward the aneurysm neck and a distal layer or wall which faces toward the aneurysm dome.

FIG. 11 shows an example of an intrasacular aneurysm occlusion device comprising: at least one annular member (in this example, a single mid-section annular member 1102), wherein an annular member is selected from the group consisting of a ring, a band, a cylinder, a tube, and a catheter; a flexible net or mesh, wherein the flexible net or mesh has a spherical, ellipsoidal, generally-globular, hemispherical, and/or bowl-shaped first configuration when it is formed by encircling, pinching, inverting, and/or everting a tubular mesh 1101 at one or more longitudinal locations using the at least one annular member.

In an example, a flexible net or mesh can have a radially-compressed configuration for delivery through a catheter into an aneurysm sac. In an example, a flexible net or mesh can be inserted and expanded within an aneurysm sac. In an example, embolic members and/or embolic material can be inserted into the interior of a flexible net or mesh through one or more of the annular members. In this example, there is a single annular member which radially constrains a mid-section of a tubular mesh. In the example shown in FIG. 11, the flexible net or mesh has a double-layer or double-wall bowl shape which is formed from a tubular mesh.

The intrasacular aneurysm occlusion device shown in FIG. 11 is a multi-layer or multi-wall bowl-shaped mesh which is configured to be inserted into an aneurysm sac and cover the aneurysm neck. In this example, a multi-layer or multi-wall bowl-shaped mesh is formed by radially-constraining and then folding, inverting, and/or everting a tubular mesh. In the example shown in FIG. 11, a bowl-shaped mesh with a proximal layer or wall and a distal layer or wall is formed by radially-constraining and then folding, inverting, and/or everting a tubular mesh. In another example, a proximal layer or wall of a bowl-shaped mesh and a distal layer or wall of the bowl-shaped mesh can be separate structures which are connected together.

In an example, embolic members and/or embolic material can be inserted through a central opening in the proximal wall of a double-walled bowl-shaped mesh. The embolic members and/or embolic material promote therapeutic clotting of blood inside in the aneurysm sac, so the embolic members and/or embolic material is thrombogenic. In an example, thrombogenic members and/or material is inserted into the double-walled bowl-shaped mesh. In an example, a thrombogenic member can be inserted into the interior of a double-walled bowl-shaped mesh.

As discussed above, an intrasacular aneurysm occlusion device can comprise: a multi-layer or multi-wall bowl-shaped mesh or net (e.g. mesh, net, shell, or stent) which is configured to be inserted and expanded within an aneurysm sac so as to cover the aneurysm neck, wherein the mesh or net further comprises: a proximal layer or wall which is configured to face toward the aneurysm neck; a distal layer or wall which is configured to face toward the aneurysm dome; and a thrombogenic member which is inserted between the proximal layer or wall and the distal layer or wall.

In an example, the proximal layer or wall of a double-walled bowl-shaped mesh can have a hemispherical, hemiellipsoidal, or half-toroidal shape. In an example, the distal layer or wall of the double-walled bowl-shaped mesh can have a hemispherical, hemi-ellipsoidal, frustal, funnel, and/or hyperboloidal shape. In an example, there can be a gap between the proximal layer or wall and the distal layer or wall. In an example, there can be variability in the width of the gap between the proximal layer or wall and the distal layer or wall. In an example, the gap between the proximal layer or wall and the distal layer or wall can be narrowest toward the center and toward the circumference of the mesh or net. In an example, the proximal layer or wall and the distal layer or wall can be connected to a central proximal hub. In an example, the proximal layer or wall and the distal layer or wall can be portions of the same (tubular) mesh structure which has been folded, radially-constrained, inverted, and/or everted.

In an example, a bowl-shaped mesh can be shaped like a lower section of a sphere or ellipsoid. In an example, a bowl-shaped mesh can have a hemi-spherical or hemi-ellipsoidal shape. In an example, a bowl-shaped mesh can be a wire mesh and/or frame. In an example, a bowl-shaped mesh can have a single layer. In an example, a bowl-shaped mesh can have two or more layers. In an example, a bowl-shaped mesh can be a woven or braided wire mesh and/or frame. In an example, a bowl-shaped mesh can be cut from metal. In an example, a bowl-shaped mesh can be made from metal and polymer components. In an example, a bowl-shaped mesh can comprise a wire frame and a polymer mesh. In an example, a bowl-shaped mesh can comprise a wire frame and a polymer layer. In an example, a bowl-shaped mesh can be made from nitinol. In an example, the bowl-shaped mesh can radially-expand within the aneurysm sac to a width which is greater than the width of the aneurysm neck.

In an example, a bowl-shaped mesh can have uniform elasticity. In an example, a bowl-shaped mesh can have uniform porosity. In an example, a bowl-shaped mesh can have a uniform durometer level. In an example, a central portion of a bowl-shaped mesh can have a greater durometer level than a peripheral portion of a bowl-shaped mesh. In an example, the outer perimeter of a bowl-shaped mesh can have a greater durometer level than the central portion of a bowl-shaped mesh. In an example, a central portion of a bowl-shaped mesh can have a lower durometer level a peripheral portion of a bowl-shaped mesh. In an example, the outer perimeter of a bowl-shaped mesh can have a lower durometer level than the central portion of a bowl-shaped mesh. In an example, layers of a bowl-shaped mesh can be closer together near the center of the bowl-shaped mesh and farther apart around the periphery of the bowl-shaped mesh.

In an example, a central portion of a bowl-shaped mesh can have greater porosity than a peripheral portion of a bowl-shaped mesh. In an example, the outer perimeter of a bowl-shaped mesh can have greater porosity than the central portion of a bowl-shaped mesh. In an example, a central portion of a bowl-shaped mesh can have lower porosity than a peripheral portion of a bowl-shaped mesh. In an example, the outer perimeter of a bowl-shaped mesh can have lower porosity than the central portion of a bowl-shaped mesh. In an example, a central portion of a bowl-shaped mesh can be more elastic than a peripheral portion of a bowl-shaped mesh. In an example, the outer perimeter of a bowl-shaped mesh can be more elastic than the central portion of a bowl-shaped mesh. In an example, the outer perimeter of a bowl-shaped mesh can be less elastic than the central portion of a bowl-shaped mesh. In an example, layers of a bowl-shaped mesh can be farther apart near the center of the bowl-shaped mesh and closer together in the periphery of the bowl-shaped mesh.

In this example, a lumen can extend outward from surface of a bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved and bound together and the bowl-shaped mesh can be formed before the device is deployed. In an example, the distal and proximal ends of the tubular mesh can be moved and bound together to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted. Relevant example variations discussed elsewhere in this disclosure or priority-linked disclosures can also be applied to this example.

Figure 12:
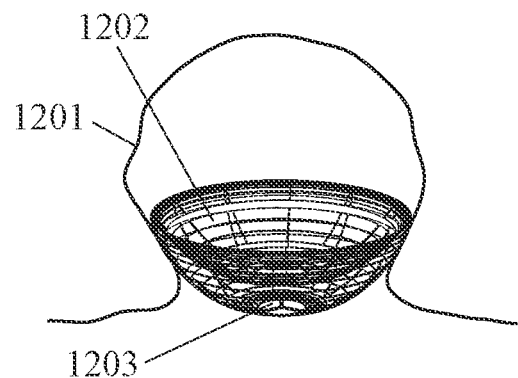
FIG. 12 shows a third example of an aneurysm occlusion device with a multi-layer or multi-wall bowl-shaped mesh with a proximal layer or wall which faces toward the aneurysm neck and a distal layer or wall which faces toward the aneurysm dome, including a proximal opening through which embolic members and/or material are inserted.

FIG. 12 shows an example of an intrasacular aneurysm occlusion device comprising: a double-layer bowl-shaped mesh 1202 which is configured to be radially-expanded to bridge the neck of an aneurysm 1201; and a valve 1203 in the double-layer bowl-shaped mesh through which embolic members (e.g. embolic coils, hydrogels, microsponges, beads, or string-of-pearls embolic strands) or liquid embolic material (which solidifies in the aneurysm) can be inserted into the aneurysm.

The intrasacular aneurysm occlusion device shown in FIG. 12 is a multi-layer or multi-wall bowl-shaped mesh which is configured to be inserted into an aneurysm sac and cover the aneurysm neck. In an example, a multi-layer or multi-wall bowl-shaped mesh can be formed by radially-constraining and then folding, inverting, and/or everting a tubular mesh. In the example, a bowl-shaped mesh with a proximal layer or wall and a distal layer or wall can be formed by radially-constraining and then folding, inverting, and/or everting a tubular mesh. In another example, a proximal layer or wall of a bowl-shaped mesh and a distal layer or wall of the bowl-shaped mesh can be separate structures which are connected together.

In an example, one or more embolic members can be inserted through a central opening (with a valve) in the proximal wall of a double-walled bowl-shaped mesh. The one or more embolic members promote therapeutic clotting of blood inside in the aneurysm sac, so the one or more embolic members are thrombogenic. In an example, a thrombogenic member can be inserted into the double-walled bowl-shaped mesh. In an example, a thrombogenic member can be inserted into the interior of the double-walled bowl-shaped mesh.

As discussed above, an intrasacular aneurysm occlusion device can comprise: a multi-layer or multi-wall bowl-shaped mesh or net (e.g. mesh, net, shell, or stent) which is configured to be inserted and expanded within an aneurysm sac so as to cover the aneurysm neck, wherein the mesh or net further comprises: a proximal layer or wall which is configured to face toward the aneurysm neck; a distal layer or wall which is configured to face toward the aneurysm dome; and a thrombogenic member which is inserted between the proximal layer or wall and the distal layer or wall.

In an example, the proximal layer or wall of a double-walled bowl-shaped mesh can have a hemispherical, hemiellipsoidal, or half-toroidal shape. In an example, the distal layer or wall of the double-walled bowl-shaped mesh can have a hemispherical, hemi-ellipsoidal, frustal, funnel, and/or hyperboloidal shape. In an example, there can be a gap between the proximal layer or wall and the distal layer or wall. In an example, there can be variability in the width of the gap between the proximal layer or wall and the distal layer or wall. In an example, the gap between the proximal layer or wall and the distal layer or wall can be narrowest toward the center and toward the circumference of the mesh or net. In an example, the proximal layer or wall and the distal layer or wall can be connected to a central proximal hub. In an example, the proximal layer or wall and the distal layer or wall can be portions of the same (tubular) mesh structure which has been folded, radially-constrained, inverted, and/or everted.

In an example, a bowl-shaped mesh can be shaped like a lower section of a sphere or ellipsoid. In an example, a bowl-shaped mesh can have a hemi-spherical or hemi-ellipsoidal shape. In an example, a bowl-shaped mesh can be a wire mesh and/or frame. In an example, a bowl-shaped mesh can have a single layer. In an example, a bowl-shaped mesh can have two or more layers. In an example, a bowl-shaped mesh can be a woven or braided wire mesh and/or frame. In an example, a bowl-shaped mesh can be cut from metal. In an example, a bowl-shaped mesh can be made from metal and polymer components. In an example, a bowl-shaped mesh can comprise a wire frame and a polymer mesh. In an example, a bowl-shaped mesh can comprise a wire frame and a polymer layer. In an example, a bowl-shaped mesh can be made from nitinol. In an example, the bowl-shaped mesh can radially-expand within the aneurysm sac to a width which is greater than the width of the aneurysm neck.

In an example, a bowl-shaped mesh can have uniform elasticity. In an example, a bowl-shaped mesh can have uniform porosity. In an example, a bowl-shaped mesh can have a uniform durometer level. In an example, a central portion of a bowl-shaped mesh can have a greater durometer level than a peripheral portion of a bowl-shaped mesh. In an example, the outer perimeter of a bowl-shaped mesh can have a greater durometer level than the central portion of a bowl-shaped mesh. In an example, a central portion of a bowl-shaped mesh can have a lower durometer level a peripheral portion of a bowl-shaped mesh. In an example, the outer perimeter of a bowl-shaped mesh can have a lower durometer level than the central portion of a bowl-shaped mesh. In an example, layers of a bowl-shaped mesh can be closer together near the center of the bowl-shaped mesh and farther apart around the periphery of the bowl-shaped mesh.

In an example, a central portion of a bowl-shaped mesh can have greater porosity than a peripheral portion of a bowl-shaped mesh. In an example, the outer perimeter of a bowl-shaped mesh can have greater porosity than the central portion of a bowl-shaped mesh. In an example, a central portion of a bowl-shaped mesh can have lower porosity than a peripheral portion of a bowl-shaped mesh. In an example, the outer perimeter of a bowl-shaped mesh can have lower porosity than the central portion of a bowl-shaped mesh. In an example, a central portion of a bowl-shaped mesh can be more elastic than a peripheral portion of a bowl-shaped mesh. In an example, the outer perimeter of a bowl-shaped mesh can be more elastic than the central portion of a bowl-shaped mesh. In an example, the outer perimeter of a bowl-shaped mesh can be less elastic than the central portion of a bowl-shaped mesh. In an example, layers of a bowl-shaped mesh can be farther apart near the center of the bowl-shaped mesh and closer together in the periphery of the bowl-shaped mesh.

In this example, a lumen can extend outward from surface of a bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved and bound together and the bowl-shaped mesh can be formed before the device is deployed. In an example, the distal and proximal ends of the tubular mesh can be moved and bound together to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted. Relevant example variations discussed elsewhere in this disclosure or priority-linked disclosures can also be applied to this example.

Figure 13:
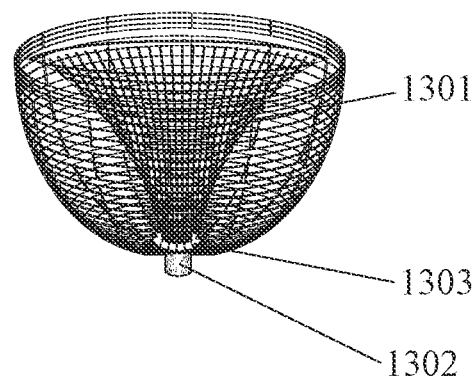
FIG. 13 shows a fourth example of an aneurysm occlusion device with a multi-layer or multi-wall bowl-shaped mesh with a proximal layer or wall which faces toward the aneurysm neck and a distal layer or wall which faces toward the aneurysm dome, including a proximal hub through which embolic members and/or material are inserted.

FIG. 13 shows an example of an intrasacular aneurysm occlusion device comprising: a mesh 1301 which has been inserted into and expanded within an aneurysm sac, wherein the mesh has a bowl (e.g. hemispherical, hemi-ellipsoidal, or paraboloidal) shape with a distal-facing concavity after expansion; one or more longitudinal embolic members (e.g. embolic coils, embolic ribbons, or string-of-pearls embolic strands); a lumen 1302 (e.g. a tube, catheter, cylinder, and/or ring) through the mesh, wherein the longitudinal embolic members are inserted through the lumen into the aneurysm sac; and a radial constraint 1303 (e.g. a ring, band, strap, suture, cord, clasp, or clip) which binds the mesh to the lumen.

In an example, this intrasaccular aneurysm occlusion device can comprise: a mesh which is inserted into and expanded within an aneurysm sac, wherein the mesh has a bowl shape (e.g. hemispherical, hemi-ellipsoidal, or paraboloidal shape) with a distal-facing concavity after expansion; one or more longitudinal embolic members (e.g. embolic coils, embolic ribbons, or string-of-pearls embolic strands); and a central lumen (e.g. a tube, catheter, cylinder, and/or ring) through the mesh, wherein the longitudinal embolic members are inserted through the lumen into the aneurysm sac.

The intrasacular aneurysm occlusion device shown in FIG. 13 is a multi-layer or multi-wall bowl-shaped mesh which is configured to be inserted into an aneurysm sac so as to cover the aneurysm neck. In an example, a multi-layer or multi-wall bowl-shaped mesh can be formed by radially-constraining and then folding, inverting, and/or everting a tubular mesh. In an example, a bowl-shaped mesh with a proximal layer or wall and a distal layer or wall can be formed by radially-constraining and then folding, inverting, and/or everting a tubular mesh. In another example, a proximal layer or wall of a bowl-shaped mesh and a distal layer or wall of the bowl-shaped mesh can be separate structures which are connected together.

As shown in FIG. 13, the proximal layer or wall of this device can have a hemispherical or hemi-ellipsoidal shape with a distal-facing concavity and the distal layer or wall of this device can have a funnel, paraboloidal, or frustal shape with a distal-facing concavity. As shown in this example, there can be a gap between the proximal layer or wall and the distal layer or wall. As shown here, there can be variability in the width of the gap between the proximal layer or wall and the distal layer or wall. The gap between the proximal layer or wall and the distal layer or wall can be narrowest toward the center and toward the circumference of the mesh or net. In an example, the proximal layer or wall and the distal layer or wall can both be connected to a central proximal hub. In an example, the proximal layer or wall and the distal layer or wall can be portions of the same (tubular) mesh structure which has been folded, radially-constrained, inverted, and/or everted.

In an example, one or more embolic members can be inserted through a central opening or hub in the proximal wall of a double-walled bowl-shaped mesh. An embolic member can promote therapeutic clotting of blood inside in the aneurysm sac, so an embolic member can be thrombogenic. In an example, thrombogenic members can be inserted into the double-walled bowl-shaped mesh. In an example, a thrombogenic member can be inserted into the interior of the double-walled bowl-shaped mesh.

As discussed above, an intrasacular aneurysm occlusion device can comprise: a multi-layer or multi-wall bowl-shaped mesh or net (e.g. mesh, net, shell, or stent) which is configured to be inserted and expanded within an aneurysm sac so as to cover the aneurysm neck, wherein the mesh or net further comprises: a proximal layer or wall which is configured to face toward the aneurysm neck; a distal layer or wall which is configured to face toward the aneurysm dome; and a thrombogenic member which is inserted between the proximal layer or wall and the distal layer or wall.

In an example, the proximal layer or wall of a double-walled bowl-shaped mesh can have a hemispherical, hemiellipsoidal, or half-toroidal shape. In an example, the distal layer or wall of the double-walled bowl-shaped mesh can have a hemispherical, hemi-ellipsoidal, frustal, funnel, and/or hyperboloidal shape. In an example, there can be a gap between the proximal layer or wall and the distal layer or wall. In an example, there can be variability in the width of the gap between the proximal layer or wall and the distal layer or wall. In an example, the gap between the proximal layer or wall and the distal layer or wall can be narrowest toward the center and toward the circumference of the mesh or net. In an example, the proximal layer or wall and the distal layer or wall can be connected to a central proximal hub. In an example, the proximal layer or wall and the distal layer or wall can be portions of the same (tubular) mesh structure which has been folded, radially-constrained, inverted, and/or everted.

In an example, a bowl-shaped mesh can be shaped like a lower section of a sphere or ellipsoid. In an example, a bowl-shaped mesh can have a hemi-spherical or hemi-ellipsoidal shape. In an example, a bowl-shaped mesh can be a wire mesh and/or frame. In an example, a bowl-shaped mesh can have a single layer. In an example, a bowl-shaped mesh can have two or more layers. In an example, a bowl-shaped mesh can be a woven or braided wire mesh and/or frame. In an example, a bowl-shaped mesh can be cut from metal. In an example, a bowl-shaped mesh can be made from metal and polymer components. In an example, a bowl-shaped mesh can comprise a wire frame and a polymer mesh. In an example, a bowl-shaped mesh can comprise a wire frame and a polymer layer. In an example, a bowl-shaped mesh can be made from nitinol. In an example, the bowl-shaped mesh can radially-expand within the aneurysm sac to a width which is greater than the width of the aneurysm neck.

In an example, a bowl-shaped mesh can have uniform elasticity. In an example, a bowl-shaped mesh can have uniform porosity. In an example, a bowl-shaped mesh can have a uniform durometer level. In an example, a central portion of a bowl-shaped mesh can have a greater durometer level than a peripheral portion of a bowl-shaped mesh. In an example, the outer perimeter of a bowl-shaped mesh can have a greater durometer level than the central portion of a bowl-shaped mesh. In an example, a central portion of a bowl-shaped mesh can have a lower durometer level a peripheral portion of a bowl-shaped mesh. In an example, the outer perimeter of a bowl-shaped mesh can have a lower durometer level than the central portion of a bowl-shaped mesh. In an example, layers of a bowl-shaped mesh can be closer together near the center of the bowl-shaped mesh and farther apart around the periphery of the bowl-shaped mesh.

In an example, a central portion of a bowl-shaped mesh can have greater porosity than a peripheral portion of a bowl-shaped mesh. In an example, the outer perimeter of a bowl-shaped mesh can have greater porosity than the central portion of a bowl-shaped mesh. In an example, a central portion of a bowl-shaped mesh can have lower porosity than a peripheral portion of a bowl-shaped mesh. In an example, the outer perimeter of a bowl-shaped mesh can have lower porosity than the central portion of a bowl-shaped mesh. In an example, a central portion of a bowl-shaped mesh can be more elastic than a peripheral portion of a bowl-shaped mesh. In an example, the outer perimeter of a bowl-shaped mesh can be more elastic than the central portion of a bowl-shaped mesh. In an example, the outer perimeter of a bowl-shaped mesh can be less elastic than the central portion of a bowl-shaped mesh. In an example, layers of a bowl-shaped mesh can be farther apart near the center of the bowl-shaped mesh and closer together in the periphery of the bowl-shaped mesh.

In this example, a lumen can extend outward from surface of a bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved and bound together and the bowl-shaped mesh can be formed before the device is deployed. In an example, the distal and proximal ends of the tubular mesh can be moved and bound together to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted. Relevant example variations discussed elsewhere in this disclosure or priority-linked disclosures can also be applied to this example.

Figure 14:
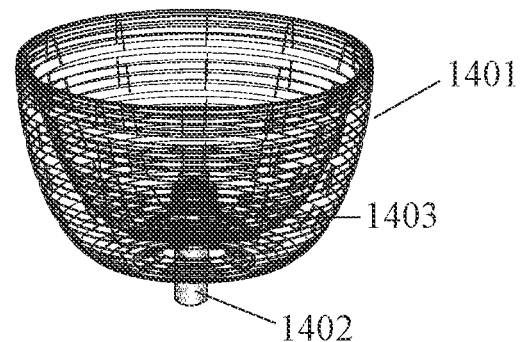
FIG. 14 shows a fifth example of an aneurysm occlusion device with a multi-layer or multi-wall bowl-shaped mesh with a proximal layer or wall which faces toward the aneurysm neck and a distal layer or wall which faces toward the aneurysm dome, including an axial column through which embolic members and/or material are inserted.

FIG. 14 shows an example of an intrasacular aneurysm occlusion device comprising: a mesh 1401 which is inserted into and expanded within an aneurysm sac, wherein the mesh has a bowl shape (e.g. a hemispherical, hemi-ellipsoidal, or paraboloidal shape) with a distal-facing concavity after expansion; one or more longitudinal embolic members (e.g. embolic coils, embolic ribbons, or string-of-pearls embolic strands); a proximal lumen 1402 (e.g. a tube, catheter, cylinder, and/or ring) through the mesh, wherein the longitudinal embolic members are inserted through the lumen into the aneurysm sac; and a hub 1403 to which ends of the mesh are connected. In this example, the hub is located at the distal end of the tubular mesh until it is moved in a proximal direction during eversion of the distal end into the proximal portion of the mesh.

In an example, an intrasaccular aneurysm occlusion device can comprise: a mesh which is inserted into and expanded within an aneurysm sac, wherein the mesh has a bowl shape (e.g. hemispherical, hemi-ellipsoidal, or paraboloidal shape) with a distal-facing concavity after expansion; one or more longitudinal embolic members (e.g. embolic coils, embolic ribbons, or string-of-pearls embolic strands); and a central lumen (e.g. a tube, catheter, cylinder, and/or ring) through the mesh, wherein embolic members are inserted through the lumen into the aneurysm sac.

The intrasacular aneurysm occlusion device shown in FIG. 14 is a multi-layer or multi-wall bowl-shaped mesh which is configured to be inserted into an aneurysm sac so as to cover the aneurysm neck. In an example, a multi-layer or multi-wall bowl-shaped mesh can be formed by radially-constraining and then folding, inverting, and/or everting a tubular mesh. In an example, a bowl-shaped mesh with a proximal layer or wall and a distal layer or wall can be formed by radially-constraining and then folding, inverting, and/or everting a tubular mesh. In another example, a proximal layer or wall of a bowl-shaped mesh and a distal layer or wall of the bowl-shaped mesh can be separate structures which are connected together.

As shown in FIG. 14, the proximal layer or wall of this device can have a hemispherical or hemi-ellipsoidal shape with a distal-facing concavity and the distal layer or wall of this device can also have a hemispherical or hemi-ellipsoidal shape with a distal-facing concavity. As shown in this example, there can be a gap between the proximal layer or wall and the distal layer or wall. As shown here, there can be variability in the width of the gap between the proximal layer or wall and the distal layer or wall. The gap between the proximal layer or wall and the distal layer or wall can be narrowest toward the circumference of the mesh or net. In an example, the proximal layer or wall and the distal layer or wall can both be connected to a central proximal hub. In an example, the proximal layer or wall and the distal layer or wall can be portions of the same (tubular) mesh structure which has been folded, radially-constrained, inverted, and/or everted.

In an example, one or more embolic members can be inserted through a central opening or hub in the proximal wall of a double-walled bowl-shaped mesh. An embolic member can promote therapeutic clotting of blood inside in the aneurysm sac, so an embolic member can be thrombogenic. In an example, thrombogenic members can be inserted into the double-walled bowl-shaped mesh. In an example, a thrombogenic member can be inserted into the interior of the double-walled bowl-shaped mesh.

As discussed above, an intrasacular aneurysm occlusion device can comprise: a multi-layer or multi-wall bowl-shaped mesh or net (e.g. mesh, net, shell, or stent) which is configured to be inserted and expanded within an aneurysm sac so as to cover the aneurysm neck, wherein the mesh or net further comprises: a proximal layer or wall which is configured to face toward the aneurysm neck; a distal layer or wall which is configured to face toward the aneurysm dome; and a thrombogenic member which is inserted between the proximal layer or wall and the distal layer or wall.

In an example, the proximal layer or wall of a double-walled bowl-shaped mesh can have a hemispherical, hemiellipsoidal, or half-toroidal shape. In an example, the distal layer or wall of the double-walled bowl-shaped mesh can have a hemispherical, hemi-ellipsoidal, frustal, funnel, and/or hyperboloidal shape. In an example, there can be a gap between the proximal layer or wall and the distal layer or wall. In an example, there can be variability in the width of the gap between the proximal layer or wall and the distal layer or wall. In an example, the gap between the proximal layer or wall and the distal layer or wall can be narrowest toward the center and toward the circumference of the mesh or net. In an example, the proximal layer or wall and the distal layer or wall can be connected to a central proximal hub. In an example, the proximal layer or wall and the distal layer or wall can be portions of the same (tubular) mesh structure which has been folded, radially-constrained, inverted, and/or everted.

In an example, a bowl-shaped mesh can be shaped like a lower section of a sphere or ellipsoid. In an example, a bowl-shaped mesh can have a hemi-spherical or hemi-ellipsoidal shape. In an example, a bowl-shaped mesh can be a wire mesh and/or frame. In an example, a bowl-shaped mesh can have a single layer. In an example, a bowl-shaped mesh can have two or more layers. In an example, a bowl-shaped mesh can be a woven or braided wire mesh and/or frame. In an example, a bowl-shaped mesh can be cut from metal. In an example, a bowl-shaped mesh can be made from metal and polymer components. In an example, a bowl-shaped mesh can comprise a wire frame and a polymer mesh. In an example, a bowl-shaped mesh can comprise a wire frame and a polymer layer. In an example, a bowl-shaped mesh can be made from nitinol. In an example, the bowl-shaped mesh can radially-expand within the aneurysm sac to a width which is greater than the width of the aneurysm neck.

In an example, a bowl-shaped mesh can have uniform elasticity. In an example, a bowl-shaped mesh can have uniform porosity. In an example, a bowl-shaped mesh can have a uniform durometer level. In an example, a central portion of a bowl-shaped mesh can have a greater durometer level than a peripheral portion of a bowl-shaped mesh. In an example, the outer perimeter of a bowl-shaped mesh can have a greater durometer level than the central portion of a bowl-shaped mesh. In an example, a central portion of a bowl-shaped mesh can have a lower durometer level a peripheral portion of a bowl-shaped mesh. In an example, the outer perimeter of a bowl-shaped mesh can have a lower durometer level than the central portion of a bowl-shaped mesh. In an example, layers of a bowl-shaped mesh can be closer together near the center of the bowl-shaped mesh and farther apart around the periphery of the bowl-shaped mesh.

In an example, a central portion of a bowl-shaped mesh can have greater porosity than a peripheral portion of a bowl-shaped mesh. In an example, the outer perimeter of a bowl-shaped mesh can have greater porosity than the central portion of a bowl-shaped mesh. In an example, a central portion of a bowl-shaped mesh can have lower porosity than a peripheral portion of a bowl-shaped mesh. In an example, the outer perimeter of a bowl-shaped mesh can have lower porosity than the central portion of a bowl-shaped mesh. In an example, a central portion of a bowl-shaped mesh can be more elastic than a peripheral portion of a bowl-shaped mesh. In an example, the outer perimeter of a bowl-shaped mesh can be more elastic than the central portion of a bowl-shaped mesh. In an example, the outer perimeter of a bowl-shaped mesh can be less elastic than the central portion of a bowl-shaped mesh. In an example, layers of a bowl-shaped mesh can be farther apart near the center of the bowl-shaped mesh and closer together in the periphery of the bowl-shaped mesh.

In this example, a lumen can extend outward from surface of a bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved and bound together and the bowl-shaped mesh can be formed before the device is deployed. In an example, the distal and proximal ends of the tubular mesh can be moved and bound together to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted. Relevant example variations discussed elsewhere in this disclosure or priority-linked disclosures can also be applied to this example.

Figure 15:
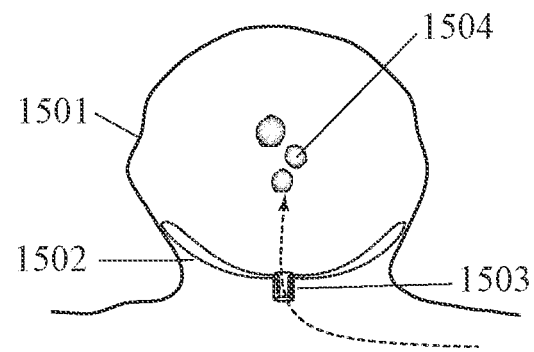
FIG. 15 shows a sixth example of an aneurysm occlusion device with a multi-layer or multi-wall bowl-shaped mesh with a proximal layer or wall which faces toward the aneurysm neck and a distal layer or wall which faces toward the aneurysm dome, including a proximal hub through which embolic members and/or material are inserted.

FIG. 15 shows an example of an intrasacular aneurysm occlusion device comprising: a bowl-shaped mesh 1502 which is configured to be inserted into and expanded within an aneurysm sac 1501 so as to span the neck of the aneurysm from inside the aneurysm sac, wherein the bowl-shaped mesh is formed by pinching and/or binding together the distal and proximal ends of a tubular mesh; a lumen (e.g. cylinder, ring, band, tube, or torus) 1503 within which the distal and proximal ends of the tubular mesh are pinched and/or bound; and one or more embolic members (e.g. coils, string-of-pearls embolic strands, hydrogels, microsponges, or beads) 1504 which are inserted through the lumen into the aneurysm sac, wherein accumulation of the one or more embolic members in the aneurysm sac helps to occlude the aneurysm and to hold the bowl-shaped mesh against the neck of the aneurysm.

In an example, an intrasaccular aneurysm occlusion device can comprise: a mesh which is inserted into and expanded within an aneurysm sac, wherein the mesh has a bowl shape (e.g. hemispherical, hemi-ellipsoidal, or paraboloidal shape) with a distal-facing concavity after expansion; one or more embolic members (e.g. embolic coils, embolic ribbons, or string-of-pearls embolic strands); and a central lumen (e.g. a tube, catheter, cylinder, and/or ring) through the mesh, wherein embolic members are inserted through the lumen into the aneurysm sac.

The intrasacular aneurysm occlusion device shown in FIG. 15 is a multi-layer or multi-wall bowl-shaped mesh which is configured to be inserted into an aneurysm sac so as to cover the aneurysm neck. In an example, a multi-layer or multi-wall bowl-shaped mesh can be formed by radially-constraining and then folding, inverting, and/or everting a tubular mesh. In an example, a bowl-shaped mesh with a proximal layer or wall and a distal layer or wall can be formed by radially-constraining and then folding, inverting, and/or everting a tubular mesh. In another example, a proximal layer or wall of a bowl-shaped mesh and a distal layer or wall of the bowl-shaped mesh can be separate structures which are connected together.

As shown in FIG. 15, the proximal layer or wall of this device can have a hemispherical or hemi-ellipsoidal shape with a distal-facing concavity and the distal layer or wall of this device can also have a hemispherical or hemi-ellipsoidal shape with a distal-facing concavity. In an example, the proximal layer or wall and the distal layer or wall can both be connected to a central proximal hub. In an example, the proximal layer or wall and the distal layer or wall can be portions of the same (tubular) mesh structure which has been folded, radially-constrained, inverted, and/or everted.

In an example, one or more embolic members can be inserted through a central opening or hub in the proximal wall of a double-walled bowl-shaped mesh. An embolic member can promote therapeutic clotting of blood inside in the aneurysm sac, so an embolic member can be thrombogenic. In an example, thrombogenic members can be inserted into the double-walled bowl-shaped mesh. In an example, a thrombogenic member can be inserted into the interior of the double-walled bowl-shaped mesh.

As discussed above, an intrasacular aneurysm occlusion device can comprise: a multi-layer or multi-wall bowl-shaped mesh or net (e.g. mesh, net, shell, or stent) which is configured to be inserted and expanded within an aneurysm sac so as to cover the aneurysm neck, wherein the mesh or net further comprises: a proximal layer or wall which is configured to face toward the aneurysm neck; a distal layer or wall which is configured to face toward the aneurysm dome; and a thrombogenic member which is inserted between the proximal layer or wall and the distal layer or wall.

In an example, the proximal layer or wall of a double-walled bowl-shaped mesh can have a hemispherical, hemiellipsoidal, or half-toroidal shape. In an example, the distal layer or wall of the double-walled bowl-shaped mesh can have a hemispherical, hemi-ellipsoidal, frustal, funnel, and/or hyperboloidal shape. In an example, the proximal layer or wall and the distal layer or wall can be connected to a central proximal hub. In an example, the proximal layer or wall and the distal layer or wall can be portions of the same (tubular) mesh structure which has been folded, radially-constrained, inverted, and/or everted.

In an example, a bowl-shaped mesh can be shaped like a lower section of a sphere or ellipsoid. In an example, a bowl-shaped mesh can have a hemi-spherical or hemi-ellipsoidal shape. In an example, a bowl-shaped mesh can be a wire mesh and/or frame. In an example, a bowl-shaped mesh can have a single layer. In an example, a bowl-shaped mesh can have two or more layers. In an example, a bowl-shaped mesh can be a woven or braided wire mesh and/or frame. In an example, a bowl-shaped mesh can be cut from metal. In an example, a bowl-shaped mesh can be made from metal and polymer components. In an example, a bowl-shaped mesh can comprise a wire frame and a polymer mesh. In an example, a bowl-shaped mesh can comprise a wire frame and a polymer layer. In an example, a bowl-shaped mesh can be made from nitinol. In an example, the bowl-shaped mesh can radially-expand within the aneurysm sac to a width which is greater than the width of the aneurysm neck.

In an example, a bowl-shaped mesh can have uniform elasticity. In an example, a bowl-shaped mesh can have uniform porosity. In an example, a bowl-shaped mesh can have a uniform durometer level. In an example, a central portion of a bowl-shaped mesh can have a greater durometer level than a peripheral portion of a bowl-shaped mesh. In an example, the outer perimeter of a bowl-shaped mesh can have a greater durometer level than the central portion of a bowl-shaped mesh. In an example, a central portion of a bowl-shaped mesh can have a lower durometer level a peripheral portion of a bowl-shaped mesh. In an example, the outer perimeter of a bowl-shaped mesh can have a lower durometer level than the central portion of a bowl-shaped mesh. In an example, layers of a bowl-shaped mesh can be closer together near the center of the bowl-shaped mesh and farther apart around the periphery of the bowl-shaped mesh.

In an example, a central portion of a bowl-shaped mesh can have greater porosity than a peripheral portion of a bowl-shaped mesh. In an example, the outer perimeter of a bowl-shaped mesh can have greater porosity than the central portion of a bowl-shaped mesh. In an example, a central portion of a bowl-shaped mesh can have lower porosity than a peripheral portion of a bowl-shaped mesh. In an example, the outer perimeter of a bowl-shaped mesh can have lower porosity than the central portion of a bowl-shaped mesh. In an example, a central portion of a bowl-shaped mesh can be more elastic than a peripheral portion of a bowl-shaped mesh. In an example, the outer perimeter of a bowl-shaped mesh can be more elastic than the central portion of a bowl-shaped mesh. In an example, the outer perimeter of a bowl-shaped mesh can be less elastic than the central portion of a bowl-shaped mesh. In an example, layers of a bowl-shaped mesh can be farther apart near the center of the bowl-shaped mesh and closer together in the periphery of the bowl-shaped mesh.

In this example, a lumen can extend outward from surface of a bowl-shaped mesh in a proximal direction. In this example, the bowl-shaped mesh is double-layered. In this example, the concavity of the bowl-shaped mesh opens in a distal direction. In an example, the distal and proximal ends of the tubular mesh can be moved and bound together and the bowl-shaped mesh can be formed before the device is deployed. In an example, the distal and proximal ends of the tubular mesh can be moved and bound together to form the bowl-shaped mesh after the device has been inserted into and expanded within the aneurysm sac. In an example, the distal end of the tubular mesh can be inverted or partially inverted. In an example, the proximal end of the tubular mesh can be inverted or partially inverted. Relevant example variations discussed elsewhere in this disclosure or priority-linked disclosures can also be applied to this example.

FIGS. 16 and 17 show side views, at two different times, of an intrasacular aneurysm occlusion device comprising: a proximal mesh (e.g. mesh, net, stent, or shell) 1602 which is configured to be inserted and expanded within an aneurysm sac 1601; a distal mesh (e.g. mesh, net, stent, or shell) 1603 which is configured to be inserted and expanded within the aneurysm sac; an opening 1604 in the proximal mesh; and embolic members and/or embolic material 1605 which is inserted through the opening into the distal mesh, wherein insertion of the embolic members and/or embolic material into the distal mesh expands the distal mesh to fill the aneurysm sac. FIG. 16 shows this device at a first time, before the embolic members and/or embolic material has been inserted into the distal mesh. FIG. 17 shows this device at a second time, after the embolic members and/or embolic material has been inserted into the distal mesh, thereby expanding the distal mesh to conform to the shape of the walls of even an irregularly-shaped aneurysm sac.

In this example, the proximal mesh is bowl-shaped (e.g. hemispherical, hemiellipsoidal, paraboloidal, or half-toroidal). In this example, a portion of the distal mesh is inside a distal-facing concavity of the proximal mesh. In this example, a portion of the distal mesh is inside the distal-facing concavity of a bowl-shaped proximal mesh. In another example, a proximal mesh can be inside a distal mesh. In an example, a distal mesh can have a single layer and a proximal mesh can have two or more layers. With respect to these meshes, proximal means closer to the aneurysm neck and distal means farther from the aneurysm neck.

In an example, a distal mesh can have a globular (e.g. spherical, oblate spherical, or ellipsoidal) shape before it is expanded by insertion of embolic members and/or embolic material. In an example, the distal mesh is flexible so that it can conform to the shape of even an irregularly-shaped aneurysm sack after it is expanded by insertion of embolic members and/or embolic material. In an example, the distal mesh can be radially-symmetric before it is expanded by insertion of embolic members and/or embolic material, but radially-asymmetric after it is expanded by insertion of embolic members and/or embolic material if the aneurysm sac is radially-asymmetric.

In an example, a proximal mesh and/or a distal mesh can be a hexagonal (e.g. honeycomb) mesh. In an example, a proximal mesh and/or a distal mesh can have hexagonal openings. In another example, a proximal mesh and/or a distal mesh can have quadrilateral openings. In an example, a proximal mesh and/or a distal mesh can have triangular openings. In an example, a proximal mesh and/or a distal mesh can have spherical or elliptical openings. In an example, a proximal mesh and/or a distal mesh can be braided or woven. In an example, a proximal mesh and/or a distal mesh can be 3D printed.

In an example, a proximal mesh can have a first elasticity level and a distal mesh can have a second elasticity level, wherein the second elasticity level is greater than the first elasticity level. In an example, a proximal mesh can have a first flexibility level and a distal mesh can have a second flexibility level, wherein the second flexibility level is greater than the first flexibility level. In an example, a proximal mesh can have a first stiffness level and a distal mesh can have a second stiffness level, wherein the second stiffness level is less than the first stiffness level. In an example, a proximal mesh can have a first durometer level and a distal mesh can have a second durometer level, wherein the second durometer level is less than the first durometer level.

In an example, a proximal mesh can have a first elasticity level and a distal mesh can have a second elasticity level, wherein the second elasticity level is at least 25% greater than the first elasticity level. In an example, a proximal mesh can have a first flexibility level and a distal mesh can have a second flexibility level, wherein the second flexibility level is at least 25% greater than the first flexibility level. In an example, a proximal mesh can have a first stiffness level and a distal mesh can have a second stiffness level, wherein the second stiffness level is at least 25% less than the first stiffness level. In an example, a proximal mesh can have a first durometer level and a distal mesh can have a second durometer level, wherein the second durometer level is at least 25% less than the first durometer level.

In an example, a proximal mesh can comprise filaments (e.g. wires) with a first diameter and a distal mesh can comprise filaments with a second diameter, wherein the second diameter is less than the first diameter. In an example, a proximal mesh can have a first filament (e.g. wire) density and a distal mesh can have a second filament density, wherein the second filament density is less than the first filament density. In an example, a proximal mesh can have a first porosity level and a distal mesh can have a second porosity level, wherein the second porosity level is greater than the first filament density. In an example, a proximal mesh can comprise filaments (e.g. wires) with a first percentage of polymer material and a distal mesh can comprise filaments with a second percentage of polymer material, wherein the second percentage is greater than the first percentage. In an example, a proximal mesh can comprise filaments (e.g. wires) with a first percentage of metal and a distal mesh can comprise filaments with a second percentage of metal, wherein the second percentage is less than the first percentage.

In an example, a proximal mesh can comprise filaments (e.g. wires) with a first diameter and a distal mesh can comprise filaments with a second diameter, wherein the second diameter is at least 25% less than the first diameter. In an example, a proximal mesh can have a first filament (e.g. wire) density and a distal mesh can have a second filament density, wherein the second filament density is at least 25% less than the first filament density. In an example, a proximal mesh can have a first porosity level and a distal mesh can have a second porosity level, wherein the second porosity level is at least 25% greater than the first filament density. In an example, a proximal mesh can comprise filaments (e.g. wires) with a first percentage of polymer material and a distal mesh can comprise filaments with a second percentage of polymer material, wherein the second percentage is at least 25% greater than the first percentage. In an example, a proximal mesh can comprise filaments (e.g. wires) with a first percentage of metal and a distal mesh can comprise filaments with a second percentage of metal, wherein the second percentage is at least 25% less than the first percentage.

In an example, a proximal mesh and a distal mesh can be separate structures. In an example, a proximal mesh and a distal mesh can be formed as separate structures and then attached together. In an example, a proximal mesh and a distal mesh can be formed as separate structures and then attached together by a proximal hub. In an example, a proximal hub can have an annular shape (e.g. ring, band, or cylinder). Embolic members can be inserted through a lumen in the proximal hub. In an example, a proximal mesh and/or a distal mesh can be 3D printed. In an example, a distal mesh can be 3D printed using an elastomeric polymer. In an example, a distal mesh can be an elastomeric polymer mesh. In an example, an elastomeric polymer can really mesh up your mind.

In an example, a proximal mesh and a distal mesh can be formed from the same continuous mesh structure. In an example, a proximal mesh and a distal mesh can be lobes, sections, or portions of the same continuous mesh structure. In an example, a proximal mesh and a distal mesh can be formed by radially-constraining, inverted, everting, and/or folding a continuous mesh structure. In an example, a proximal mesh and a distal mesh can be formed by radially-constraining, inverted, everting, and/or folding a tubular mesh. In an example, a proximal mesh and a distal mesh can be formed by radially-constraining a tubular mesh at one or more locations with one or more annular components (e.g. rings, bands, or cylinders) and then inverting, everting, and/or folding the tubular mesh.

In an example, a proximal mesh and a distal mesh can be formed by: (a) radially-constraining a portion of the proximal longitudinal half of a tubular mesh with an annular member (e.g. ring, band, or column); and then (b) everting the section which is proximal to the annular member in a distal direction over the rest of the tubular mesh. In an example, a proximal mesh and a distal mesh can be formed by: (a) radially-constraining the distal end of a tubular mesh; (b) radially-constraining a portion of the proximal longitudinal half of a tubular tube with an annular member (e.g. ring, band, or column), and then (c) everting the section which is proximal to the annular member in a distal direction over the rest of the tubular mesh.

In an example, an opening in a proximal mesh through which embolic members and/or embolic material is inserted can be at the center of the proximal mesh. In an example, an opening in a proximal mesh through which embolic members and/or embolic material is inserted can be inside a proximal hub which connects the proximal mesh and the distal mesh. In an example, an opening in a proximal mesh through which embolic members and/or embolic material is inserted can be inside an annular member (e.g. ring, band, or cylinder) which radially constrains a tubular mesh. In an example, an opening in a proximal mesh through which embolic members and/or embolic material is inserted can be inside a central column which spans the central longitudinal axis of the proximal mesh. In an example, the device can further comprise a closure mechanism and/or valve which opens or closes the opening through which embolic members and/or material is inserted. In an example, the device can further comprise a closure mechanism and/or valve which is remotely controlled by the device operator to open or close the opening through which embolic members and/or material is inserted.

In an example, an annular member which is used to radially-constrain a tubular mesh to form proximal and distal meshes can comprise an inner cylinder (e.g. ring, band, or cylinder) and an outer cylinder (e.g. ring, band, or cylinder), wherein the proximal and distal meshes are between the inner cylinder and the outer cylinder and wherein embolic members and/or material is inserted through the lumen of the inner cylinder. In an example, an annular member which is used to connect separately-formed proximal and distal meshes can comprise an inner cylinder (e.g. ring, band, or cylinder) and an outer cylinder (e.g. ring, band, or cylinder), wherein the proximal and distal meshes are held (e.g. pinched, crimped, compressed, soldered, or glued) between the inner cylinder and the outer cylinder and wherein embolic members and/or material is inserted through the lumen of the inner cylinder.

In an example, embolic members and/or material can comprise string-of-pearls embolic strands, wherein a string-of-pearls embolic strand further comprises embolic pieces (e.g. balls, beads, or three-dimensional polygonal pieces) which are longitudinally linked by one or more longitudinal filaments (e.g. filaments, strings, threads, sutures, wires, or coils). In this example, a string-of-pearls embolic strand can comprise soft, compressible balls or beads which are longitudinally linked together by string, thread, suture, or wire. In an example, a string-of-pearls embolic strand can comprise hydrogel pieces which are longitudinally linked together by string, thread, suture, or wire. In an example, a string-of-pearls embolic strand can comprise microsponges which are longitudinally linked together by string, thread, suture, or wire. In an example, a string-of-pearls embolic strand can comprise beads which are longitudinally linked together by string, thread, suture, or wire.

In an example, embolic pieces in a string-of-pearls embolic strand can all have the same size. In another example, the sizes of embolic pieces along a string-of-pearls can decrease in size as one progresses from the distal end to the proximal end of the strand. In an example, embolic pieces in a string-of-pearls embolic strand can all be separated by the same inter-piece distance. In another example, the inter-piece distance between embolic pieces along a string-of-pearls can increase in size as one progresses from the distal end to the proximal end of the strand. In an example, embolic pieces in a string-of-pearls embolic strand can all be the same shape. In another example, the shapes of embolic pieces along a string-of-pearls can become less arcuate as one progresses from the distal end to the proximal end of the strand. In an example, embolic pieces in a string-of-pearls embolic strand can all have the same durometer level. In another example, the durometer levels of embolic pieces along a string-of-pearls can become lower as one progresses from the distal end to the proximal end of the strand.

In an example, embolic members and/or embolic material can be selected from the group consisting of: string-of-pearls embolic strands; coils; hydrogel pieces; microsponges; beads; embolic ribbons; and congealing embolic liquid. In an example, the average size of embolic members can be greater than the average size of openings in the distal mesh. In an example, the average size of embolic members can be at least 25% greater than the average size of openings in the distal mesh. In an example, the average distance between embolic pieces in a string-of-pearls embolic strand can be greater than the average size of openings in the distal mesh. In an example, the average distance between embolic pieces in a string-of-pearls embolic strand can be at least 50% greater than the average size of openings in the distal mesh. In an example, the average distance between embolic pieces in a string-of-pearls embolic strand can be greater than the average size of embolic pieces in the embolic strand. In an example, the average distance between embolic pieces in a string-of-pearls embolic strand can be at least twice the average size of embolic pieces in the embolic strand.

In an example, embolic members can have different shapes than openings in the distal mesh to reduce the chances of embolic members protruding out from the openings. In an example, embolic members can expand after they are inserted into the aneurysm sac. In an example, embolic members can be hydrogels or microsponges which expand after they are inserted into the aneurysm sac. In an example, embolic members in a string-of-pearls embolic strand can slid along a connecting strand. In an example, embolic members in a string-of-pearls embolic strand can slid along a connecting strand in one direction (e.g. proximal or distal), but not in the other direction.

In an example, embolic members and/or embolic material can be pushed through an opening into a distal mesh by a longitudinal pushing member such as a wire. In an example, embolic members and/or embolic material can be pushed through the opening into the distal mesh by a liquid flow. In an example, embolic members and/or embolic material can be pushed into the distal mesh by a plunger mechanism. In an example, embolic members and/or embolic material can be pushed into the distal mesh by a rotating helical mechanism.

In an example, the quantity and/or volume of embolic members and/or embolic material which is inserted into the distal mesh can be based on estimation of the volume of the aneurysm sack from medical imaging. In an example, the quantity and/or volume of embolic members and/or embolic material which is inserted into the distal mesh can be based on estimation of the volume of the aneurysm sack from 3D medical imaging. In an example, the device can be part of a system which tracks the quantity and/or volume of embolic members and/or embolic material inserted into the distal mesh. In an example, the device can be part of a system which tracks and controls the volume of embolic members and/or embolic material inserted into the distal mesh in order to match the cumulative volume of the aneurysm sac which is estimated from 3D medical imaging. This can help to avoid over-filling or under-filling the aneurysm sac.

In an example, a distal mesh can be made with material with a durometer level less than 50 so that it can conform to the shapes of asymmetric lobes in an irregularly-shaped aneurysm sac when the distal mesh is expanded in the aneurysm sac by the insertion of embolic members and/or embolic material. In one embodiment, a proximal mesh can be less lubricious than a distal mesh. In another example, an opening in a proximal mesh through which embolic members and/or material is inserted is closed remotely by the device operator by insertion of glue (or other congealing substance) after embolic members and/or material has been inserted into a distal mesh. In an example, a distal mesh can be sufficiently elastic, flexible, and/or stretchable such that it can conform to the shapes of asymmetric lobes in an irregularly-shaped aneurysm sac when the distal mesh is expanded in the aneurysm sac by the insertion of embolic members and/or embolic material.

In an example, a proximal mesh can have eight or more radial lobes or petals. In another example, the surface area of overlap between a proximal mesh and a distal mesh which is nested inside the proximal mesh can be between 15% and 40% of the surface area of the distal mesh before it is expanded by insertion of embolic members and/or material. In an example, a distal mesh can be sufficiently elastic, flexible, and/or stretchable such that its volume and/or size can be expanded by over 50% by the insertion of embolic members and/or embolic material. In another example, a proximal mesh can have an undulating (e.g. sinusoidal) perimeter. In an example, the surface area of overlap between a proximal mesh and a distal mesh which is nested inside the proximal mesh can be between 30% and 60% of the surface area of the proximal mesh.

In one embodiment, a distal mesh can be made with material with a Shore 00 Hardness level less than 70 so that it can conform to the shapes of asymmetric lobes in an irregularly-shaped aneurysm sac when the distal mesh is expanded in the aneurysm sac by the insertion of embolic members and/or embolic material. In an example, a proximal mesh can be more lubricious than a distal mesh. In another example, an opening in a proximal mesh through which embolic members and/or material is inserted is closed remotely by the device operator by pinching or crimping after embolic members and/or material has been inserted into a distal mesh. In an example, a distal mesh can be larger than a proximal mesh. In an example, a proximal mesh and a distal mesh are only connected and/or attached to each other at a proximal hub. In an example, an opening in a proximal mesh through which embolic members and/or material is inserted is closed after embolic members and/or material has been inserted into a distal mesh.

In another example, this device can further comprise a detachment mechanism in a distal portion of a catheter which separates and detaches a longitudinal embolic member when a sufficient volume of the embolic member has been inserted into the aneurysm sac to fill the aneurysm sac. In an example, a distal mesh can be made with material with a Shore 00 Hardness level less than 50 so that it can conform to the shapes of asymmetric lobes in an irregularly-shaped aneurysm sac when the distal mesh is expanded in the aneurysm sac by the insertion of embolic members and/or embolic material. In one embodiment, a proximal mesh can have a bowl, inverted-dome, and/or inverted umbrella shape. In an example, an opening in a proximal mesh through which embolic members and/or material is inserted is closed remotely by the device operator by a valve after embolic members and/or material has been inserted into a distal mesh.

In an example, a distal mesh can be made with material with a Shore 00 Hardness level less than 30 so that it can conform to the shapes of asymmetric lobes in an irregularly-shaped aneurysm sac when the distal mesh is expanded in the aneurysm sac by the insertion of embolic members and/or embolic material. In another example, a proximal mesh can have a coating which promotes attachment of the mesh to tissue (e.g. the walls of the sack around the aneurysm neck). In an example, filament-connected embolic pieces in a string-of-pearls embolic strand can be closer together after they are inserted into a distal mesh than before they are inserted into the distal mesh. In another example, a distal mesh can be made with material with a sufficiently-low durometer level and/or Share 00 Hardness level that it can conform to the shapes of asymmetric lobes in an irregularly-shaped aneurysm sac when the distal mesh is expanded in the aneurysm sac by the insertion of embolic members and/or embolic material.

In an example, a proximal mesh can have a coating which promotes attachment of the mesh to tissue (e.g. the walls of the sack around the aneurysm neck) but the distal mesh does not have this coating to enable the distal mesh to slide over the walls of the aneurysm as it expands to fill the aneurysm. In an example, openings in the proximal mesh and openings in the distal meshes are not aligned with each other, except for a central opening through which embolic members and/or embolic material is inserted into the distal mesh. In one embodiment, a distal mesh can be less-tightly woven and/or braided than a proximal mesh. In an example, a proximal mesh can be a two-layer and/or two-wall bowl-shaped mesh which is formed by compressing and/or inverting a first half of a globular mesh into a second half of the globular mesh.

In another example, an opening in a proximal mesh through which embolic members and/or material is inserted is closed by a valve after embolic members and/or material has been inserted into a distal mesh. In an example, a distal mesh can be more elastic than a proximal mesh. In an example, a proximal mesh can have a distal-facing concavity. In an example, the proximal mesh and the distal mesh can occlude at least 70% of the volume of an aneurysm after expansion of the distal mesh by the insertion of embolic members and/or material. In one embodiment, a distal mesh can be more flexible than a proximal mesh. In another example, a proximal mesh can have a funnel, flared, and/or hyperboloidal shape.

In an example, the proximal mesh and the distal mesh can occlude at least 80% of the volume of an aneurysm after expansion of the distal mesh by the insertion of embolic members and/or material. In another example, a distal mesh can be more hydrophobic than a proximal mesh. In an example, a proximal mesh can have a hemispherical shape. In an example, the proximal mesh and the distal mesh can occlude at least 90% of the volume of an aneurysm after expansion of the distal mesh by the insertion of embolic members and/or material. In an example, a proximal mesh and a distal mesh are not coaxial as they are being delivered through a catheter to an aneurysm sac, but are coaxial after being inserted and expanded within the aneurysm sac. In an example, a proximal mesh can have radial lobes or petals.

In another example, this device can further comprise a cutting mechanism in a distal portion of a catheter which cuts a longitudinal embolic member when a sufficient volume of the embolic member has been inserted into the aneurysm sac to fill the aneurysm sac. In one embodiment, a distal mesh can be wider than a proximal mesh. In an example, a proximal mesh can have four radial lobes or petals. In one embodiment, the surface area of overlap between a proximal mesh and a distal mesh which is nested inside the proximal mesh can be between 30% and 60% of the surface area of the distal mesh before it is expanded by insertion of embolic members and/or material. In another example, a distal mesh can be longer than a proximal mesh.

In an example, a proximal mesh can be a two-layer and/or two-wall bowl-shaped mesh which is formed by compressing and/or inverting a first half of a globular mesh into a second half of the globular mesh within the aneurysm sack. In an example, an opening in a proximal mesh through which embolic members and/or material is inserted is closed remotely by the device operator after embolic members and/or material has been inserted into a distal mesh. In an example, a distal mesh can be made with material with a durometer level less than 70 so that it can conform to the shapes of asymmetric lobes in an irregularly-shaped aneurysm sac when the distal mesh is expanded in the aneurysm sac by the insertion of embolic members and/or embolic material. In an example, a proximal mesh can be less hydrophilic than a distal mesh.

In another example, an opening in a proximal mesh through which embolic members and/or material is inserted is closed remotely by the device operator by insertion of a plug after embolic members and/or material has been inserted into a distal mesh. In an example the average distance between a distal-facing surface of a proximal mesh and a proximal-facing surface of a distal mesh is reduced when embolic members and/or material are inserted into the distal mesh. In another example, a proximal mesh and a distal mesh are not concentric as they are being delivered through a catheter to an aneurysm sac, but are concentric after being inserted and expanded within the aneurysm sac. In an example, a proximal mesh can have six radial lobes or petals.

In an example, this device can further comprise a cutting mechanism in a distal portion of a catheter which cuts a string-of-pearls embolic strand when a sufficient volume of the strand has been inserted into the aneurysm sac to fill the aneurysm sac. In one embodiment, a distal mesh can be less dense than a proximal mesh. In an example, a proximal mesh and a distal mesh can be connected by a central proximal hub. In an example, an opening in a proximal mesh through which embolic members and/or material is inserted is closed by insertion of a plug after embolic members and/or material has been inserted into a distal mesh. In another example, this device can further comprise a detachment mechanism in a distal portion of a catheter which separates and detaches a string-of-pearls embolic strand when a sufficient volume of the strand has been inserted into the aneurysm sac to fill the aneurysm sac.

In an example, a proximal mesh and a distal mesh can be connected around the perimeter of the proximal mesh. In another example, a distal mesh can be made with material with a durometer level less than 30 so that it can conform to the shapes of asymmetric lobes in an irregularly-shaped aneurysm sac when the distal mesh is expanded in the aneurysm sac by the insertion of embolic members and/or embolic material. In an example, a proximal mesh can be more hydrophilic than a distal mesh. In an example, an opening in a proximal mesh through which embolic members and/or material is inserted is closed remotely by the device operator by melting after embolic members and/or material has been inserted into a distal mesh. In one embodiment, a distal mesh can be less radially-symmetric than a proximal mesh.

In an example, a proximal mesh and a distal mesh can be connected at a central proximal hub and around the perimeter of the proximal mesh. In an example, an opening in a proximal mesh through which embolic members and/or material is inserted is closed by insertion of glue (or other congealing substance) after embolic members and/or material has been inserted into a distal mesh. In an example, this device can further comprise a detachment mechanism in a distal portion of a catheter which separates and detaches an embolic coil when a sufficient volume of the coil has been inserted into the aneurysm sac to fill the aneurysm sac.

In another example, a distal mesh can be less thick than a proximal mesh. In an example, a proximal mesh and a distal mesh overlap each other only at a proximal hub. In another example, an opening in a proximal mesh through which embolic members and/or material is inserted is closed by pinching or crimping after embolic members and/or material has been inserted into a distal mesh. In an example, a distal mesh can be sufficiently elastic, flexible, and/or stretchable such that its volume and/or size can be expanded by over 100% by the insertion of embolic members and/or embolic material. In another example, a proximal mesh can have an undulating (e.g. sinusoidal) circumference.

In one embodiment, the surface area of overlap between a proximal mesh and a distal mesh which is nested inside the proximal mesh can be between 5% and 20% of the surface area of the distal mesh before it is expanded by insertion of embolic members and/or material. In an example the average distance between a distal-facing surface of a proximal mesh is compressed against a proximal-facing surface of a distal mesh when embolic members and/or material are inserted into the distal mesh. In an example, a proximal mesh and a distal mesh are not nested as they are being delivered through a catheter to an aneurysm sac, but are concentric after being inserted and expanded within the aneurysm sac. In an example, a string-of-pearls embolic strand which is inserted into a distal mesh can be a single continuous strand.

In another example, this device can further comprise a cutting mechanism in a distal portion of a catheter which cuts an embolic coil when a sufficient volume of the coil has been inserted into the aneurysm sac to fill the aneurysm sac. In one embodiment, a distal mesh can be more porous than a proximal mesh. In another example, a proximal mesh can have a paraboloidal shape. In an example, the surface area of overlap between a proximal mesh and a distal mesh which is nested inside the proximal mesh can be between 15% and 40% of the surface area of the proximal mesh.

In an example, a distal mesh can be less stiff than a proximal mesh. In an example, a proximal mesh and a distal mesh do not overlap as they are being delivered through a catheter to an aneurysm sac, but do overlap after being inserted and expanded within the aneurysm sac. In another example, an opening in a proximal mesh through which embolic members and/or material is inserted is closed by melting after embolic members and/or material has been inserted into a distal mesh. In an example, a distal mesh can be more lubricious than a proximal mesh. In an example, a proximal mesh can have a lower-half-toroidal shape. In an example, the surface area of overlap between a proximal mesh and a distal mesh which is nested inside the proximal mesh can be between 5% and 20% of the surface area of the proximal mesh. Relevant example variations discussed elsewhere in this disclosure or priority-linked disclosures can also be applied to this example.

I claim:

1. An intrasaccular aneurysm occlusion device comprising:
- a first mesh or net which is configured to be inserted and expanded within an aneurysm sac, wherein the first mesh or net has a first proximal-to-distal length, wherein the first mesh or net has a first stiffness level, and wherein the first mesh or net has a first elasticity level; and
- a second mesh or net which is in contact with a proximal portion of the first mesh or net, wherein the second mesh or net has a second proximal-to-distal length, wherein the second mesh or net has a second stiffness level, wherein the second mesh or net has a second elasticity level, wherein the second proximal-to-distal length is less than the first proximal-to-distal length, and wherein the second stiffness level is greater than the first stiffness level and/or the second elasticity level is less than the first elasticity level;
- wherein the device further comprises a proximal opening in one or both meshes or nets through which embolic material is inserted;
- wherein the embolic material comprises one or more string-of-pearls embolic strands; wherein a string-of-pearls embolic strand further comprises embolic pieces which are longitudinally linked by one or more filaments; wherein the embolic pieces are balls, beads, or three-dimensional polygonal pieces; and wherein the filaments are strings, threads, sutures, wires, or coils; and
- wherein durometer levels of embolic pieces along the string-of-pearls embolic strand become lower as one progresses from a distal end to a proximal end of the strand.

* * * * *